United States Patent [19]
Gordon et al.

[11] 4,135,247
[45] Jan. 16, 1979

[54] TOMOGRAPHY SIGNAL PROCESSING SYSTEM

[75] Inventors: Bernard M. Gordon, Magnolia; Leopold Neumann, Lexington; John McG. Dobbs, Arlington, all of Mass.

[73] Assignee: Siemens Aktiengesellschaft, Berlin & Munich, Fed. Rep. of Germany

[21] Appl. No.: 824,632

[22] Filed: Aug. 15, 1977

[51] Int. Cl.² .................. G01T 1/16; G06F 15/52
[52] U.S. Cl. .............................. 364/414; 250/445 T
[58] Field of Search ............. 364/414, 518, 515, 527; 250/369, 445 T

[56] References Cited
U.S. PATENT DOCUMENTS

| 3,778,614 | 12/1973 | Hounsfield | 250/362 |
| 4,042,811 | 8/1977 | Brunnett et al. | 364/414 |
| 4,064,393 | 12/1977 | Pasedach et al. | 364/414 |

OTHER PUBLICATIONS

The Siretom, A Computerized Transverse Axial Tomograph for Brain Scanning; K. Fuhrer, R. Liebetruth, G. Linke, K. Pauli, E. P. Ruhrnschopf & G. Schwierz, Electromedica, 2-3-75, pp. 48-55.
Computerized Tomographic Scanner, American Science & Engineering, Inc. Publ. No. ASE-3869, Apr. 1976.

Primary Examiner—Edward J. Wise
Attorney, Agent, or Firm—Hill, Gross, Simpson, Van Santen, Steadman, Chiara & Simpson

[57] ABSTRACT

A tomography processor system for processing data from a plurality of projections in essentially real time to produce a reconstructed image immediately following completion of a scan. The system includes specialized high-speed processing stages for performing required calculations and operating in concert with a low-cost computer providing overall system control. These processing stages form a multi-stage pipeline processor capable of performing the correction, convolution, interpolation, and back projection functions required to reconstruct the desired final image. The invention makes use of a reconstruction algorithm particularly adapted to implementation in the manner disclosed and claimed.

68 Claims, 28 Drawing Figures

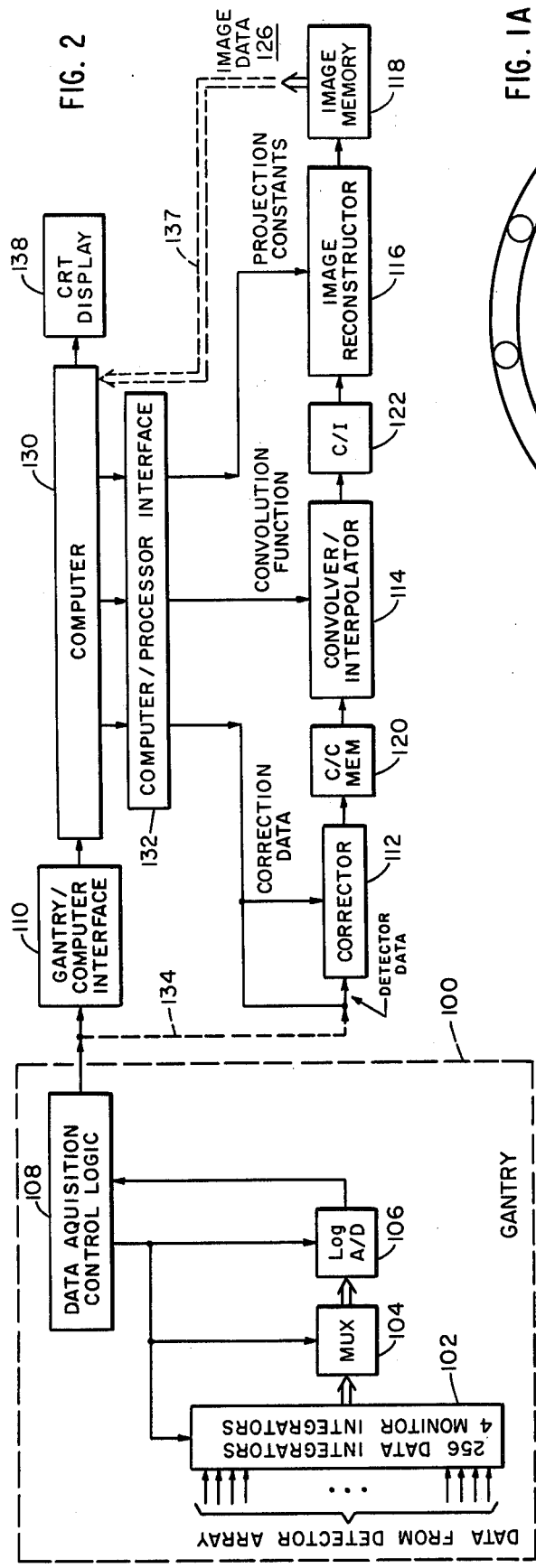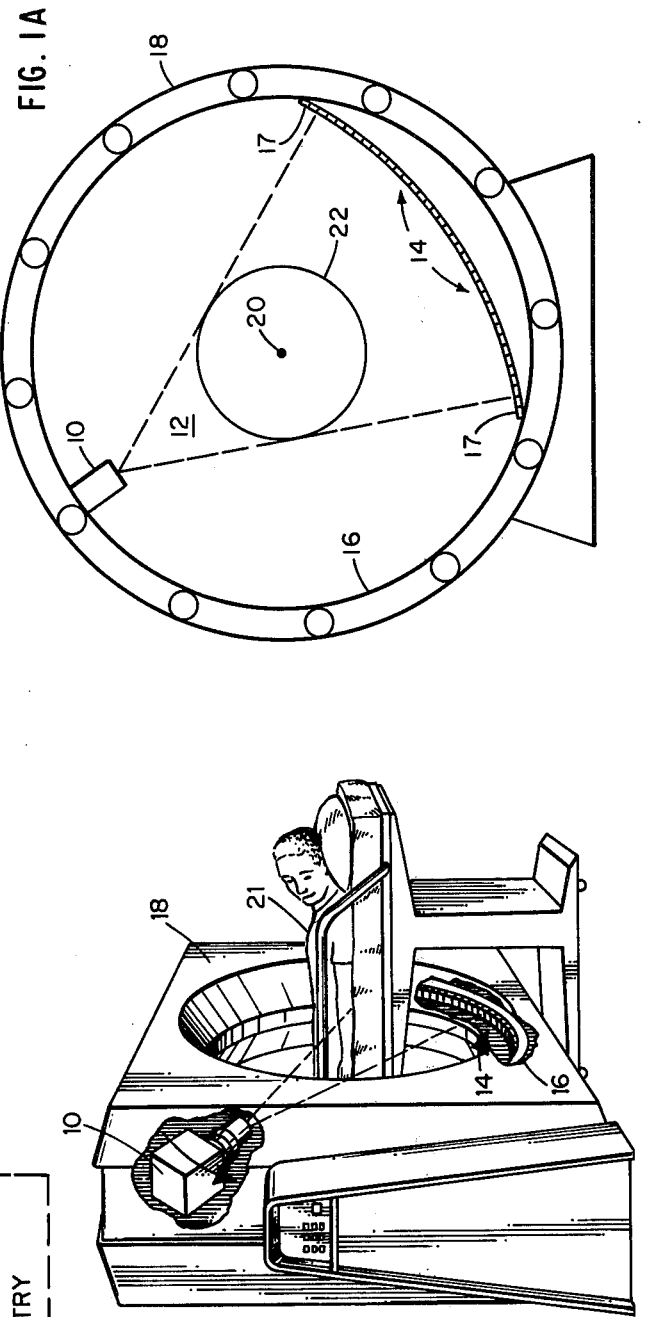

TOMOGRAPHY SIGNAL PROCESSING SYSTEM

FIELD OF THE INVENTION

This invention relates to tomography and more particularly to tomography systems for providing a plurality of projections of a body and processing circuitry for reconstructing an image from data derived from such projections.

BACKGROUND OF THE INVENTION

The development of mathematical procedures for the reconstruction of images of the internal structure of a body has been under consideration since the beginning of this century. In general, tomography systems include a radiation source arranged to direct x-ray or other radiation through a portion of a body and one or more sensors disposed to receive radiation passing through the body which provide a signal representative of received radiation intensity. The source and associated sensors are movable relative to the body to provide a plurality of projections during a predetermined scan to produce data from the several projections. Various techniques of image reconstruction have been proposed by which data from the projections is assembled into a final image. Such techniques have employed iterative algebraic reconstruction, Fourier transformations, and convolution filtering.

During recent years, great interest has been shown in computerized tomography by which a digital computer is employed for image reconstruction. Present tomography systems generally employ costly, general purpose computers for the reconstruction processing, and these systems have not been wholly satisfactory for a number of reasons, including expense, limited resolution and the requirements of long periods of time following completion of a scan before a reconstructed image is produced. In order to accomplish the large number of complex calculations required for producing a final image, a sophisticated high-speed computer is required, but even with such a computer, considerable time is required for production of the final image.

Some tomography processing systems have employed separate, dedicated processors controlled by a central computer to perform one or more of the correction, convolution and image reconstruction functions. However, in these systems, the dedicated processors are independent of one another, and data is transferred between the dedicated processors via the central computer, which controls each of the processors and to which each of the dedicated processors is connected. This configuration reduces somewhat the complexity required of the computer; but the speed of the system is restricted by the input/output speed of the computer, and for a high-speed system, an expensive high-speed computer is still required.

In order to reduce the time required to produce a final image or to reduce the sophistication required of the computer, approximations have been made in the algorithms implemented by the above-described system to reduce computing time. However, these approximations have resulted in less than optimum imaging results.

SUMMARY OF THE INVENTION

The present invention provides a tomography system for processing data from a plurality of projections in essentially real time to produce a reconstructed image immediately following completion of a scan. The system includes specialized high-speed processing stages for performing required calculations and operating in concert with a low-cost computer providing overall system control. These processing stages form a multistage pipeline processor capable of performing the correction, convolution, interpolation, and back projection functions required to reconstruct the desired final image. The invention makes use of a reconstruction algorithm particularly adapted to implementation in the manner disclosed and claimed.

Briefly, the data acquisition and processing system receives digitized data representing intensity of x-ray or other radiation incident on a detector array and performs certain corrections to produce corrected data representative of the integral of the density of a body through which the radiation has passed. The corrected data is then convolved with a deblurring function in preparation for the back projection operation. Next, data from each angular projection is preinterpolated, obviating the necessity for calculating interpolation values for each individual picture element (pixel) of the final image. A coordinate transformation is then performed which results in much simpler calculations being required during the back projection process. The back projection is performed by selection of proper data for each picture element of the final image and multiplication of this data by a weighting factor. In the transformed coordinate system, the selection and weighting processes are independent of projection angle. The final image is stored in an image having one memory location for each pixel. Each location in the image memory is augmented with the proper data during each projection, the final value being the sum of each of the data points produced during each projection. As the product of each located data point and weighting factor is produced, it is added to the value stored in the appropriate location in the image memory to produce the data representative of the final image.

The overall control of the system is carried out by a relatively simple and inexpensive control computer. Provisions are made for modifying the correction and convolution procedures by varying certain parameters via the control computer. In the preferred embodiment, a 256 × 256 picture element image is produced within a small fraction of a second following the completion of a five-second 360° scan.

DESCRIPTION OF THE DRAWINGS

FIGS. 1 and 1A show the tomographic scanner, gantry, x-ray source and detector array;

FIG. 2 is a block diagram of the tomographic processor;

FIG. 7A is a sketch of a typical deblurring function;

DETAILED DESCRIPTION OF THE PREFERRED EMBODIMENT

Overall System Description

Figure 3A:
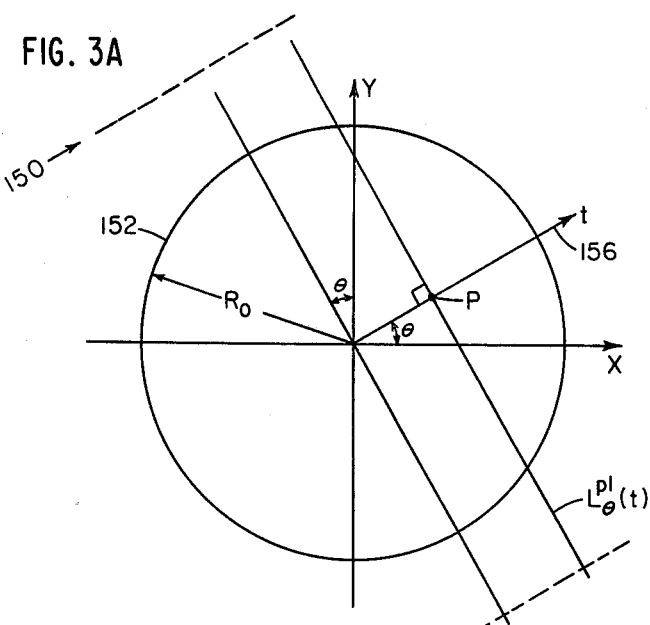
FIGS. 3A–3E are drawings helpful in explaining the mathematical algorithm by which the final image is reconstructed.

Before discussing the present invention in detail, a discussion of the entire tomography system, including a brief summary of the functions carried out by each of the major sections of the processor, will be helpful. FIGS. 1 and 1A show the mechanical portion of the system which exposes the patient to x-rays, and FIG. 2 is a block diagram showing the major sections of the processor electronics.

An x-ray tube 10 or other source of radiation projects a fan-shaped beam 12 of x-rays which impinge upon a detector array 14. The detector array 14 is composed of a linear array of a plurality of detectors. The detectors are circumferentially located along a circle whose center is located at the x-ray source 10. In the preferred embodiment, there are 256 data detectors which provide data used in forming the final image and four monitor detectors 17, two on each end of the detector array, which receive unattenuated radiation from x-ray source 10, as described below. This can be seen in FIG. 1, which shows the x-ray exposure mechanism and in FIG. 1A which is a diagrammatic illustration of this mechanism.

X-ray source 10 and detector array 14 are mounted on an inner ring 16 of a gantry structure, such that the x-ray source 10 and the detector array 14 are held in a fixed relationship to one another. The inner ring 16 is rotatably mounted in an outer ring 18 such that the inner ring 16 may be rotated, revolving x-ray source 10 and detector array 14 about an axis 20 perpendicular to the plane of fan-beam 12. This causes the fan-beam 12 to illumintate a circular area defined by line 22 as the inner ring 16 of the gantry is rotated through 360 degrees, the angle of the x-ray illumination changing as the x-ray source 10 and detector array 14 are rotated. The body 21 being scanned is placed within circular area 22 and x-rays passing through area 22 impinge upon the 256 data detectors in detector array 14. The monitor detectors 17 are located so that x-rays impinging on the monitor detectors pass outside of the area 22. Thus, the x-rays impinging upon the monitor detectors provide an indication of the x-ray intensity from x-ray source 10 for each projection.

The angle of illumination by x-ray source 10 of area 22 with respect to the stationary body 21 is called the projection angle. By taking data from the data detectors in array 14 at a plurality of different projection angles, a tomographic scan of a patient or other object placed in area 22 may be taken, and by processing the data from detectors 14, a picture may be formed representative of the density of a patient or other object in the cross-section area lying in the plane of fan-beam 12.

The above-described process is carried out many times as the x-ray source and detector are revolved about the stationary patient. In the preferred embodiment described herein, the gantry performs one complete revolution in approximately five seconds. One exposure of the patient is taken for each one degree of rotation, producing 360 separate sets of data from each of the 256 data detectors and four monitor detectors. This data is processed to produce the final picture, as described below.

Referring to FIG. 2, the processing electronics are divided up into two sections. The first section includes the data acquisition electronics and is located on the gantry so as to rotate with the detector array and x-ray source. The other section includes the remainder of the processing electronics which is usually stationary and not located on the gantry. The data acquisition electronics, shown within dotted box 100 in FIG. 2, should be located as closely as possible to the detector array 14 to minimize noise pick-up and other error sources.

The output from each detector in array 14 is applied to an associated integrator 102. There are 256 data integrators and four monitor detector integrators. The outputs from each of the integrators are applied to a multichannel analog multiplexer 104. Multiplexer 104 selectively applies the integrator outputs to logarithmic analog-to-digital conversion circuitry 106. Integrators 102, multiplexer 104, and A/D conversion circuitry 106 are controlled by signals from data acquisition control logic 108. The digital data from conversion circuitry 106 representing the detector outputs is applied to data acquisition control logic 108 which transmits this data along a cable connecting the gantry electronics 100 with the remainder of the tomography processor.

After the data from each of the detectors has been put into digital form and transmitted from gantry 100, the several operations which must be carried out on this data to form the final image are performed in a high-speed, dedicated, pipeline processor. The pipeline processor is composed of four major stages: a corrector 112, a convolver/interpolator 114, an image reconstructor 116, and an image memory 118. The detailed circuitry of each of these stages is described in the following sections, and several of these stages have an internal pipeline processing configuration. By performing the necessary calculations step by step in each of the pipeline stages, the processor is able to perform these functions in real time as the data is taken during the scan.

In the preferred embodiment, the data from gantry 100 is applied to gantry/computer interface circuitry 110. This circuitry causes the data from gantry 100 to be properly formatted and stores it in the memory of a control computer 130 via direct memory access (DMA). One computer suitable for use with the present invention is a Digital Equipment Corporation PDP-11. When the corrector 112 is ready for new data, this data is applied to corrector 112 from computer 130 via computer/processor interface circuitry 132 and stored in the corrector 112 for processing. The data transfer from gantry 100 to corrector 112 is done via the computer to facilitate storage of raw data, if desired, and also to allow calibration computations to be performed by the computer in response to calibration data taken as described below. In other embodiments where it may be undesirable to have the data from gantry 100 go through the memory of computer 130, the data from the gantry may be applied directly to corrector 112 as shown by dotted line 134.

The data applied to corrector 112 consists of digital values representative of the logarithm of the detector outputs. The corrector performs several different operations upon the data. In order to take out variations in detector sensitivity and channel gain, offsets in the electronics and variations in x-ray intensity from projection to projection, data is taken with no object between x-ray source 10 and detector array 14. From this data, the computer calculates calibration values which are stored and later applied to the corrector via interface 132. Also, the detector output data is not a linear function of the density of the body through which the x-rays pass, due to beam-hardening effects; and a beam-hardening correction is performed by corrector 36. Lastly, the detector output is multiplied by the cosine of the angle of the particular detector, with respect to the central detector. This is necessary due to the mathematical function relating the measured data with the final image, as explained in detail in the following mathematical description.

The corrected data is stored in the C/C memory as it is calculated. After all the data from one projection has been corrected and stored in C/C memory, it becomes available for processing by convolver 114. The convolver convolves the series of corrected data points with a deblurring function to prepare the data for back projection. The convolution function may be varied by an operator, depending on the characteristics which it is desired to enhance in the final image. To accomplish this, computer 130 has a plurality of deblurring functions stored therein. In response to the selection of one of these functions by an operator, computer 130 transfers data representative of this function to the convolver via interface 132. This is done offline, prior to beginning a tomographic scan. The deblurring function transferred from the computer to convolver consists of 256 words of 24 bits each.

The output from the convolver consists of 256 data points. The interpolator takes this information and provides eight points of interpolated data from each of the 256 data points. This is done by providing seven additional data points between each of the original data points. These additional data points are calculated by linearly interpolating between each of the original data points.

The interpolated and convolved data is stored in C/I memory 122, where it becomes available to the image reconstructor 116 which back-projects the data from each of the exposures into image memory 118 to provide the final picture. The present invention utilizes a unique method of performing the back projection which allows a high-speed pipeline processor to perform the back projection calculations in essentially real time, so that the final image is presented immediately following the scan.

The image reconstructor requires that certain constants be stored or calculated prior to performing the image reconstuction computations for each scan. Typically, these projection constants are most conveniently stored in or calculated by computer 130 and then transferred to image reconstructor 116.

During each projection, for each of the 64K points in the 256 × 256 image array, the image reconstructor determines the corresponding data and multiplies it by a weighting function. The output from image reconstructor 116 during each projection is 64K words. These values are added to the partial image data previously stored in an image memory 118. The image memory is made up of 64 K words of 16 bits each. After a scan has been completed, the data stored in image memory 118 is representative of the density of the cross-sectional area being scanned.

The image data 126 from image memory 118 may be displayed in various ways. In the preferred embodiment, this data is read by computer 130, as shown by dotted line 137, where certain functions may be performed on this data by the computer, for example, to compress or enlarge the dynamic range of the gray scale in the image The computer then applies the processed data to a CRT or other type of display 138.

Data is transferred between the corrector, convolver/interpolator, and image reconstructor stages of the pipeline processor by means of two, two-bank memories. Between the corrector and the convolver/interpolator is a corrector/convolver or C/C memory 120. While corrector 112 is writing corrected data from one projection in one bank of C/C memory 120, the convolver is reading data from the previous projection from the other bank of C/C memory 120. During each scan, 256 words of 15 bits each are written into or read from each bank of C/C memory 120. Between the convolver/interpolator 114 and the image reconstructor 116 is a convolver/image reconstructor or C/I memory 122. The C/I memory is a two-bank memory similar to the C/C memory. The interpolator produces eight intermediate values for each convolved data point and the 18 most significant bits of the result of each convolution and interpolation are retained. thus, 2,048 words of 18 bits are written into and read from each of the two memory banks of C/I memory 112 during each projection.

Mathematical Background

The following is a brief description of the mathematical background on which the tomography processor is based. This derivation does not deal with all the technical mathematical problems involved, but rather is intended to show the source of the key terms and factors required by the processor. A more detailed and rigorous formulation may be derived from the description below by one of ordinary skill in the art. To derive the fan-beam reconstruction formula, a parallel beam reconstruction formula is first given and then it is shown how the fan-beam reconstruction formula can be derived therefrom by a change of variables. A digital implementation of this formula is then described.

Referring to FIG. 3A, the terminology used in the parallel beam reconstruction formula is explained. The x-ray source of a parallel beam system would be located as shown by dotted line 150. Rays emitted therefrom in parallel would pass through an object located within circle 152 having a radius $R_0$ and impinge upon a detector array located as shown by dotted line 154. The density of the object within circle 152 is given by $F(x,y)$, and $F(x,y)$ is zero for all areas outside of circle 152. For a point P located within circle 152 and having coordinates (x,y), consider a ray 156 from the origin passing through point P. The angle that this ray makes with the x-axis is denoted as $\theta$, and the distance from the origin to point P is denoted as t. Let $L_\theta^{p1}(t)$ denote the line perpendicular to line 156 passing through the origin at point P. (The superscript "p1" refers to the fact that for fixed $\theta$, the collection of lines defined as t is varied are all parallel, as opposed to the divergent family of lines to be discussed below.) The line integral of F(x,y) along $L_\theta^{p1}(t)$ is denoted as $l_\theta^{p1}(t)$. In a parallel-beam tomography system, the angle $\theta$ is the projection angle; and the line integral $l_\theta^{p1}(t)$ is the integral of the density, or x-ray absorption, along line $L_\theta^{p1}(t)$ of the object being scanned, which is inversely proportional to the exponential of the line integral of the density.

If $l_\theta^{p1}(t)$ is measured for t between $-R_0$ and $+R_0$ and all $\theta$, then F(x,y) may be determined from the following equation, which may be derived from line integral equations previously determined by Radon in "Uber die bestimmung con Funktion durch ihre integralwerte langs gewisser Mannisaltigkeiten," *Berichte Sachsische Akademic der Wissenschaften (Leipzig).* Mathematische-Physische Klasse 69; (1917), 262.

$$F(x,y) = \frac{1}{4\pi^2} \int_0^{2\pi} d\theta \left[ \int_{-R_o}^{R_o} \frac{2 l_\theta^l(t_\theta) - l_\theta^l(t_\theta + t) - l_\theta^l(t_\theta - t)}{t^2} dt \right] \quad (1)$$

where:

$$t\theta = X\cos\theta + Y\sin\theta \quad (2)$$

or in more complicated but more useful form:

$$F(x,y) = \frac{1}{4\pi^2} \int_0^{2\pi} d\theta \lim_{\epsilon \to 0} \left[ - \int_{-R_o}^{t_\theta - \epsilon} \frac{l_\theta^l(t) dt}{(t - t_\theta)^2} + \frac{2 l_\theta^l(t_\theta)}{\epsilon} - \int_{t_\theta + \epsilon}^{R_o} \frac{l_\theta^l(t) dt}{(t - t_\theta)^2} \right] \quad (3)$$

Figure 3B:
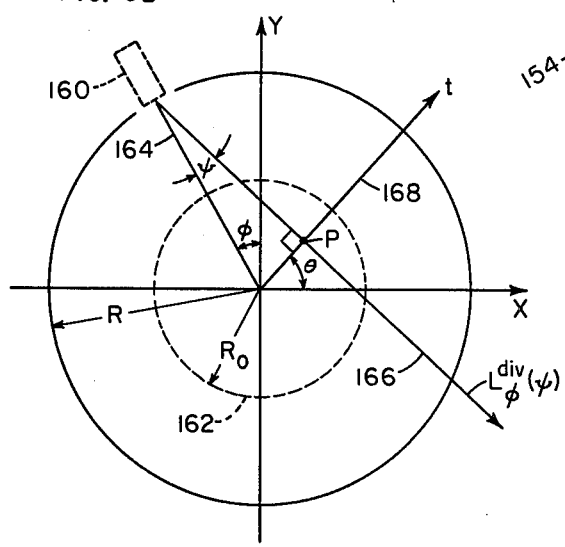

Referring to FIG. 3B, the terminology used in a divergent beam system is explained. Here, the x-ray source 160 emitting a fan-beam of x-rays moves along a circle of radius R, while the object being scanned lies within a circle 162 of radius $R_0$ where $R_0 \leq R/2$. The projection angle is denoted by $\phi$ and equals the angle between the positive Y axis and the "center" ray 164 which is emitted by x-ray source 160 and passes through the origin. The detector angle is denoted by $\psi$ and is the angle between the detector and center ray 164. For a fixed projection angle $\phi$, a line going through x-ray source 160 and which makes an angle $\psi$ with the center line is denoted as $L_\phi^{div}(\psi)$. Thus, $L_\phi^{div}(\psi)$ denotes a line or x-ray emitted from the x-ray source 160 and impinging upon a detector at angle $\psi$ for a projection angle $\phi$. The line integral of F(x,y) along line $L_\phi^{div}(\psi)$ is denoted as $l_\phi^{div}(\psi)$. As explained above, the x-ray intensity measured by a detector is inversely proportional to the exponential of the line integral of the density of the object being measured.

If the line $L_\phi^{div}(\psi)$ is defined to denote the same line as $L_\theta^{p1}(t)$, the following transformation can be made. The line 168 perpendicular to the line 166, $L_\phi^{div}(\psi)$, and passing through the origin is at the angle $\theta$ with the positive x-axis. Point P is the intersection of lines 166 and 168, and the distance from the origin to point P is t.

From FIG. 3B, the following change of variables from the parallel beam case of FIG. 3A to the divergent beam case of FIG. 3B can be made according to the following formulas:

$$\psi = \arcsin(t/R) \quad (4a)$$

$$\theta = \phi + \psi \quad (4b)$$

$$t = R \sin \psi \quad (4c)$$

$$\phi = \theta - \arcsin(t/R) \quad (4d)$$

where, as defined above:

$$L_\phi^{div}(\psi) = L_\theta^{p1}(t) \quad (5)$$

Under this change of variables, the integrals in equations (2) and (3) become:

$$\int_0^{2\pi} d\theta \int_{-R}^{R} dt = \int_{-\pi/2}^{\pi/2} d\psi \int_0^{2\pi} d\phi \cos\psi \quad (6)$$

Figure 3C:
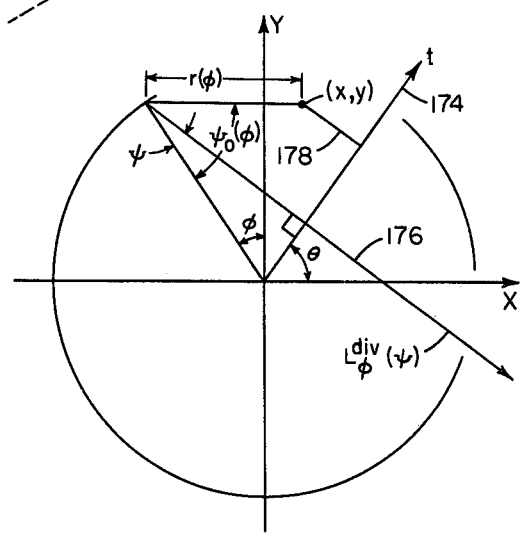

There remains the value $t_\theta$ in equations (1)-(3) be defined in terms of divergent beam variables. Referring to FIG. 3C, for a detector angle $\psi$, a projection angle $\phi$ and an arbitrary point (x,y), $r(\phi)$ is defined to be the distance of the fixed point (x,y) from the x-ray source for that projection angle. $\psi_o(\phi)$ is the angle between the center ray and a ray passing through point (x,y); i.e., $\psi_o(\phi)$ is the detector angle of the ray passing through point (x,y) for a projection angle $\phi$. The ray 176 defined by $\phi$ and $\psi$ is denoted by $L_\phi^{div}(\psi)$, as explained above. Ray 174 from the origin making an angle $\theta$ with the x-axis is perpendicular to ray 176. Then, from FIG. 3C, it can be seen that the unique line 178 $L_\theta^{p1}(t_\theta)$ passing through (x,y) and perpendicular to ray 176 is determined by:

$$t_\theta = R\sin\psi + r(\phi)\sin(\psi_o(\phi) - \psi) \quad (7)$$

There are two types of integrand terms in equations (2) and (3) whose variables must be changed. These are:

$$\frac{1}{(t - t_\theta)^2} \quad (8)$$

and $$l_\theta^l(t) \quad (9)$$

Using the formulas in equation (4c) for t and equation (7) for $t_\theta$, expression (8) in the parallel beam case may be replaced in the fan-beam case by:

$$(t - t_\theta) = r(\phi) \sin(\psi - \psi(\phi)) \quad (10)$$

Since $L_\phi^{div}(\psi)$ is defined to be the same line as $L_\theta^{p1}(t)$ in equation (5), the integrals of F(x,y) along these lines must also be equal, and expression (9) is quickly transformed when $\phi$ and $\psi$ are related to t and $\theta$ according to equations (4), by:

$$I_\theta^{p1}(t) = I_\phi^{div}(\psi) \tag{11}$$

Combining equations (3), (6), (9), and (11), the result is:

$$F(x,y) = \tag{12}$$

$$\frac{R}{4\pi^2} \int_0^{2\pi} d\phi \lim_{\epsilon \to 0} \left[ -\int_{-\pi/2}^{\psi_o(\phi) - \epsilon} \frac{I_\phi^{div}(\psi)\cos\psi d\psi}{[r(\phi)\sin(\psi - \psi_o(\phi))]^2} + \frac{2I_\phi^{div}[\psi_o(\phi)]\cos\psi(\phi)}{r(\phi)^2 \sin\epsilon} - \int_{\psi_\phi + \epsilon}^{\pi/2} \frac{I_\phi^{div}(\psi)\cos\psi d\psi}{[r(\phi)\sin(\psi - \psi_o(\phi))]^2} \right]$$

The change in limits may be easily verified by inspection.

Equation (12) is expressed in terms of continuously variable projection and detector angles, $\phi$ and $\psi$. The following derivation shows how equation (12) is applied to the present system where a limited number of individual detectors are employed and projections are taken at discrete angular intervals.

Abbreviating the limit in equation (12) by $L'(\psi_o(\phi),\phi)$, the integral over $\phi$, the projection angle, is approximated by:

$$F(x,y) \approx \frac{R}{4\pi^2} \sum_{n=1}^{N} \frac{2\pi}{N} \left[ \frac{1}{r(\phi_n)} \right]^2 L'(\psi_o(\phi_n),\phi_n) \tag{13}$$

where $\phi_n = n2\pi/N$ for integral n, N equals the number of individual projections per 360 degree scan, and $\phi_n$ is the projection angle of the nth projection. Note also that for a fixed $\phi$ (or $\phi_n$), the $[1/r(\phi)]^2$ factor within the limit function of equation (12) becomes a constant which may be taken outside the limit function L' as done in equation (13).

Figure 3D:
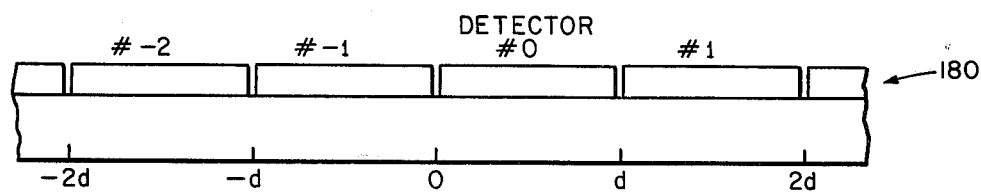

Next, the value of the limit L' in equation (13) is evaluated for a discrete detector array and for a fixed projection angle $\phi_n$. Referring to FIG. 3D, part of a detector array 180 is shown. The intersection of the central ray from the x-ray source with the detector array is at zero, and there are L detectors to the right of zero and L detectors to the left of zero. The angular spacing between detectors is $\delta$. Thus, the mth detector has its left end at angle m·$\delta$ and the center of the mth detector is at $(m + \frac{1}{2})\delta$.

The output of each detector is actually the sum of x-ray intensities over a finite angle $\psi$ to $\psi + \delta$, rather than at a single angle $\delta$; and the assumption is made the output of the mth detector is proportional to the line integral along a line intersecting the middle of the detector $(m + \frac{1}{2})\delta$. To find $L'(\psi_o(\phi_n),\phi_n)$ the L' function is evaluated at $\psi_o(\phi_n) = (k + \frac{1}{2})\delta$ for integral values of k, which is the value of the L' function at the center of each detector. The value of L' for $\psi_o(\phi_n)$ equal to values other than detector centers (i.e. for non-integral k) is found by interpolation. (For a more detailed explanation of why $\psi_o(\phi_n)$ is not always equal to $(k+\frac{1}{2})\delta$, see FIGS. 9 and 10 and the corresponding discussion below.)

To evaluate L' for $((k + \frac{1}{2})\delta, \phi_n)$, which is the value of the convolved function at the center of the kth detector, the limit L' in equation (12) may be broken up into three terms, as shown below:

$$1. - \int_{-\pi/2}^{k \cdot \delta} d\psi \frac{I_\phi^{div}(\psi)\cos\psi}{\sin^2(\psi - \psi_o(\phi))} \tag{14a}$$

$$2. - \int_{k\delta}^{(k+\frac{1}{2})\delta - \epsilon} d\psi \frac{I_\phi^{div}(\psi)\cos\psi}{\sin^2(\psi - \psi_o(\phi))} + \frac{2I_\phi^{div}[\psi_o(\phi)]\cos\psi(\phi)}{\sin \epsilon} \tag{14b}$$

$$- \int_{(k+\frac{1}{2})\delta+\epsilon}^{(k+1)\delta} d\psi \frac{I_\phi^{div}(\psi)\cos\psi}{\sin^2(\psi - \psi_o(\phi))}$$

$$3. - \int_{(k+1)\delta}^{\pi/2} d\psi \frac{I_\phi^{div}(\psi)\cos\psi}{\sin^2(\psi - \psi_o(\phi))} \tag{14c}$$

Figure 3E:
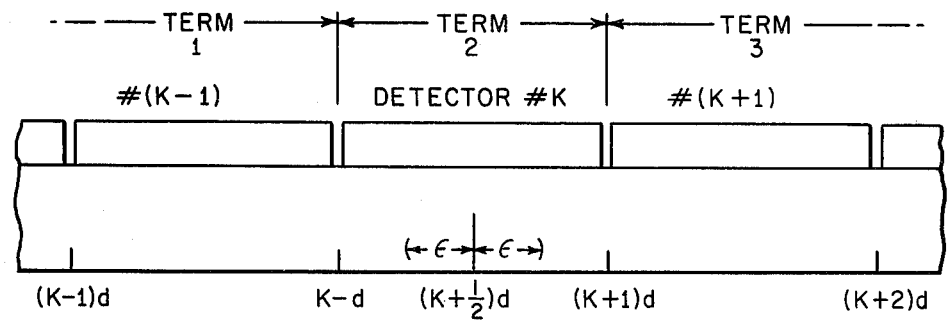

These terms denote the integrals over the respective areas of the detector array as shown in FIG. 3E.

The first term of equation (14) may be further broken down as shown below:

$$\int_{-\pi/2}^{k \cdot \delta} d\psi \frac{I_\phi^{div}(\psi)\cos\psi}{\sin^2(\psi - \psi_o(\phi))} = \tag{15}$$

$$-\sum_{m=-L}^{k-1} \int_{m \cdot \delta}^{(m+1)\delta} d\psi \frac{I_\phi^{div}(\psi)\cos\psi}{\sin^2(\psi - \psi_o(\phi))}$$

Asssuming that the numerator does not vary as rapidly as the denominator in equation (15), it is assigned the value at the center of the detector and removed from the integral, to give the following approximation:

$$\approx I_\phi^{div}[(m + \frac{1}{2})\delta]\cos[(m + \frac{1}{2})\delta] \int_{m\delta}^{(m+1)\delta} d\psi \frac{-1}{\sin^2(\psi - \psi_o(\phi))} \tag{16}$$

Note that the value of the term brought outside the integral is line integral of the x-rays impinging upon the mth detector multiplied by the cosine of the detector angle of the mth detector for a projection angle $\phi$. This value (which is the output from corrector 112 of the tomography processor) shall be denoted as $A_\phi(m)$ where:

$$A_\phi(m) = I_\phi^{div}[(m+\frac{1}{2})\delta]\cos[(m+\frac{1}{2})\delta] \tag{17}$$

Next, the integral in equation (16) is evaluated:

$$\int_{m\delta}^{(m+1)\delta} \frac{-1}{\sin^2(\psi - \psi_o(\phi))} d\psi = \tag{18}$$

$$\cot[(k - m + \frac{1}{2})\delta] - \cot[(k - m - \frac{1}{2})\delta]$$

where $\psi_o(\phi) = (k + \frac{1}{2})\delta$. The function given by equation (18) is the deblurring function, and for simplicity, the value of the deblurring function in equation (18) shall be denoted as $C(k-m)$, where:

$$C(s) = \cot(S+\frac{1}{2})\delta - \cot(S-\frac{1}{2})\delta \tag{19}$$

Thus, term (14a) may be approximated as:

$$\sum_{m=-L}^{k-1} A_\phi(m) \times C(k - m) \tag{20}$$

An identical derivation may be performed from term (14c), the only difference being a change of limits. Thus, the sum of terms (14a) and (14c) yield:

$$\sum_{\substack{m=-L \\ m \neq k}}^{L-1} A_\phi(m) \times C(k-m) \quad (21)$$

It can be shown that expression (14b) yields the term m=k in the summation of equation (21). Thus, for the kth detector, the value of the function L' may be approximated by:

$$L'((k+\tfrac{1}{2})d,\phi) \sim \sum_{m=-L}^{L-1} A_\phi(m) \times C(k-m) \quad (22)$$

where $A_\phi(m)$ is given by equation (18) and C(k-m) is given by equation (19).

From equations (13) and (22), the final reconstruction algorithm is given by:

$$F(x,y) \sim \frac{R}{2\pi N} \sum_{n=1}^{N} \left[\frac{1}{r(\phi_n)}\right]^2 L^1(\psi_o(\phi_n),\phi_n) \quad (23)$$

where $L'(\psi(\phi_n),\phi_n)$ is obtained by interpolating between the discrete values of L' given by equation (22). This process is carried out in the image reconstructor 118. For each projection angle $\phi_n$, the summation of equation (23) is carried out by multiplying the corresponding convolved data L' from convolver/interpolator 114 by $[1/r(\phi_n)]^2$ and adding this value to the value previously accumulated in the proper location (x,y) in image memory. This is performed for all locations in image memory for each projection angle.

Data Acquistion Electronics

The 256 detectors in detector array 14 are each connected to an associated integrator. This is shown in block diagram form in FIG. 4A where the output from one of the detectors 200 in detector array 14 is applied to a reset integrator 202. An integrator control signal resets integrator 202 prior to each pulse from x-ray source 10. During the time that the patient is exposed to the fan-beam of x-rays, the output from detector 200 is integrated by integrator 202. The output from integrator 200 is applied to multiplexing circuitry which is shown in FIG. 4 and is described below.

After an x-ray exposure is finished, the integrated detector output in each of the integrators is sequentially read by the multiplexer circuitry. After the integrators have been read, the integrator control signal resets the integrators prior to the next x-ray pulse from x-ray source 10. Typically, there is an interval between the time when the last data is read from the reset integrators 202 and the next x-ray pulse begins. The accuracy of the tomography system may be increased by using this interval for auto-zeroing the reset integrators. This is described in more detail below.

Figures 4, 4A:
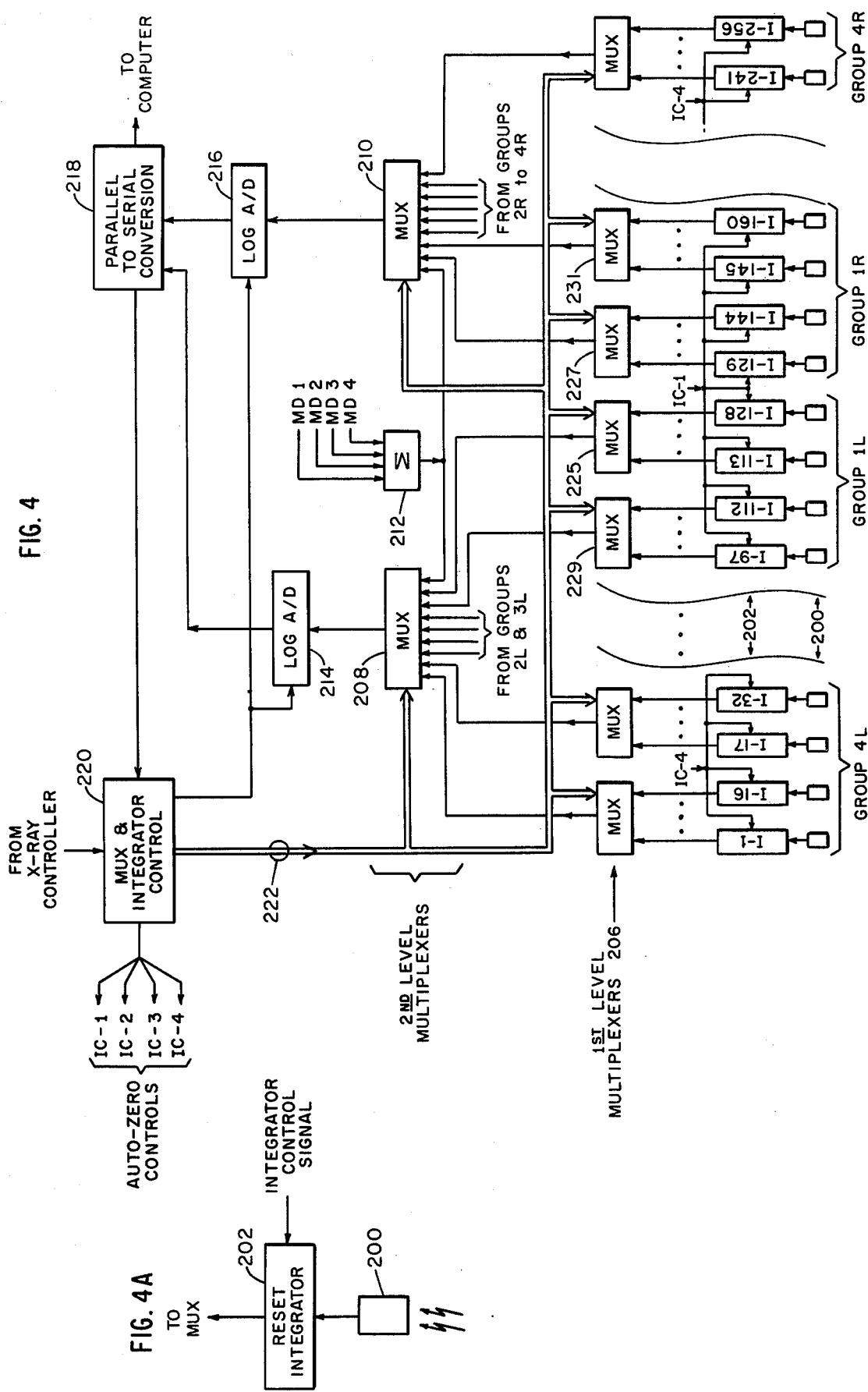
FIGS. 4 and 4A show the data acquisition circuitry.

FIG. 4 shows the data acquisition circuitry which multiplexes and processes the data from each of the reset integrators 202. Detector array 14 is divided into two equal sections, a right section and a left section. Each of these two sections is further divided into four groups, and these groups will be designated as 1-L, 2-L through 4-L for the left-hand section and 1-R through 4-R for the right-hand section. Each of these eight groups is composed of 32 detectors to make up the 256 detector array 14. The first groups in each of the right and left-hand sections, group 1-L and group 1-R, are located on either side of the center of detector array 14, and succeeding groups 2-L, 2-R, etc. progress out from the center of detector array 14 with groups 4-L and 4-R being respectively on the left and right edges of the detector array, excluding the monitor detectors. The reason for this ordering is explained below.

Each of the outputs from each of the reset integrators 202 is applied to a series of multiplexers which sequentially apply each of these outputs to two, logarithmic analog-to-digital converters. This multiplexing operation is performed in two levels. In the first level, the 128 individual outputs from each of the right and left-hand sections are converted to eight signals for each section; and in the second level, two 9-to-1 multiplexers select one from among these eight signals and a signal from the monitor detectors. Each of these outputs is applied to a logarithmic A/D converter which produces a digital representation of the inverse of the logarithm of the signal.

The first-level multiplexers 206 receive the signals from each of the reset integrators 202 associated with each detector. In the preferred embodiment shown in FIG. 4, the first-level multiplexers are made up of 16, 16-channel multiplexers 206. The eight outputs from the left section multiplexers are applied to a second-level multiplexer 208. Similarly, the eight first-level multiplexers 206 receiving signals from the right section integrators have their outputs applied to a second-level multiplexer 210. The four outputs from the four monitor detector integrators, denoted by MD1-MD4, are applied to a summation circuit 212 where they are combined to provide a signal representative of the average intensity of x-rays impinging upon the monitoring detectors. The output from summation circuit 212 is applied to both left section, second-level multiplexer 208 and right section, second-level multiplexer 210. Second-level multiplexers 208 and 210 each select one output signal from the nine input signals.

The output from each of the second-level multiplexers 208 and 210 are applied to two logarithmic A/D converters 214 and 216. Each of these converters transforms the successive analog signals applied thereto by the multiplexer structure described above into a 15-bit digital representation of the logarithm of the analog value of the signal; and this value is inverted to give an output proportional to the attenuation, since the x-ray intensity measured by the detectors is inversely proportional to the density, or attenuation, of the body which the x-rays pass through. One logarithmic A/D converter particularly suitable for use in the present invention is an Analogic Model AN8020L converter. Other types of logarithmic converters may be used, however.

The digital outputs of the two logarithmic converters 214 and 216 are applied to output parallel-to-serial conversion circuitry 218. Due to the movement of the gantry containing detector array 14 and the data acquisition circuitry, communication of signals from the rotating gantry to the remainder of the signal processing circuitry, which is stationary, involves the use of slip rings, retractable cables, or other means for allowing the signals to be transmitted as the gantry revolves. For this reason, it is desirable to keep the number of actual signal lines to a minimum. Converter 218 takes the digital data from each of the logarithmic A/D converters 214 and 216 and transforms this data into a single stream of serial data which is transmitted over a single cable from the gantry to the computer 120 and the remainder of the signal processing electronics.

The operation of the above-described data acquisition circuitry is controlled by a multiplexer and integrator control circuit 220. Control circuit 220 produces four integrator control signals, designated as IC-1 through IC-4. Each of these integrator control signals is applied to the corresponding left and right groups, such that groups 1-L and 1-R are controlled by IC-1; groups 2-L and 2-R are controlled by IC-2, and so forth. The integrator control signals select whether the integrators are in integration mode, wherein the output from the associated detector 200 is integrated, or in auto-zero mode, wherein the integrator is reset to zero and auto-zero circuitry is activated which compensates for drifts, offsets and other errors in the integrator. Control circuit 220 also applies the appropriate signals 222 to the first and second level multiplexers to cause them to apply the integrator output signals to the A/D converters 214 and 216, as described below.

The x-ray source 10 produces a pulse signifying the occurrence of each x-ray exposure. The leading edge of this pulse precedes the start of the x-ray exposure, and in response to the pulse, control circuit 220 switches each of the integrators 202 from auto-zero mode to integrate mode via the integrator control signals. Following this, x-ray source 10 produces a pulse of x-rays approximately two milliseconds long. The pulse from the x-ray controller then ends, denoting that the x-ray exposure has been completed; and multiplexer and integrator control 220 then causes the output signals from detectors 202 to be processed in the following manner.

First, control circuit 220 causes second-level multiplexers 208 and 210 to select the output from the group 1-L and 1-R first-level multiplexers, respectively. Control circuit 220 then causes group 1-L and 1-R multiplexers 225 and 227 to sequentially select the outputs from integrators I-97 through I-128, and I-129 through I-160, respectively. As each of these integrators is selected and the signals applied to the appropriate converter 214 or 216 by second-level multiplexers 208 and 210, the signals therefrom are converted into digital form and transmitted to the memory of computer 120.

When each of the integrators in groups 1-L and 1-R have been read, integrator control signal IC-1 goes low, causing the group 1-L and 1-R integrators to reset and begin an auto-zero cycle. Next, multiplexers 229 and 231 are enabled, selecting the signals from the integrators in groups 2-L and 2-R for conversion. When all of the integrators in groups 2-L and 2-R have been read, integrator control signal IC-2 goes low, causing these integrators to begin an auto-zero cycle. This process is repeated until each of the integrators has been read and the digital data corresponding thereto has been transmitted to computer 120.

After the data from the data detectors has been converted, second-level multiplexers 208 and 210 apply the output signal from summation circuit 212 and the monitor detectors and integrators to the A/D converters 214 and 216. A convert signal is applied to each of these converters by control circuit 220, and the digitized outputs from each of the converters are transmitted to computer 120 via parallel-to-serial converter circuit 218.

The above-described operation results in the detectors and integrators being read, beginning from the center of the detector array 14 and proceeding sequentially to the edges of the detector array. In spite of the most careful precautions, integrators 202 will invariably have some small errors resulting from offsets and drifts. Due to the nature of integrators, some of the components of these errors tend to increase with time. Detectors nearer the center of the detector array provide data, during the image reconstruction process, for more final image locations than do the detectors nearer the edges of the arrays. By reading the integrator outputs from detectors in the center of detector array first and proceeding outwards towards the edges, the integrator errors are minimized for more centrally located detectors, resulting in a clearer and sharper final image.

Corrector

The corrector takes the data from each individual detector, stored in logarithmetic form in computer 130, and performs mathematical operations on this data which correct for errors due to offsets in the electronics, differences in gain between detector channels arising from either variations in the detector sensitivities or errors in the electronics, and beam-hardening corrections. The corrector also multiplies the data by the cosine of the detector angle, as required by equation (18). To perform these corrections, the corrector accesses several data tables stored in computer 130. An offset table contains 256 words of offset data representing offset correction factors for the 256 detectors. A calibration correction table similarly contains 256 words of calibration correction factors. A beam-hardening correction table of 96 words contains data representative of a piece-wise-linear approximation to the beam-hardening correction function and finally, the detector data from the data acquisition electronics is stored in one of two data tables of 258 words each in the computer memory.

The offset correction data table and the calibration correction data table are determined by the tomographic system prior to performing a tomographic scan of a body to be examined. In the preferred embodiment, a complete scan of 360 projections is performed with no object or an object of a known, uniform density in the scanner. For each of the detectors, the outputs produced during each of the projections are summed and averaged. From this data, a calibration factor is determined for each detector accounting for differences in sensitivity between the detectors and differences in gain in the electronics of each detector channel. This calibration factor is normalized with respect to the x-ray intensity from x-ray source 10 by dividing the averaged outputs from each of the image detectors by the averaged outputs of the monitor detectors to provide the actual value of the correction factor.

The offset calibration is carried out by applying a precision bias to the input of each of the integrators 202 in place of the detector output. The detector output in response to the known precision input is processed to provide a measurement of the offset error, which may be positive or negative, in the electronics associated with that detector. This offset error is stored in an offset calibration table and used to correct the data taken during a tomographic scan, as described below.

Figure 5:
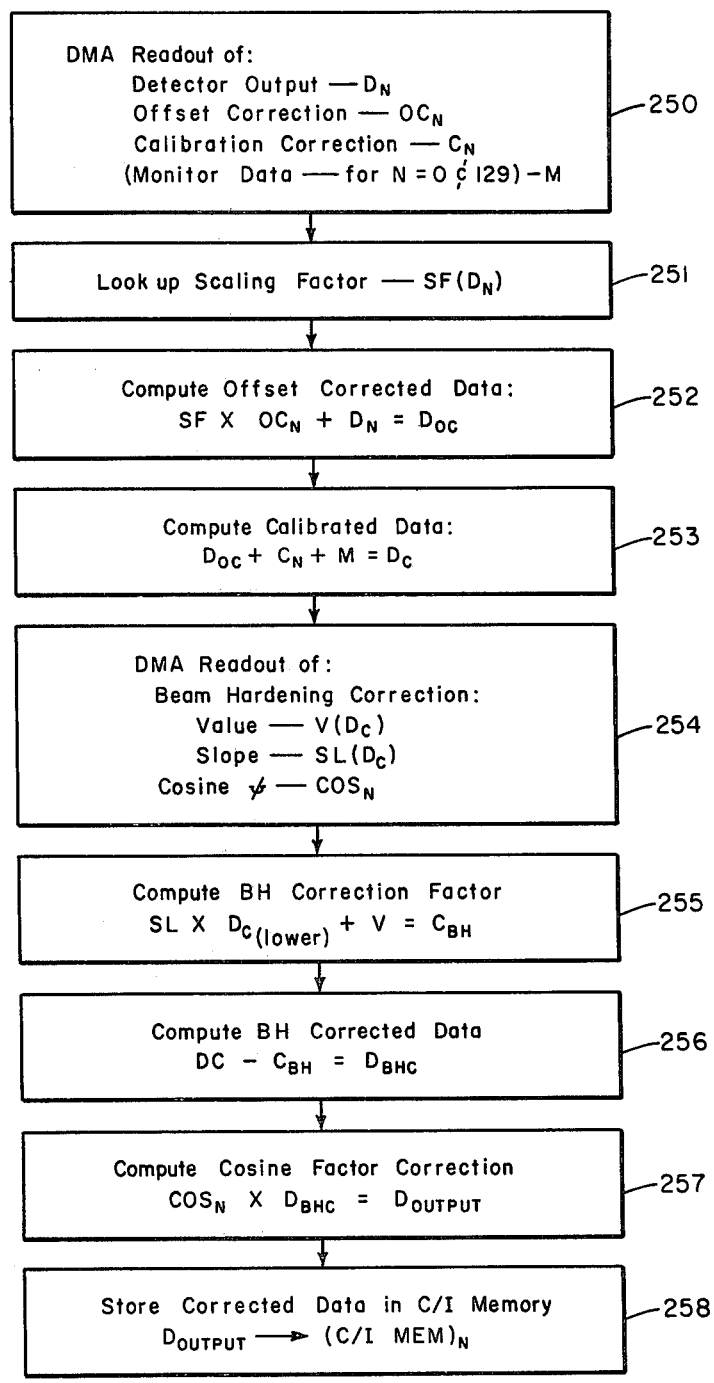
FIG. 5 is a flow diagram showing the calculations performed in the corrector.

FIG. 5 is a flow diagram showing the operations performed by the corrector in carrying out the above-described procedures. The corrector does not commence operation until after all the data from each of the detectors for the first projection has been stored in one of the data buffers in the computer memory 128. The steps performed by the corrector in correcting the raw detector data from the Nth detector are shown in FIG. 5. To commence the correction procedure, the corrector performs a DMA readout from computer memory 128 of: the raw detector output data from the Nth detector, $D_N$, stored in logarithmic form in one of the data tables; the offset correction factor corresponding with the Nth detector, $OC_N$; and the calibration correction factor for the Nth detector, $C_N$. Additionally, for the first detector in each of the right and left sections of the detector array, a correction factor, M, derived from the monitor detector data and converted by the corresponding A/D converter is read and stored. Since the monitor detector data is the same for all data detectors during each projection, this value need only be read twice, once for each converter. These steps are shown in block 250 of FIG. 5.

Next, the offset correction is performed. Due to the logarithmic nature of the data, the offset correction factor cannot be merely added to the data directly. Instead, it must be scaled by a factor which depends upon the slope of the logarithmic curve and hence is a function of the magnitude of the detector output data, $D_N$. In the preferred embodiment, the nine most significant bits of the raw data, $D_N$, control the look-up of an 8-bit scaling factor, $SF(D_N)$, block 251. This scaling factor is stored in a 512 × 8-bit table in the read-only memory of the corrector. Next, the offset correction is computed by multiplying the previously determined scaling factor, SF, by the offset correction for the Nth detector, $OC_N$, and adding this offset correction factor to the raw detector data to produce the offset-corrected data, $D_{OC}$, block 252.

Next, the gain calibration correction is computed. Since the measured data is logarithmic, a gain correction is performed by adding a correction factor to the offset-corrected detector data, the addition of logarithms being equivalent to multiplication. The monitor data represents variations in the intensity of the x-rays from x-ray source 10 which affect all detectors equally. The calibration correction, $C_N$, for the Nth detector must be added to the monitor data, M, for the current projection to produce a calibration correction normalized for the x-ray intensity for the current projection. (This is due to the fact that the calibration correction data $C_N$ was calculated by dividing the calibration correction factor by the monitor data for the calibration scan — equivalent to subtracting the logarithm of the monitor data from the calibration correction factor.) The calibrated data, $D_C$, is calculated by adding the offset-corrected data to the calibration correction factor and the monitor data, block 253.

Next, the corrector determines the beam-hardening correction factor and the detector-angle cosine factor. Due to the fact that the beam-hardening correction factor changes with different types of x-ray sources, the beam-hardening correction factor table is advantageously stored in the memory of computer 130 so that this table may be altered as needed. The beam-hardening correction table in the preferred embodiment is a piecewise linear approximation, each segment consisting of a value and a slope. Thus, the beam-hardening correction consists of a 10-bit magnitude $V(D_C)$ which is a function of the calibrated data and six bits denoting the slope of the beam-hardening correction factor, $SL(D_C)$, as a function of the calibrated data. The beam-hardening correction is divided into 96 segments and is addressed by the seven most significant bits of $D_C$. The beam-hardening correction factors and the cosine of the detector angle for the Nth detector are read from memory 128 of the computer by the corrector, as shown by block 254.

The beam-hardening correction factor is computed by multiplying the slope factor, SL, by the lower eight bits of the calibrated data, $D_{C(lower)}$, and adding this value to the magnitude V of the beam-hardening correction factor to produce the beam-hardening correction factor $C_{BH}$, block 255. Next, the beam-hardening correction factor is subtracted from the calibrated data to produce the beam-hardened corrected data $D_{BHC}$, block 256. Finally, the beam-hardened corrected data is multiplied by the cosine of the Nth detector angle to produce the output data from the corrector, block 257. The corrected data is then stored in the Nth address of C/I memory 120, block 258.

The corrector may be implemented in several different ways. Since only one set of corrections need by performed per projection, the above-described procedure must be repeated only 256 times during each projection; and in some applications, computer 130 may be able to perform all the correction calculations in the required time. (Note that this is in contrast with the convolver and image reconstructor which must deal with 256 × 256 individual operations per projection, each composed of many arithmetic steps.) Alternatively, the corrector may be implemented as a separate block especially adapted for performing the above-described operations. In the preferred embodiment, the latter alternative is chosen and the corrector is implemented by means of a dedicated processor system programmed to perform the above-described calculations.

Figure 6:
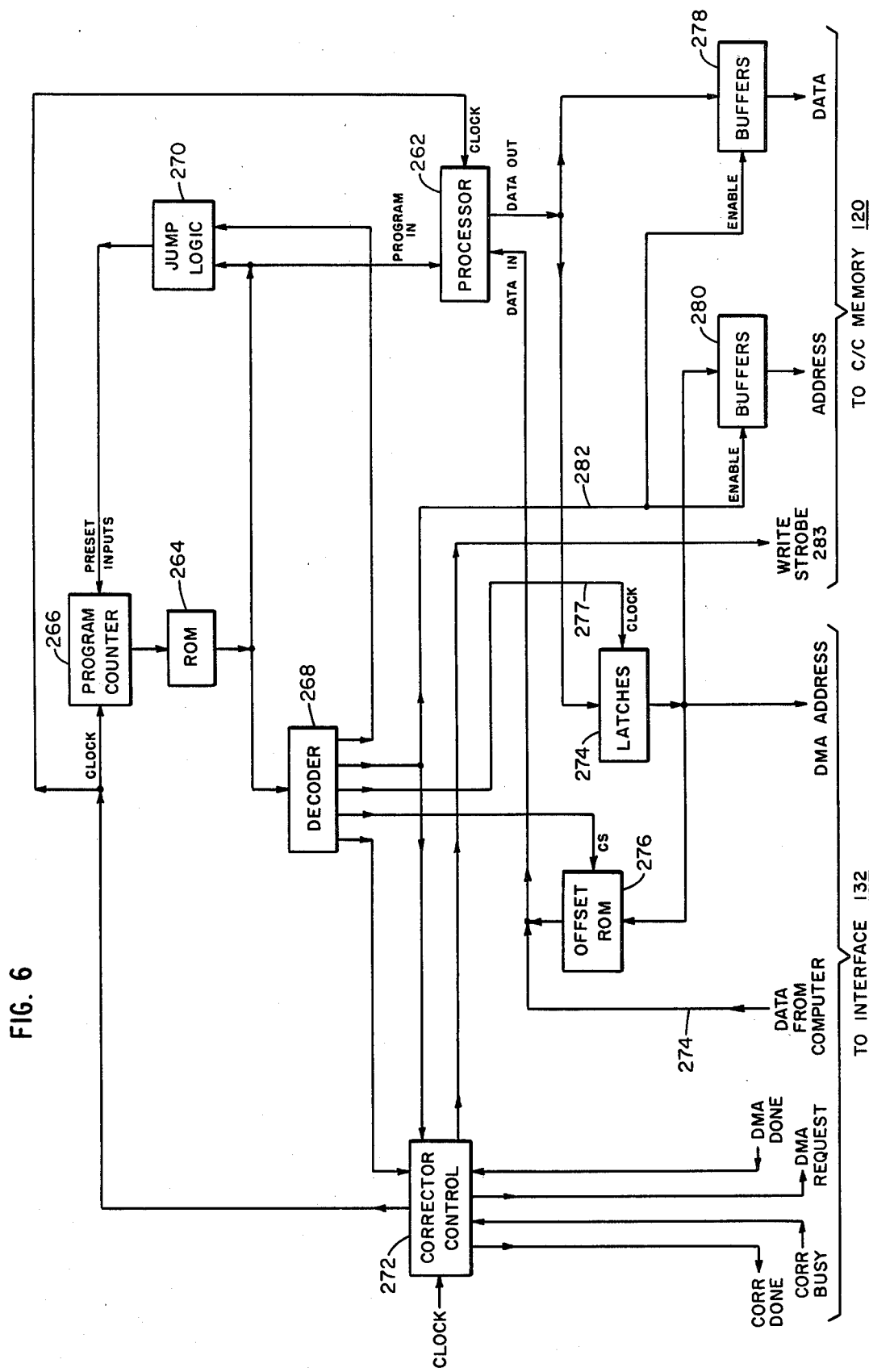
FIG. 6 shows the corrector circuitry.

FIG. 6 is a block diagram of the corrector circuitry used in the preferred embodiment described herein. The calculations performed by the corrector and the control functions for the remainder of the corrector circuitry are carried out in a processor 262. The functions of processor 262 may be performed by many different types of digital data processing equipment, including microprocessors. Many microprocessors are commercially available which may be used in implementing the corrector, and the general principles associated with the implementation and operation of these microprocessors are well-known to those in the art. In the preferred embodiment, processor 262 is made up of bipolar, bit-slice integrated circuits to form a 16-bit, high-speed microprocessor. In particular, the processor is made up of four Advanced Micro Devices AM2901 4-bit slice integrated circuits. The AM2901 processor is well-known and widely available, and extensive documentation of its structure and operation has been published. For this reason, the detailed operation and structure of processor 262 need not be further elaborated upon hereinbelow. Other digital processors and microprocessors may be suitable for use with the present invention, and the implementation of the present invention with a processor other than that described will be readily apparent to one of ordinary skill in the art. Accordingly, the description of a particular microprocessor in connection with the preferred embodiment is not to be construed as a limitation upon the invention.

The digital data denoting the program steps carried out by processor 262 in performing the calculations shown in FIG. 5 are stored in a read-only memory 264. Typically, read-only memory 264 may include five 256 × 4-bit ROM's. Table 1 shows the program data stored in ROM 264 in the preferred embodiment. This program data is adapted for use with the above-referenced Advanced Micro Devices microprocessor. The address inputs to ROM 264 are provided by an 8-bit program counter 266. In response to data in program counter 266 denoting an address location, ROM 264 produces data which is applied to the program inputs of processor 266 to cause the processor to perform the desired operations. Three bits from the output data of ROM 264 are applied to a one-of-eight decoder circuit 268. At selected points in the program, in response to the outputs from ROM 264, decoder 268 selectively produces one of several control signals described in more detail below.

The procedure, described with reference to FIG. 5, which processor 262 carries out, requires only a few branches in the program. These branching points may be implemented by providing the proper address data to the preset inputs of program counter 266 and presetting the counter to that value at the appropriate times. This is accomplished by applying data from ROM 264 and signals from decoder 268 to jump logic 270. In response to signals from ROM 264 indicating that a jump to a predetermined address is to be performed, jump logic 270 applies the proper inputs to the preset inputs of program counter 266 and then presets the counter to that address.

To begin operation of the corrector, interface 132 causes a CORR. BUSY to go from a low to a high state. In response, corrector control circuit 272 applies a clock signal to program counter 266 and to processor 262. After the correction of all data from a projection has been finished, a "last step" signal is produced by decoder 268 which is applied to corrector control 272. In response, corrector control sends a CORR. DONE signal to interface 132 and removes the clock signal from program counter 266 and processor 262. In response to the CORR. DONE signal, interface 132 causes the CORR. BUSY signal to return to a low state.

To read the detector output and correction data from computer 130, processor 262 provides data to latches 274 representative of the proper address of that data in computer 132. This data is clocked into latches 274 by a clock signal from decoder 268. Corrector control 272 then sends a DMA request signal to computer 130 via interface 132, interrupting the clock signals to program counter 266 and processor 262 while the corrector is waiting for the data. In response to the DMA request, the computer 130 and interface 132 apply the appropriate data to lines 274 going to the data inputs of processor 262 and send a DMA done signal to corrector control signal 272. Corrector control 272 then reapplies clock signals to program counter 266 and processor 262 to resume operation of the corrector.

The offset slope data is stored in an offset ROM 276. The address inputs to ROM 276 are provided from the outputs of latches 274. To read offset slope information from ROM 276, processor 262 applies the proper address information to latches 274 and clocks that information into latches 274 via a clock signal 277 from decoder 268. Next, decoder 268 provides a chip select (CS) signal to ROM 276 which enables the outputs of ROM 276, thereby providing the offset slope data to the data inputs to processor 262.

After all the correction calculations have been performed on a data point from a detector, the corrected data is stored in C/C memory 120. To do this, processor 262 first provides data on its data output lines representative of the proper address in the C/C memory, and this data is clocked into latches 274 by a clock signal 277 from decoder 268. Next, processor 262 provides the corrected data on its data output lines. This data is applied to the inputs of buffers 278. The C/C memory address data in latdches 274 is similarly applied to the inputs of buffers 280. Next, decoder 268 provides a positive signal on line 282 which enables three-state buffers 278 and 280 so that the address data and corrected detector data is applied to C/C memory 120. This signal on line 282 is also applied to corrector control 272 which provides a write strobe 283 to C/C memory 120 and causes the program counter 266 to jump on the next clock pulse to begin the correction calculations for the next data point. After all the data points for a projection have been corrected in the corrector, control circuit 272 provides a CORR. DONE signal to interface 132 and the corrector remains idle until it receives an indication from computer 130 via interface 132 that the data from the next projection is available for processing.

TABLE 1
CORRECTOR MICROPROCESSOR PROGRAM

| STATE | COMMENTS | OPERATIONS R | F | S | D | Y | PROGRAM STEPS J-1 | J-4 | J-21 | J-55 | SPEC. CODE UTS | C | NPR | RAM A | B | INSTRUCTION 210 | 543 | 876 |
|---|---|---|---|---|---|---|---|---|---|---|---|---|---|---|---|---|---|---|
| 1 | Increment Index REG (R2) | φ | + | B | B | A | 0 | | | | 0 | 0 | 0 | 2 | 2 | 3 | 0 | 2 |
| 2 | First NPR Sequence<br>Strobe for Monitor<br>1. Special MON Code; S=1<br>2. ADDRESS B=5<br>3. NPR=1; ACQ. BUS<br>4. INDEX CTR (R2) → OUTPUT REG. | φ | V | B | B | A | 1 | | | | 6 | 0 | 1 | 2 | 5 | 3 | 3 | 2 |
| | | | | (B→B) | | | | | | | | | | | | | | |
| 3 | Load Monitor Into R6<br>1. NPR=1; HOLD BUS | D | V | φ | B | F | 2 | | | | 0 | 0 | 0 | 6 | 6 | 7 | 3 | 3 |
| | | | (D→B) | | | | | | | | | | | | | | | |
| 4 | Strobe for Data<br>1. ADDRESS B=0<br>2. NPR=1; HOLD BUS<br>3. RESET R0<br>4. INDEX CTR (R2) → OUTPUT REG.<br>5. CARRY=1 (FOR CAR SEL IN STATE 5)<br>6. S=1 | φ | A | B | B | A | 3 | 120 | | | 4 | 1 | 1 | 2 | 0 | 3 | 4 | 2 |
| | | | (φ→B) | | | | | | | | | | | | | | | |
| 5 | Load Data into R1<br>1. NPR=1; HOLD BUS | D | V | φ | B | F | 4 | 121 | | | 0 | 0 | 0 | 1 | 1 | 7 | 3 | 3 |
| | | | (D→B) | | | | | | | | | | | | | | | |
| 6 | Strobe for Calib.<br>1. ADDRESS B=4<br>2. NPR=1; HOLD BUS<br>3. RESET R4<br>4. INDEX CTR (R2) → OUTPUT REG.<br>5. S=1<br>6. CARRY=0 | φ | A | B | B | A | 5 | 122 | | | 4 | 0 | 1 | 2 | 4 | 3 | 4 | 2 |
| | | | (φ→B) | | | | | | | | | | | | | | | |
| 7 | Load Calib. Into R5<br>1. NPR=1; HOLD BUS | D | V | φ | B | F | 6 | 123 | | | 0 | 0 | 0 | 1 | 1 | 7 | 3 | 3 |
| | | | (D→B) | | | | | | | | | | | | | | | |
| 8 | Strobe for Offset<br>ADDRESS B=7<br>2. NPR=0; RELEASE BUS<br>3. RESET R7<br>4. INDEX CTR → OUTPUT REG. (R2)<br>5. S=1 | φ | A | B | B | A | 7 | 124 | | | 4 | 0 | 0 | 2 | 7 | 3 | 4 | 2 |
| | | | (φ→B) | | | | | | | | | | | | | | | |
| 9 | Load Offset Into R3<br>1. NPR=0; LAST DMA IN THE FIRST NPR SEQUENCE | D | V | φ | B | F | 10 | 125 | | | 0 | 0 | 0 | 3 | 3 | 7 | 3 | 3 |
| | | | (D→B) | | | | | | | | | | | | | | | |
| 10 | Set Up SF For Multiplication<br>Strobe for SF<br>1. ADDRESS FOR THE INTERNAL TABLE FROM R1 (DATA)<br>2. DATA × 2 TO OUTPUT REG.<br>3. SPECIAL SF CODE: S=1<br>4. NPR=0<br>5. JUMP TO 21, IF ADDRESS=LOWER 4; | A | + | B | Y | F | 11 | 126 | | | 5 | 0 | 0 | 1 | 1 | 1 | 0 | 1 |
| | | (A=BSo 2B→Y)<br>(B UNCHANGED) | | | | | | | | | | | | | | | | |
| 11 | $\overline{Y15} \cdot \overline{Y14} = 1$<br>Load SF Into Q Reg.<br>1. D→Q | D | V | φ | Q | F | 12 | 127 | | | 4 | 0 | 0 | 7 | 7 | 7 | 3 | 0 |
| | | | (D→Q) | | | | | | | | | | | | | | | |
| 12 to 18 | 2. STROBE TO CLEAR SF BIT; S=1<br>Multiply SF × Offset Q × R3 → R0<br>Conditional Add/Shift 7 Times<br>1. SPECIAL MULT STEP CODE: S=3<br>2. Q=φ; (φ + B)/2 → B<br>Q=1; (A + B)/2 → B<br>SF=8(MAX.) | A | + | B | B | F | 13<br>14<br>15<br>16<br>17<br>20<br>21 | 130<br>131<br>132<br>133<br>134<br>135<br>136 | | | 3<br>3<br>3<br>3<br>3<br>3<br>3 | 0<br>0<br>0<br>0<br>0<br>0<br>0 | 0<br>0<br>0<br>0<br>0<br>0<br>0 | 3<br>3<br>3<br>3<br>3<br>3<br>3 | 0<br>0<br>0<br>0<br>0<br>0<br>0 | 1<br>1<br>1<br>1<br>1<br>1<br>1 | 0<br>0<br>0<br>0<br>0<br>0<br>0 | 4<br>4<br>4<br>4<br>4<br>4<br>4 |

TABLE 1-continued
CORRECTOR MICROPROCESSOR PROGRAM

| STATE | COMMENTS | OPERATIONS R | F | S | D | Y | PROGRAM STEPS J-1 | J4 | J-21 | J-55 | SPEC. CODE UTS | C | NPR | RAM A | B | INSTRUCTION 210 | 543 | 876 |
|---|---|---|---|---|---|---|---|---|---|---|---|---|---|---|---|---|---|---|
| 19 | Note that offset is X8 before being put in table. Cond. Add/Shift and Round Off 1. SPECIAL MULT STEP CODE; S=3 2. OFFSET CORRECTION IN R0 | φ | + | B | B | F | 22 | 137 | | | 3 | 1 | 0 | 3 | 0 | 1 | 0 | 4 |
| 20 | Correction Arithmetic R1-R0 → R1 Jump from 10 | −A | + | B | B | F | 23 | 140 | | | 0 | 1 | 0 | 0 | 1 | 1 | 1 | 3 |
| 21 | DATA - CALIBRATION R1-R5 → R1 DATA - MONITOR | −A | + | B | B | F | 24 | 141 | 240 | | 0 | 1 | 0 | 5 | 1 | 1 | 1 | 3 |
| 22 | R1-R6 → R1 1. SPECIAL JUMP ON NEGATIVE CODE 2. JUMP TO 55, IF NEGATIVE RESULT; F3=1 Second NPR Sequence | −A | + | B | B | F | 25 | 142 | 241 | | 2 | 1 | 0 | 6 | 1 | 1 | 1 | 3 |
| 23 | Strobe For Cos 1. ADDRESS B=3 2. NPR=1; ACQ BUS 3. INDEX CTR (R2) → OUTPUT REGISTER 4. RESET R3 | φ | A | B | B | A | 26 | 143 | 242 | | 4 | 0 | 1 | 2 | 3 | 3 | 4 | 2 |
| 24 | Load COS Into R5 1. NPR=1; HOLD BUS | D | V | φ (D→B) | B | F | 27 | 144 | 243 | | 0 | 0 | 1 | 5 | 5 | 7 | 3 | 3 |
| 25 | Strobe for BHC 1. ADDRESS B=5 2. S=1 3. NPR=0; RELEASE BUS | φ | V | B | B | A | 30 | 145 | 244 | | 4 | 0 | 0 | 1 | 5 | 3 | 3 | 2 |
| 26 | 4. DATA (R1) → OUTPUT REG. Load BHC Into Q 1. NPR=0; LAST DMA IN SECOND NPR SEQUENCE | D | V (D→Q) | φ | Q | F | 31 | 146 | 245 | | 0 | 0 | 0 | 7 | 7 | 7 | 3 | 0 |
| 27 | Set Up BHC Slope Multiplication 1. TRANSFER LSB's OF DATA FROM R1 to R0 2. TRANSFER MSB's OF DATA AS φ to R0 3. SPECIAL BYTE TRANSFER CODE 4. S=0 | φ φ | + + | A A B | B F | F | 32 | 147 | 246 | | 1 | 0 | 0 | 1 | 0 | 4 | 0 | 3 |
| 28 to 32 | Multiply Slope × Data 0 × R0 → R3 | A | + | B | B | F | 33 34 35 36 37 | 150 151 152 153 154 | 247 250 251 252 253 | | 3 3 3 3 3 | 0 0 0 0 1 | 0 0 0 0 0 | 0 0 0 0 0 | 3 3 3 3 3 | 1 1 1 1 1 | 0 0 0 0 0 | 4 4 4 4 4 |
| 33 | Conditional Add/Shift 5 Times | | | | | | 40 | 155 | 254 | | 3 | 1 | 0 | 0 | 3 | 1 | 1 | 4 |
| 34 | 1. Q/2 → Q Cond. Subt./Shift 1. Q/2 → Q Shift R3 | −A | + | (B/2 → B) B | B | F | 41 | 156 | 255 | | 0 | 0 | 0 | 3 | 3 | 3 | 0 | 5 |
| 35 | 1. Q → Q Shift and Roundoff R3 Q → Q | φ | + | [(1 + B)/2 → B] B BHC (Correction) | B | F | 42 | 157 | 256 | | 0 | 1 | 0 | 3 | 3 | 3 | 0 | 5 |
| 36 | LO BHC R1 - R3 → R1 | −A | + | B | B | F | 43 | 160 | 257 | | 0 | 1 | 0 | 3 | 1 | 1 | 1 | 3 |
| 37 | HI BHC R1 - Q → R1 | A | − | Q | B | F | 44 | 161 | 260 | | 0 | 1 | 0 | 1 | 1 | 0 | 2 | 3 |
| 38 | Q IS THE SHIFTED REMAINDER = V Q IS THE SHIFTED REMAINDER = V Set up for COS Multiplication TRANSFER COS (R5) to Q | φ | V | B | Q | F | 45 | 162 | 261 | | 0 | 0 | 0 | 5 | 5 | 3 | 3 | 0 |

TABLE 1-continued
CORRECTOR MICROPROCESSOR PROGRAM

| STATE | COMMENTS | OPERATIONS | | | | | PROGRAM STEPS | | | | SPEC. CODE | | | RAM | | INSTRUCTION | | |
|---|---|---|---|---|---|---|---|---|---|---|---|---|---|---|---|---|---|---|
| | | R | F | S | D | Y | J-1 | J-4 | J-21 | J-55 | UTS | C | NPR | A | B | 210 | 543 | 876 |
| 39 to 53 | Multiply COS × Data Q × R1 → R4<br>1. CONDITIONAL ADD/SHIFT 15 TIMES<br>2. Q/2 → 2 | A | + | B | B | F | 46 | 164 | 262 | | 3 | 0 | 0 | 1 | 4 | 1 | 0 | 4 |
| | | | | | | | 47 | 165 | 263 | | 3 | 0 | 0 | 1 | 4 | 1 | 0 | 4 |
| | | | | | | | 50 | 166 | 264 | | 3 | 0 | 0 | 1 | 4 | 1 | 0 | 4 |
| | | | | | | | 51 | 167 | 265 | | 3 | 0 | 0 | 1 | 4 | 1 | 0 | 4 |
| | | | | | | | 52 | 170 | 266 | | 3 | 0 | 0 | 1 | 4 | 1 | 0 | 4 |
| | | | | | | | 53 | 171 | 267 | | 3 | 0 | 0 | 1 | 4 | 1 | 0 | 4 |
| | | | | | | | 54 | 172 | 270 | | 3 | 0 | 0 | 1 | 4 | 1 | 0 | 4 |
| | | | | | | | 55 | 173 | 271 | | 3 | 0 | 0 | 1 | 4 | 1 | 0 | 4 |
| | | | | | | | 56 | 174 | 272 | | 3 | 0 | 0 | 1 | 4 | 1 | 0 | 4 |
| | | | | | | | 57 | 175 | 273 | | 3 | 0 | 0 | 1 | 4 | 1 | 0 | 4 |
| | | | | | | | 60 | 176 | 274 | | 3 | 0 | 0 | 1 | 4 | 1 | 0 | 4 |
| | | | | | | | 61 | 177 | 275 | | 3 | 0 | 0 | 1 | 4 | 1 | 0 | 4 |
| | | | | | | | 62 | 200 | 276 | | 3 | 0 | 0 | 1 | 4 | 1 | 0 | 4 |
| | | | | | | | 63 | 201 | 277 | | 3 | 0 | 0 | 1 | 4 | 1 | 0 | 4 |
| | | | | | | | 64 | 202 | 300 | | 3 | 0 | 0 | 1 | 4 | 1 | 0 | 4 |
| 54 | CONDITIONAL ADD/SHIFT AND ROUND OFF | A | + | B | B | | 65 | 203 | 301 | | 3 | 1 | 0 | 2 | 4 | 1 | 0 | 4 |
| 55 | Final Storage of Data in CC Memory<br>Strobe for Write in CC Memory<br>(B→B)<br>1. INDEX CTR (R2) → OUTPUT REGISTER<br>2. SPECIAL LAST POINT CODE<br>JUMP FROM 22 | φ | V | B | B | A | 66 | | 302 | 360 | 7 | 0 | 0 | 2 | 2 | 3 | 3 | 2 |
| 56 | CC Write<br>1. R4 → Y OUTPUT<br>2. (LEAVE LAST POINT CODE)<br>3. INCREMENT INDEX CTR (R2) | φ | + | B | B | A<br>(1+B→B) | 67 | 204 | 303 | 361 | 7 | 0 | 0 | 4 | 2 | 3 | 0 | 2 |
| 57 | Increment Index<br>1. R4 → Y OUTPUT<br>2. STROBE TO CLEAR LAST POINT CODE<br>3. INCREMENT R2:<br>LSB: $\phi_{LSB} + B_{LSB} \to B_{LSB}$<br>$\phi_{MSB} + 1 + B_{MSB} \to B_{MSB}$<br>JUMPS:<br>TO 1 on OVR<br>TO 4 on OVR . CARRY<br>TO 256 On CARRY<br>(Also Reset Busy) | φ | + | B | B | A<br>(1+B→B) | 70 | 205 | 304 | 362 | 4 | 0 | 0 | 4 | 2 | 3 | 0 | 2 |
| 256 | Rest State<br>1. RESET R2 (INDEX)<br>2. CLEAR ALL SPEC. CODES<br>3. JUMP TO 1 ON TC · BUSY | φ | A<br>(φ→B) | B | B | F | | | | 377 | 4 | 0 | 0 | 2 | 2 | 3 | 4 | 3 | kernal address counter 366 is cloced into pipeline latches 372 where this value is held to provide the proper address information to kernal memory 340 in the second stage of the pipeline processor. The respective outputs from kernal memory 340 and C/C memory 120 are clocked into pipeline latches 374 and 376 by the next pulse from convolver clock 368. This data is applied to a multiplier array, described below, which performs the convolution multiplication and sums the products to complete the convolution.

Prior to the convolution of data from a projection, convolver control logic 316 initially sets data address counter 360 and convolution number counter 362 to zero via reset signal on line 358. The reset signal is also applied through OR gate 364 to the load input of a kernal address counter 366. The value of convolution number counter 362 is applied to the preset inputs of kernal address counter 366 for reasons explained below. Since the convolution number counter is reset to zero by the reset signal on line 358, this zero value is loaded into kernal address counter 366, effectively resetting the kernal address counter to zero to begin the convolution processing.

After the CONV BUSY signal goes high starting the convolution processing, data address counter 360 and kernal address counter 366 are incremented in unison by convolver clock 368 to provide the proper address data to the C/C and kernal memories. This process is repeated 256 times to process each of the 256 values from each of the detectors. When the value in data address counter 360 reaches 255 (where 0 is the first state), the carry output from counter 360 goes high, providing an end-of-convolution (EOC) signal 379, indicating that the convolution for one data point is complete. The EOC signal 379 is applied to the reset input of data address counter 360 which is reset to zero by the next clock pulse, and is applied to line 380 where it is clocked through pipeline latches and eventually resets the convolver accumulator and clocks the output thereof into the interpolator, as described below.

The EOC signal is applied to a 9-bit convolution number counter 362 and, following each convolution, increments the value in this counter by one. The EOC signal is also applied through OR gate 364 to the load input of kernal address counter 366. This causes kernal address counter 366 to be preset with a value equal to the value in convolution number counter 362. Due to the presetting of kernal address counter 366, the deblurring function and the data are offset by one more data point for each succeeding convolution. When each convolution has been completed, as determined by data address counter 360 and detector 378, this offset results in the corresponding convolved data point being produced by the convolver. In this manner, each of the desired data points is produced.

The actual convolution kernal is 511 bits long, although only 256 of these bits are convolved with the data in C/C memory 120 to produce any one convolved data point. To produce the first convolved point, the deblurring function, shown in FIG. 7A, is aligned with the data such that the positive peak 383 of the deblurring function multiplies the first data point, the second value of the deblurring function multiplies the second data point, and so on. To produce the second convolved data point, the deblurring function is shifted by one value so that positive peak 383 multiplies the second data point. The deblurring function is successively shifted in this manner to produce the remaining convolved data points. In order to perform the convolutions in this way, the convolver works in the following manner.

The various deblurring functions all have the properties that they are symmetrical. This is shown in FIG. 7A where the deblurring function is roughly sketched. It can be seen that this function is symmetric about line 382. To minimize storage requirements, only half of the deblurring function is stored in the computer and in kernal memory 340, the positive peak being stored in the first (0) location is the kernal memory and succeeding points (either to the right or left, since both are identical) being stored in succeeding locations. As described above, to begin a convolution, kernal address counter 366 is set to the convolution number. The kernal address up/down counter then counts down until it reaches zero, with the proper data from C/C memory and deblurring function values being provided for convolution. When the counter reaches zero, the positive peak is produced by the kernal memory, and the proper data point is produced by the C/C memory in response to the data address counter. When the kernal address counter reaches zero, a "0" output from the counter clocks flip-flop 384, whose output goes to the up/down input of the kernal address counter. Flip-flop 384 changes state, causing the up/down kernal address counter 366 to count up on succeeding clock pulses. Counter 366 continues to count up until counter 366 and flip-flop 384 are reset at the end of the convolution of that data point by the signal from OR gate 364.

For example, if the 13th convolution is being performed, the kernal address counter is preset to 12 (since 0 is the first convolution); and after 12 pulses, the C/C memory provides the 13th data point at its output, and the kernal memory provides the positive peak at its output. As the kernal counter counts down to zero from its preset value, the proper values of the deblurring function to the left of positive peak (which are the same as the values to the right) are provided in the proper order to multiply the data points preceding the 13th data point. After kernal address counter reaches the zero state, it reverses direction and counts up to provide the proper values of the deblurring function multiplying the data points following the 13th data point.

After 256 separate convolutions have been carried out, the ninth bit from convolution number counter 362, on line 363, goes high. This signal is applied to the interpolator circuitry to indicate that the last data point has been processed by the convolver.

Figure 7:
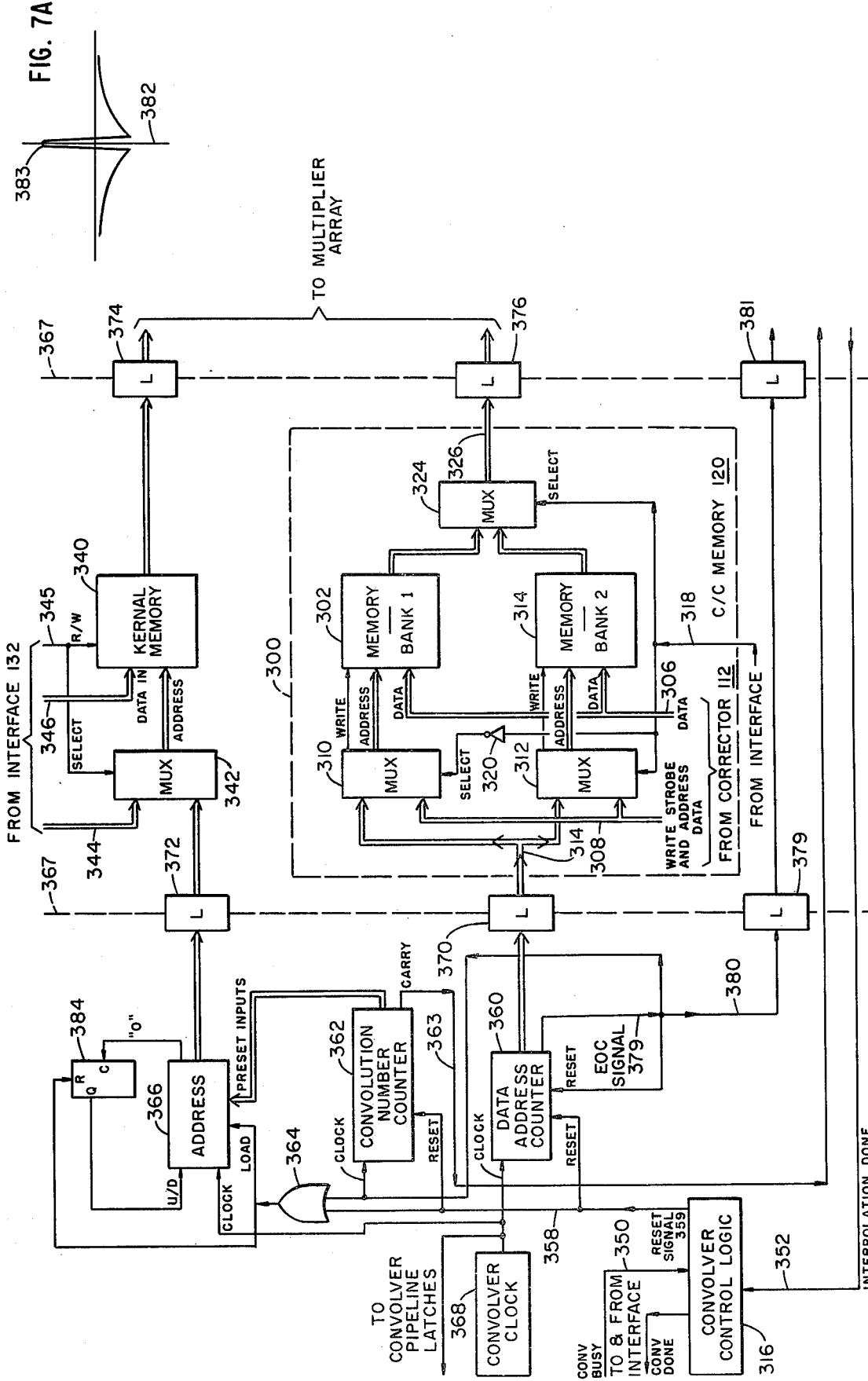
FIG. 7 is a block diagram of the C/C memory and part of the convolver circuitry.
Figure 8:
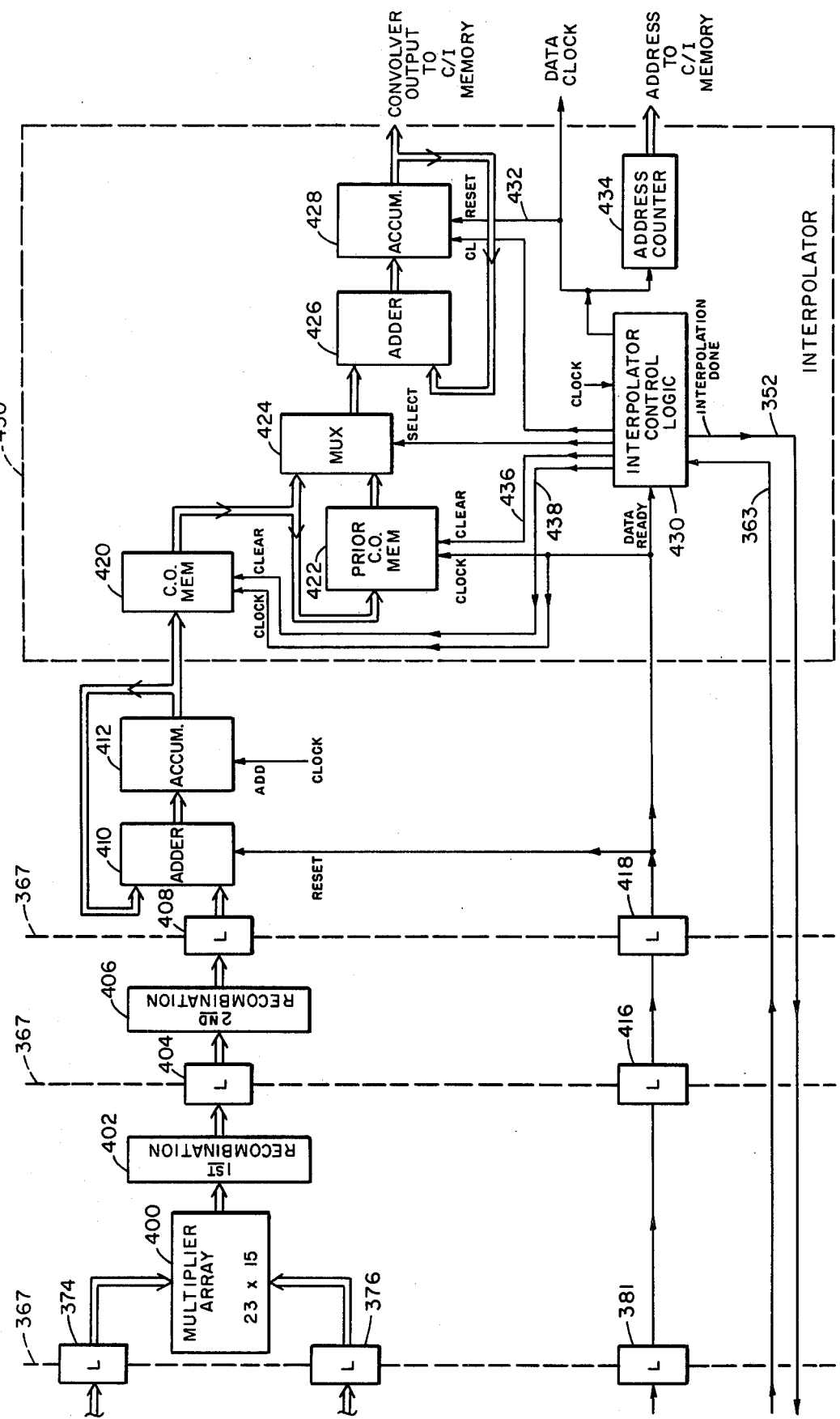
FIG. 8 is a block diagram of the remainder of the convolver circuitry and the interpolator circuitry.

Referring to FIG. 8, the remainder of the convolver circuitry is shown. From latches 374 and 376, shown in both FIGS. 7 and 8, the kernal data, representative of the deblurring function value, and the corrected detector data from C/C memory 120 are applied to the inputs of multiplier array 400. Multiplier 400 is a 23 × 15-bit multiplier and may be implemented in many different ways. In the preferred embodiment, multiplier 400 is implemented using 4 × 4 multiplier circuits, the outputs of which are combined in a Wallace tree. One 4 × 4 multiplier integrated circuit suitable for use in multiplier 400 is a 74S274. The first partial products from multiplier array are summed in first stage recombination circuit 402. The output from recombination circuit 402 is cloced into pipeline. latches 404 by the convolver clock. The partial products in latches 404 are applied to second stage recombination circuit 406. The output of the second stage recombination is the final product which is clocked into pipeline latches 408. First recom-

Convolver

As each piece of corrected data is produced by the corrector, it is stored in the two-bank, corrector/convolver, or C/C memory 120. The C/C memory is shown in FIG. 7 enclosed within dotted box 300 and works in the following manner. As each data point is calculated, it is stored by the corrector in one bank of C/C memory. Simultaneously, data stored in the other bank of the C/C memory is being accessed by the convolver circuitry as it performs the required convolution calculations described below. At the end of the processing of data from each projection when both the corrector and convolver are idle, the memory banks are electronically interchanged. The data produced by the corrector during the previous scan is now available for the convolver, and the data previously convolved and no longer needed is written over by the new data from the corrector as this data is stored in the C/C memory.

Central to the operation of the C/C memory are two random access memories 302 and 304 forming the two independent banks of memory. In the preferred embodiment, each of these memories is a 256 × 15 bit memory. The data from the corrector is applied on lines 306 to the data inputs of each memory bank. The address data from the corrector, indicating which detector corresponds with the data then present on the data lines 306, and the write strobe signal are applied on lines 308 to two 2-channel multiplexers 310 and 312. The other inputs to multiplexers 310 and 312 are applied on lines 314 and come from the convolver circuitry, as described below. The select inputs to multiplexer 312 and the read/write signal to memory 304 are supplied by interface circuit 132 on line 318; and this signal is inverted by inverter 320 and applied to the select input of multiplexer 310 and the read/write input of memory 302. Thus, when one of the banks 302 and 304 of the C/C memory is in write mode, the other is in read mode. The data outputs from memory banks 302 and 304 are applied to a 2-channel multiplexer 324 whose select input also comes from line 318.

The signal on line 318 changes state as each projection processing cycle is begun. Thus, the write strobe and address data from the corrector are first applied to memory bank 302, which is in write mode, and the data from the corrector on line 306 is written into memory bank 1. Simultaneously, address data on lines 314 is applied via multiplexer 312 to memory bank 304 which is in read mode, causing the desired data to be presented at the output of memory 304. Multiplexer 324 applies this data to the output 326 of the C/C memory.

When one projection is finished, the signal on line 318 changes state. The above-described procedure is reversed during the following projection, the data from the corrector being stored in bank 2, while the convolver accesses the data previously stored in bank 1.

The deblurring function with which the data from the corrector is convolved may be varied by a technician operating the tomography system, depending on what features he wishes to emphasize in the final image, as described above. The data representative of the deblurring function is called a kernal. The different kernals available to a technician are stored in the memory of the computer 140. Prior to performing a tomographic scan, the computer via interface 132 loads the selected kernal into the convolver.

In the preferred embodiment, the kernal is composed of 256 24-bit words. The kernal is stored in a random access memory 340 by computer 130 and interface 132 as follows. The address data for memory 340 is selected by multiplexer 342. When a new kernal is to be loaded, the interface applies a signal to the select input of multiplexer 342, causing it to connect address lines 344 from the interface to the address lines of memory 340. This signal also is applied to the read-write input of memory 340 and causes the memory to be in write mode. Each piece of data of the kernal is then written into the kernal memory on lines 346 by the computer via the interface. After this has been completed, line 345 goes back to its original state. In response to this, multiplexer 342 selects the address data from the convolver circuitry on line 348 for application to kernal memory 340, and the data stored in memory 340 is recalled as needed during the convolution processing.

Since data from all 256 detectors in a projection must be stored in one bank of the C/C memory before the convolver can access this data, the convolver does not begin operating until after the first projection has been completed. When the first projection has been completed and the last piece of detector data has been processed in the corrector and loaded in the C/C memory, interface 132 causes a convolver busy (CONV BUSY) signal on line 350 to go high, starting operation of the convolver/interpolator. Interface 132 also changes the state of line 318, allowing the corrector to write the data from the next projection in the other bank of the C/C memory and making the data from the previous projection available to the convolver, as explained above.

After the data has been convolved, the interpolator provides the interpolated values between each of the measured data points. Due to the pipeline processor structure of the convolver and interpolator, the interpolation process is not finished until several clock periods after the last convolution has been completed. When the interpolation process is finished, the interpolator sends an "interpolation done" signal on line 352 to convolver control logic 316. Upon receipt of this signal, the convolver control logic sends a CONV DONE signal to interface 132, indicating the convolver has finsished processing the corrected data from the previous projection. The interface then returns the CONV BUSY signal to a low state. In the preferred embodiment described herein, the entire convolution and interpolation processing of 256 pieces of data from one projection is performed in approximately 10.6 milliseconds. Since one projection is taken every 13.9 milliseconds, the convolver will be idle for approximately 3.3 milliseconds following the processing of data from one projection before the corrector has loaded the C/C memory with all the data from the next projection.

A convolver clock 368 provides clock signals to the convolver and interpolator circuitry. In the preferred embodiment, the convolver clock has a frequency of 6.25 MHz. Data produced by each of the pipeline stages is clocked into intermediate holding latches between the stages by the convolver clock signal, which is applied to each of these latches. The pipeline latches and the division between each of the pipeline stages are shown by the vertical dotted lines 367 in FIG. 7.

Convolver clock 368 provides clock signals to a 9-bit data address counter 360, and an 8-bit kernal address up/down counter 366. These counters are incremented in unison by the signals from convolver clock 368. The value in data address counter 360 is cloced into pipeline latches 370 where the value is held to provide the address information to the C/C memory 120. The value in bination stage 402 may be implemented using 74S275 7-bit-slice, Wallace tree integrated circuits, and recombination stage 406 may be implemented with adders. For a detailed description of Wallace tree multipliers and recombination stages, reference should be made to *TTL Data Book for Design Engineers*, 2d Ed., published by Texas Instruments, Inc., 1976, pp. 7-391 to 7-400.

The value stored in pipeline latches 408 is a 32-bit value in signal magnitude notation which is the product of one piece of detector data multiplied by one value of the deblurring function. For each complete convolution, 256 of these values are summed to produce each convolved data point. The data in latches 408 is applied to one input of adder 410 with the sign bit being applied to the add/subtract input. The output of adder 410 is applied to an accumulator register 412. The value stored in accumulator register 412 is applied to the second input of adder 410. Prior to the beginning of the convolution for each data point, accumulator register 412 is reset to zero by the EOC signal 379 from counter 360 applied via the pipeline latches. The first product clocked into latches 408 is added to the zero value in accumulator 412 by adder 410 and clocked into accumulator 412 by the convolver clock applied to the clock input of accumulator 412. Succeeding products stored in latch 408 are added by adder 410 to the sub-total accumulated in accumulator register 412, and the new sub-total is clocked into accumulator 412 by the convolver clock. After 256 such additions and accumulations, the value stored in accumulator 412 is the desired convolved data point.

The EOC signal 379 produced by detector 378 following the last data point is clocked through latches at each stage of the pipeline. Thus, the EOC signal will be clocked through the stages of the pipeline one stage behind the last data processed in each convolution. Thus, after the last value has been added to the total in accumulator 412, the EOC signal 379 will appear in latch 418 on the next clock pulse from convolver clock 368. This pulse is applied to adder 410, setting the adder output to zero and resulting in the clearing of accumulator 412 by the next clock pulse in preparation for the next convolution. The output of latch 418 is also applied to the clock input of a convolver output memory 420 in the interpolator. The data in accumulator 412 is applied to the data inputs of convolver output memory 420, and this data is clocked into memory 420 and the interpolator by the EOC signal in latch 418.

Interpolator

The output from the convolution circuitry is applied to the interpolation circuitry. The following explains why the interpolation is necessary and how it is performed. In reconstructing the image, the body being scanned is considered to be divided up into small areas of uniform density. The areas are referred to as pixels (picture elements). In the preferred embodiment described, the circular area scanned by the x-ray source and detector array is divided such that the circle exposed by the scanner is enclosed within a square 256 × 256 pixels on a side. This is shown diagrammatically in FIG. 9.

Figure 9:
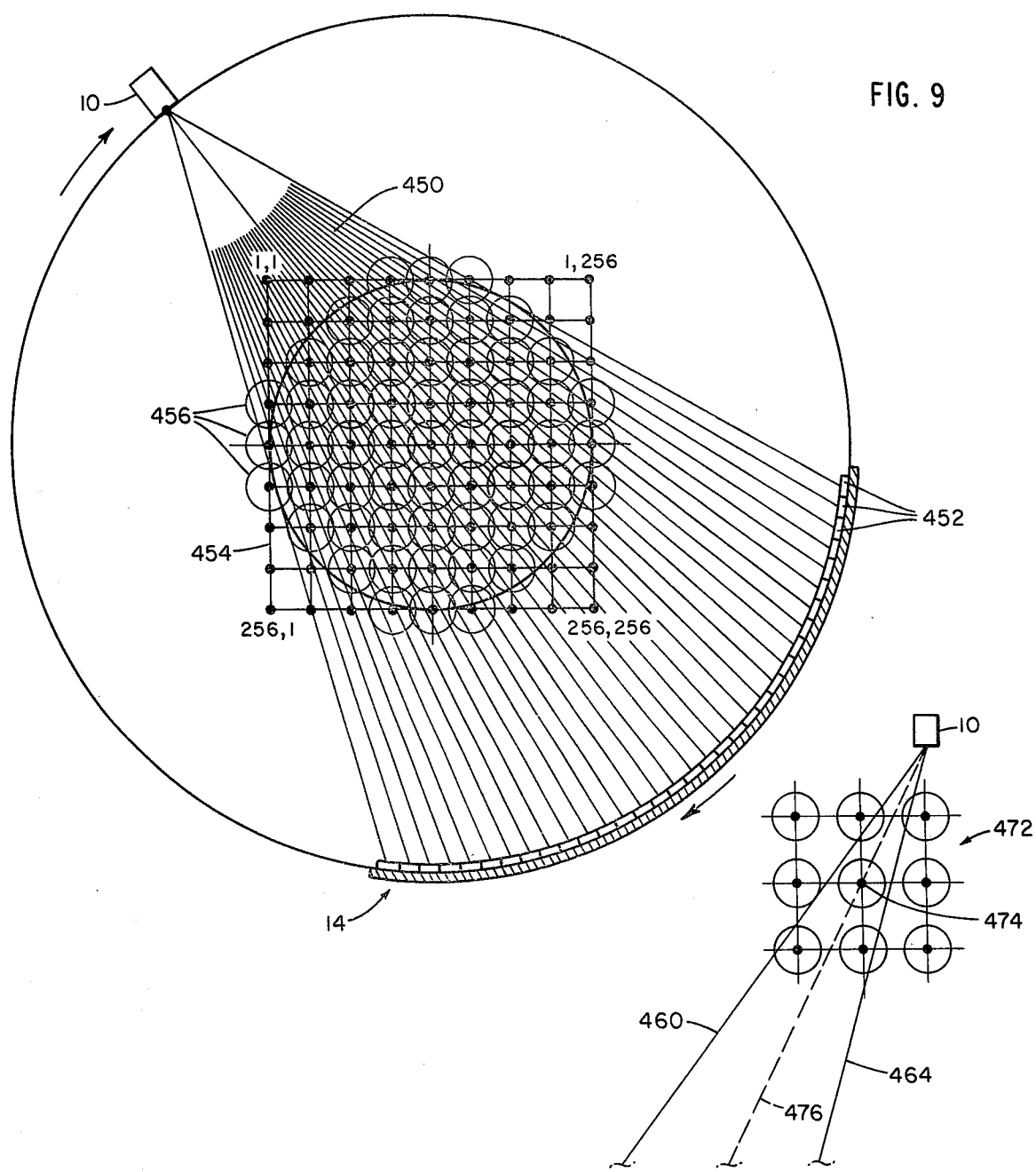
FIG. 9 shows a pixel array and its relationship with the x-ray fan beam.

Due to the geometry of the system, "rays" emanating from x-ray source 10 and impinging upon the detector array 14 do not always pass through the center of a pixel, and frequently, more than one ray passes through a pixel. In FIG. 9, rays 450 (actually small "fans" of x-ray energy rather than single rays) impinge upon each of the individual detectors 200 in detector array 14. Grid 454 shows the pixels 456 into which the body being scanned is divided in the image memory. The dots within grid 454 denote the center of each pixel. The reconstruction algorithm assumes that the convolved data used in producing the value of each pixel is the result of a ray from x-ray source 10 passing through the center of that pixel. As can be seen from FIG. 9, this approximation is not true for all pixels. Also, the pixel array 454 is fixed in the patient frame of reference, and the relationship between the pixel centers and the rays 450 impinging on each detector changes with each exposure as the x-ray source and detector array are rotated about the fixed pixel array 454.

The interpolator calculates data corresponding to seven additional locations between each of the detectors in detector array 14. This is done by means of a linear interpolation. Thus, the interpolated data point between two adjacent detectors and immediately adjacent to the first detector consists of the convoluted output of the first detector with a weight of 7/8 and the convoluted output from the second detector with a weight of ⅛, and so on, through each of the intermediate areas between detectors. In performing the back projection, the image reconstruction circuitry calculates the interpolated data point intersected by a ray passing through the center of each pixel, and this data is used in calculating the density of that pixel.

Figure 10:
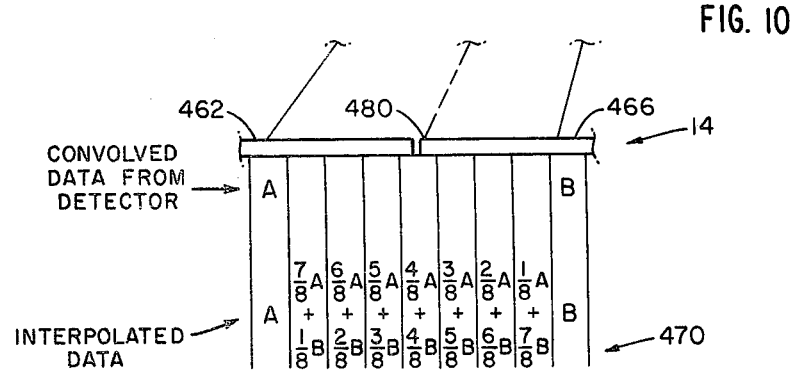
FIG. 10 is a drawing helpful in explaining the operation of the interpolator.

This is shown schematically in FIG. 10. Here, x-ray energy from x-ray tube 10 travels along a fan-shaped path around line 460 and impinges upon detector 462. Similarly, other x-ray energy travels along a fan-shaped path around line 464 and impinges upon a detector 466. If the convolved data corresponding with detector 462 is denoted as A and the convolved data for detector 466 is denoted as B, the interpolator calculates eight intermediate values which provide a linear interpolation between values A and B, as shown by values 470 in FIG. 10.

If the location of the pixels is as shown by grid 472, it can be seen that data on the density of pixel 474 is contained in the x-rays around both lines 460 and 464. In the reconstruction process, for each pixel, the appropriate value is chosen from the interpolated data points by calculating the intersection with the plane of detector array 14 of an imaginary ray, shown by dashed line 476, passing through the center of pixel 474. The point 480, at which ray 476 intersects the plane of the detector array, determines which interpolated data point is used in reconstructing pixel 474 during the back projection. The back projection process is explained in more detail below.

This particular method of providing interpolation data between the actual data from each of the projectors has the advantage of being simpler and faster than performing the interpolation as each interpolated value is required. The image memory contains 256 × 256 or 64K individual locations, one for each pixel. To perform interpolation "on the fly," as the data stored in each location in the image memory is updated, would require that 64K calculations be performed. The present method, although requiring more memory for the storage of the additional interpolated data, requires only 8 × 256 or 2K calculations, resulting in a considerable savings of time. However, it should be appreciated that the present invention may be implemented by performing the interpolation on the fly or by other means, and the following description is not to be construed as a limitation on the present invention.

The interpolator circuitry of the preferred embodiment is shown within dotted box 430 in FIG. 8. As each convolved data point is produced at the output of the convolver, it is clocked into a convolver-output memory 420 in the interpolator. Upon the calculation of the next convolved data point, the value in memory 420 is clocked into a prior-convolver-output memory 422. Thus, at any one time, memories 420 and 422 contain the convolved data representing the outputs from two adjacent detectors.

The values stored in memories 420 and 422 are applied to two inputs of a 2-channel multiplexer 424. The output from multiplexer 424 is applied to the first input of an adder circuit 426. The output from adder circuit 426 is applied to the inputs of an accumulator register 428, and the value stored in accumulator 428 is applied to the second inputs to adder 426. Interpolator control logic 430 supplies the select input to multiplexer 424 and thus determines which of the two detector outputs is applied to adder 426. Interpolator control logic 430 also supplies the clock signal to accumulator 428.

As explained above with reference to FIG. 10, the seven interpolated values between each detector outputs are respectively proportional to 1/8, 2/8, 3/8, etc. of the first detector value and 7/8, 6/8, 5/8, etc. of the second detector value. By clocking accumulator 428, interpolator control 430 causes adder 426 and accumulator 428 to perform eight additions of the values applied to adder 426 by multiplexer 424. By selectively switching multiplexer 424 during these eight additions, interpolated values composed of different weightings of the data stored in memories 420 and 422 are accumulated in accumulator 428. After eight additions have been done, interpolator control logic 430 provides a pulse on line 432 which clocks the value in accumulator 428 into the convolver/image reconstructor (C/I) memory. This signal also clears accumulator 428 in preparation for the next interpolation. This signal also is applied to the clock input of an address counter 434 which is incremented to provide the address data to the C/I memory. The interpolator need only perform eight additions for each of the eight interpolated data points, or a total of 64 operations, for each new convolved data point from the convolver. Since the convolver requires 256 convolver clock periods to produce each convolved data point, the interpolator is idle for a period following the completion of each interpolation until the next convolved data point is available, as indicated by the EOC signal 379 applied to the "data ready" input of interpolator control logic 430.

When data from the first detector is in convolver output memory 420, obviously there is no data available from a detector preceding this detector in the prior C.O. memory 422. (The monitor detector data is not used in this manner.) When the first data point is in convolver output memory 420, interpolator control logic applies a clear signal to memory 422 on line 436 to clear any random data which may be in memory 422 to avoid anomalous results from such random data. Similarly, when the data from the last detector is in prior convolver output memory 422, there will be no data available from a next detector in convolver output memory 420; and interpolator control logic applies a pulse to the clear input of memory 420 on line 438. These interpolated data points preceding the first detector and following the last detector are then calculated. In the preferred embodiment, only four interpolated data points before the first detector and four interpolated data points after the last detector are used.

A signal indicating when the last convolution has been performed is provided on line 363 by convolution number counter 362, as described above. This signal is applied to interpolator control logic 430. Twelve more interpolations must still be performed following the final convolution, and interpolation control logic 430 carries out these interpolations. When these interpolations have been completed, interpolation control logic 430 provides an interpolation done signal on line 352 which is applied to convolver control logic 316, and the convolution and interpolation processing for the present projection is finished.

Image Reconstructor

Previous methods of image reconstruction have required large amounts of time for processing the convolved data from the detector array produced during each projection. Some of these methods have required that the data from a large number of the projections be available before the processing is begun. All prior methods of doing image reconstruction have done so in a manner which requires a large amount of time for processing the data relative to the total scan time during which the data is taken.

The image reconstructor stage of the tomography processor described herein includes a pipeline processor which is capable of back-projecting data in real time as it is taken by the x-ray source and detector array and processed by the above-described processing circuitry.

In performing image reconstruction, two functions must be carried out. First, for each location in image memory, the proper data point in the C/I memory must be "located," which is the process of associating each pixel with the proper convolved and interpolated data point. (Each pixel has a corresponding location in the image memory in which data is stored representative of the density at that point of the body being scanned.) Second, the located data must be multiplied by a weighting factor, determined as described below. After these calculations have been performed, the properly weighted data is put in to the value previously accumulated at that location in the image memory. After the scan is completed and all the data from each of the projections has been taken, the values accumulated in each location in the image memory represent the density of the corresponding locations in the body being scanned. This data is then used to produce the final picture.

The preferred embodiment described herein has an image memory of 256 × 256 pixels, or 64K individual pixels and memory locations. For each of the 360 projections, one per each degree of rotation of the x-ray source and detector array, each of these pixels must be incremented by a properly weighted and located data point from C/I memory 122. This means that 256 × 256 × 360 or 23,592,960 locations and weightings must be performed for each final image. Each of these locations and weightings include a plurality of arithmetic functions which must be performed.

Figure 11:
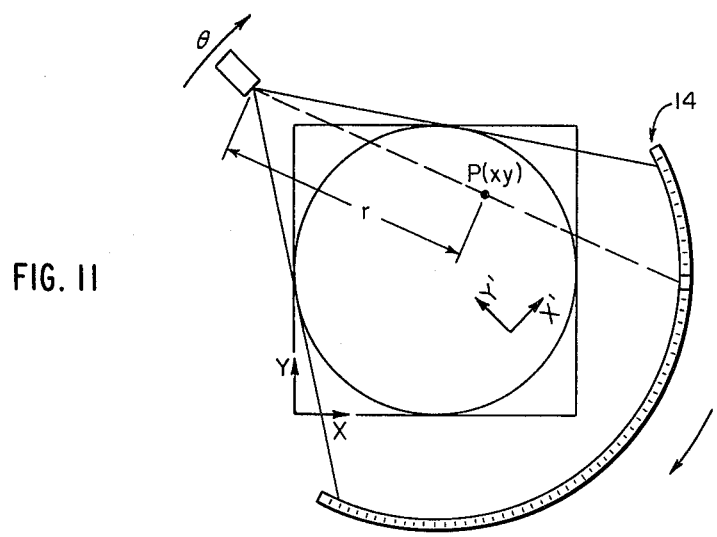
FIG. 11 shows the relationship between points in the reconstructed image and the rotating x-ray source and detector array in the patient coordinate system.

Referring to FIG. 11, the function relating each point P having coordinates x and y in the image memory with the data from a particular detector in detector array 14 for each projection angle is called the locator function and is given by:

$$L = C_1 \tan^{-1} \frac{(y \cdot \sin\theta - x \cdot \cos\theta)}{(R - y \cdot \cos\theta - x \cdot \sin\theta)} \quad (24)$$

where x and y are the coordinates in the image memory, $\theta$ is the projection angle, R is the distance from the x-ray tube to the center of rotation, $C_1$ is a constant, and L is the value of the locator function which gives the angle of the corresponding interpolated data.

As explained in the Mathematical Background description in connection with equations (13) and (23), prior to the back projection processing, the data must be properly weighted by multiplying the data by $1/r^2$ where r is the distance from the x-ray source 10 to the pixel being back-projected. The function expressing the value of $1/r^2$ is called the weighting function and is given by:

$$W = C_2 \frac{1}{(y\sin\theta)^2 + (R - y\cos\theta + x\sin\theta)^2} \quad (25)$$

where $C_2$ is a constant, W is the value of the weighting function, and the remaining terms are as identified above.

Both of these functions are comparatively complicated and time-consuming to calculate. Both require several multiplications, evaluation of trigonometric functions, and division, a very time-consuming operation. Additionally, since the relations are functions of the projection angle $\theta$, as well as of the patient system coordinates, x and y, the calculations required for each projection angle will be different.

It has been found that the weighting and locator functions can be calculated much more quickly and simply if, before these values are calculated, a coordinate transformation is carried out and the weighting and locator functions are calculated in projection system coordinates rather than in patient system coordinates. This requires an extra step for each location (pixel) in image memory — the step of converting the image memory address, which is in the patient system coordinates, into projection system coordinates. However, this transformation is relatively easy to perform, and results in a great simplification in calculating the weighting and locator functions. Once such a coordinate transformation is carried out, the locator and weighting functions are calculated in projection system coordinates as follows.

Figure 12:
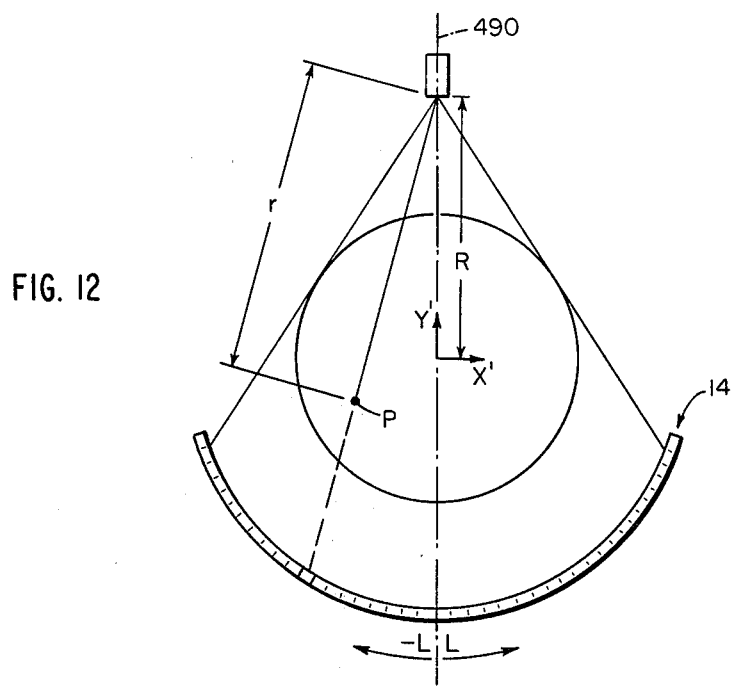
FIG. 12 illustrates the calculation of the weighting and locator functions in the projection coordinate system.

Referring to FIG. 12, it may be seen that for any pixel P, the detector receiving radiation passing through that pixel is a function only of the angle between that point and the x-ray tube axis 490. The angle may be simply expressed in the projection coordinate system by the following location function:

$$L = C_3 \tan^{-1} \frac{(x')}{(y' - R)} \quad (26)$$

where L indicates the address of the interpolated data, $C_3$ is a constant, x' and y' are the pixel coordinates in the projection coordinate system, and R denotes the distance between the x-ray tube and the center of rotation. Two very important things result from calculating the locator function in the projection coordinate system rather than in the patient coordinate system. First, the locator function is now a function of only two variables rather than three. Second, the locator function is identical for all projection angles.

Similarly, the weighting function calculation is also much simplified when expressed in the projection coordinate system. As described above, the weighting function requires that the data for each point in the image array be multiplied by $1/r^2$, where r is the distance from the x-ray tube to the image array location. Again, referring to FIG. 12, the value of $r^2$ may be simply computed using the Pythagorean theorem, and the weighting function becomes:

$$W = \frac{1}{x'^2 + (y' + R)^2} \quad (27)$$

The weighting function, when expressed in the patient coordinate system, is also a function of only two variables, rather than three, and the weighting function is the same for all projection angles.

Figure 13:
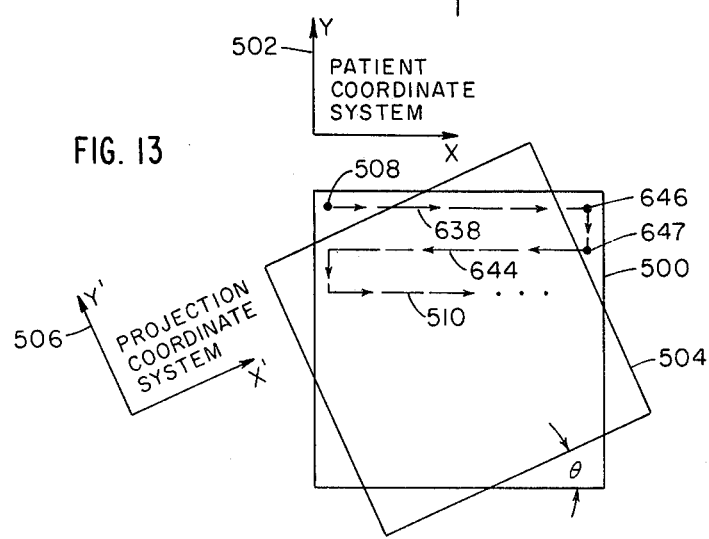
FIG. 13 shows the manner in which the image memory is updated during each projection.

Referring to FIG. 13, the area denoted by 500 corresponds with the image memory, which is oriented in the patient coordinate system shown by x and y axes 502. Each location in the image memory corresponds with one pixel into which the cross-sectional area being scanned is divided. Generally, the x-ray source 10 and detector array 14 will be oriented at an angle $\theta$ to the patient coordinate system. This is shown in FIG. 13 where box 504 and axes 506 correspond with the projection coordinate system. Coordinates in the projection coordinate frame are denoted as x' and y'. As can be seen, for each different projection angle $\theta$, a different coordinate transformation between the patient coordinate system and the projection coordinate system must be made.

In the present invention, the locations in image memory are updated sequentially while the convolved and interpolated data is accessed essentially randomly. Referring to FIG. 13, the image reconstructor begins at the first location in image memory 508 and steps sequentially through each of the memory locations, as shown by the dashed line. By stepping systematically through the image memory in this manner, the corresponding projection system coordinates x' and y', of each of the locations in the image memory, may be easily generated. Once the projection system coordinates of the first location 508 in the image memory are determined, the projection system coordinates of all the other locations in the image memory may be calculated as the processor sequentially steps through these locations by simply incrementing and/or decrementing the previous coordinates by $\Delta x'$ and $\Delta y'$ values which are constant for each projection angle. Thus, the coordinate transformation function becomes a process of iteratively updating the x' and y' values according to the following functions:

$$x' = x' \pm \Delta x' = x' \pm \delta\cos\theta \quad (28a)$$

$$y' = y' \pm \Delta y' = y' \pm \delta\sin\theta \quad (28b)$$

for increments along the x-axis in image memory, and:

$$x' = x' \pm \delta\sin\theta \quad (28c)$$

$$y' = y' \pm \delta\cos\theta \quad (28d)$$

for increments along the y-axis in image memory, where $\delta$ is the spacing between pixel centers in the image array. Each increment of x' and y' is produced by a signed addition, which may be peformed very rapidly by relatively simple hardware. The projection system coordinates of the first location 508 in image memory may be easily determined for each projection angle by a simple trigonometric calculation.

Figure 14:
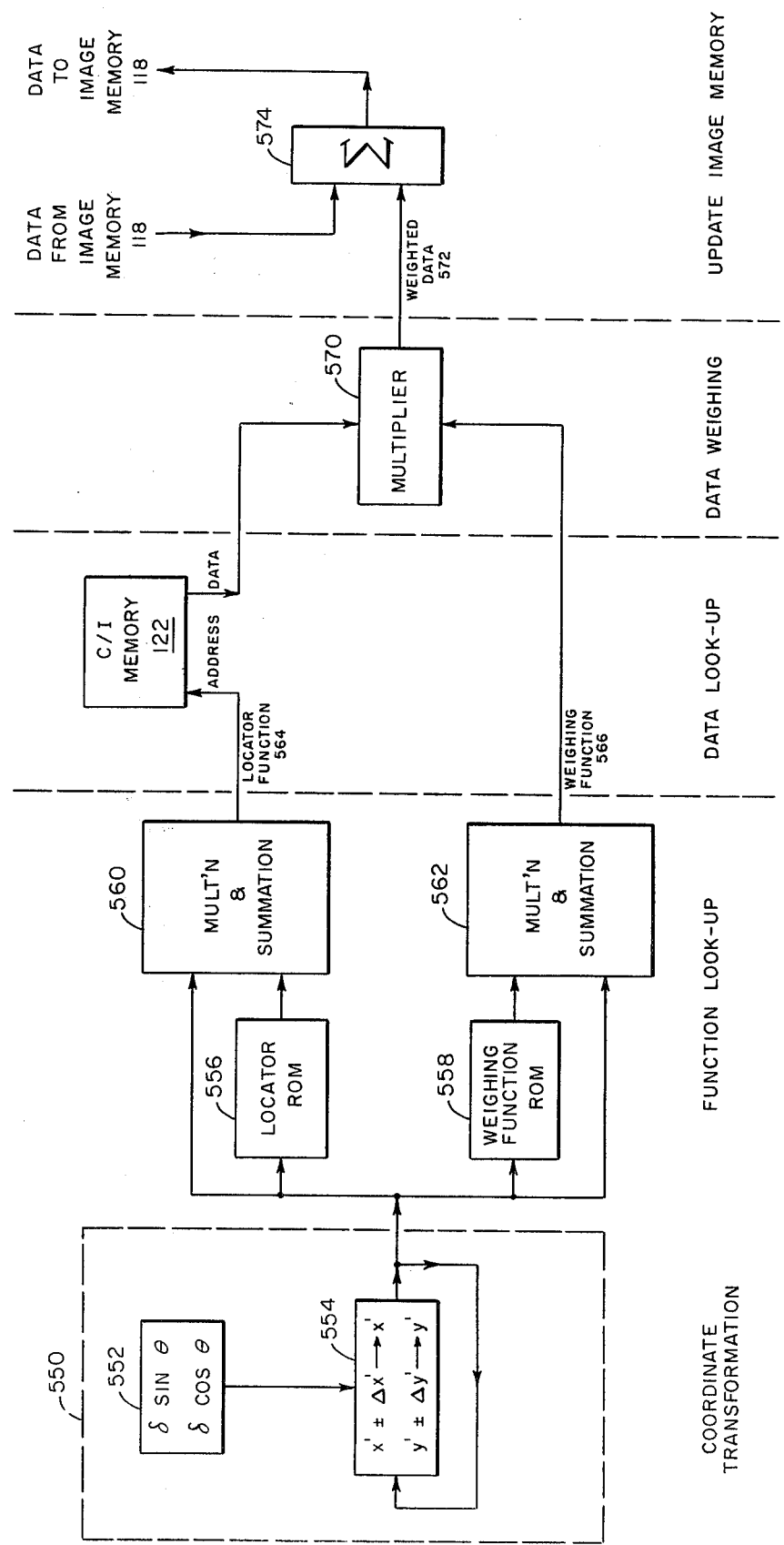
FIG. 14 is a block diagram of the image reconstructor.

A block diagram showing the steps required in the image reconstruction process of the present invention is shown in FIG. 14. Once the convoluted and interpolated data for an entire scan has been processed by convoluter and interpolation circuitry and stored in the C/I memory, the image reconstructor processing circuitry may commence operation on that set of data. The first step in the reconstruction process is performing the above-described coordinate transformation. This is shown in block 550 in FIG. 13. Before beginning the image reconstruction of the data from each projection, the $\delta\sin\theta$ and $\delta\cos\theta$ are calculated. These values only need updating once per projection, and therefore, they may be easily calculated by the control computer 130 and loaded into holding registers prior to the requirement of these values by the image reconstructor. This process is shown by block 552 in FIG. 12. During the image reconstruction process, the x′ and y′ values are updated in accordance with equations (28), as shown by block 554.

The transformed x′ and y′ coordinates are applied to two read-only memories 556 and 558. Within these read-only memories is stored data representative of the weighting function and of the locator function. As explained above, these two functions are identical for each projection, and therefore, they may be economically and rapidly calculated by means of look-up tables stored in read-only memories. Depending upon the speed and accuracy desired, all values of the weighting and the locator functions may be stored in the read-only memories. Alternatively, the read-only memories may contain compressed data tables by which the weighting and locator functions may be quickly calculated. Examples of such compressed functions would be piece-wise-linear approximations and Taylor series expansions. The preferred embodiment of the image locator described below calculates the weighting and locator functions by storing the values of these functions at many discrete points and interpolating between these points by means of two-dimensional, piece-wise linear or quadratic expansions with first order cross terms retained. Each of the read-only memories 556 and 558 in response to the x′ and y′ coordinates applied to the address inputs thereof produces at its output the weighting function or locator function value corresponding to the location denoted by the higher order bits. The expansion coefficients for the weighting and locator function are applied to multiplication and summation logic where the x′ and y′ values and cross terms are multiplied by the proper terms and the products summed to produce the locator function values 564 and the weighting function values 566.

The output from multiplication and summation circuitry 560 is the value of the locator function, and denotes which one of the 2048 interpolated values corresponds with the location in the image memory currently being processed. In other words, the locator function determines the particular interpolated data value most closely corresponding with a ray from x-ray source 10 passing through the center of the pixel corresponding with the location in the image memory being processed, as described above with reference to FIG. 10.

The locator function is applied to the address input of C/I memory 122. In response, C/I memory 122 produces at its output the proper interpolated data. This data is applied to one input of a multiplier 570. Multiplication and summation circuitry 562 produces data at its output representative of the weighting function by which the data at the point in the image memory being processed must be multiplied. The weighting function is applied to a second input of multiplier 570.

Multiplier 570, in response to the two above-described signals, multiples the convoluted data by the weighting function to produce a value 572 corresponding with the properly weighted data at its output. This weighted data value is applied to one input of a summation circuit 574. The other input to the summation circuit is the data from the image memory corresponding with the value accumulated during previous projections. Summation circuit 574 sums the weighted data from multiplier 570 with the data previously stored in image memory 118, and the resulting output from summation circuit 574 is applied to the data inputs to the image memory where it is stored, replacing the previously stored data.

The above-described sequence of processing steps is repeated for each location in the image memory. After all of the locations in the image memory have been updated, the convoluted and interpolated data from the next projection is made available to the image reconstructor, and the above process is repeated. This is done for all the data from each projection to produce the final values in image memory 118 representative of the density of the object being scanned.

Image Reconstructor — Coordinate Transformation

Figure 15:
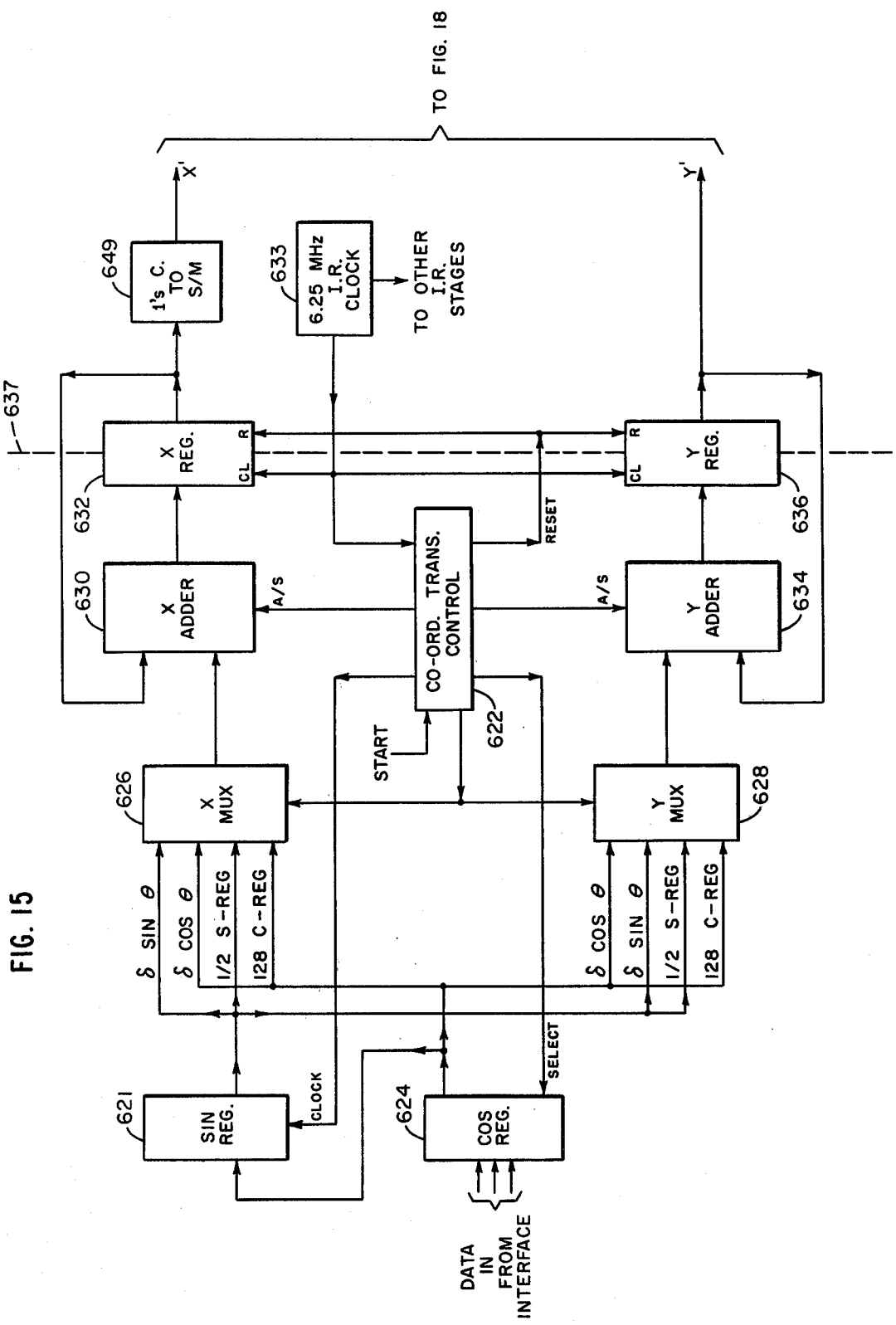
FIG. 15 shows the coordinate transformation circuitry of the image reconstructor.
Figure 19:
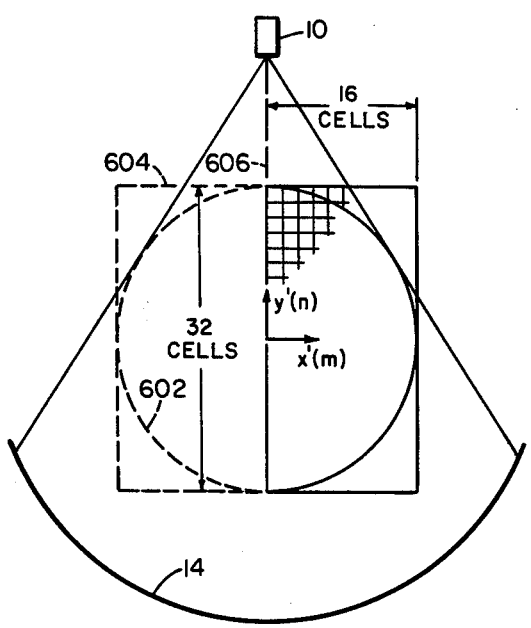
FIG. 19 shows the manner in which the final image is divided for the calculation of weighting and locating functions.

FIGS. 15 through 19 show the detailed implementation of a preferred embodiment of the image reconstructor. FIG. 15 shows the circuitry which performs the coordinate transformation function in the image reconstructor to provide the proper x′ and y′ coordinates in the projection coordinate system. For each projection, the image reconstructor sequentially updates each location in image memory. As the locations in image memory are accessed, the coordinate transformation circuitry solves equation (28) to generate the projection system coordinates of each memory location. Once the coordinate transformation has been performed, the back projection operations, carried out by the image reconstructor circuitry shown in FIG. 19, are all performed in projection system coordinates.

Referring to FIG. 15, the operation of the coordinate transformation circuitry is described. Before the reconstruction process begins, the $\delta\sin\theta$ and $\delta\cos\theta$ values from equation (28) are loaded via interface 132 into sine register 621 and cosine register 624, and the projection system coordinates of the first location in image memory are loaded into two registers denoted as X register 632 and Y register 636. The manner in which these initial values are loaded is described in detail below with reference to FIGS. 16 and 17. The sine and cosine data from registers 621 and 624 are applied to two inputs of two 4-to-1 multiplexers, denoted as X-multiplexer 626 and Y-multiplexer 628. The output from X-multiplexer 626 is applied to a first input of an adder, denoted as X-adder 630. The output from X-adder 630 is applied to X-register 632; and the output from X register 632 is applied to the second input of X-adder 630. X register 632 is clocked by a 6.25 MHz clock signal from image reconstructor (I.R.) clock 633, and by applying the appropriate signal to the add/subtract input of X-adder 630, the value accumulated in X register 632 may be incremented or decremented by the value present at the output of X-multiplexer 626. Similarly, the output from Y-multiplexer 628 is applied to a first input of an adder, denoted as Y-adder 634. The output from Y-adder 634 is applied to Y-register 636, and the output from Y register 636 is applied to the second input to Y-adder 634. The add/subtract signals to X and Y-adders 630 and 634 are provided by a coordinate transformation control circuit 622, described in detail below.

To begin the coordinate transformation process for a projection, control 622 loads the projection system coordinates of the starting point in image memory (point 508 in FIG. 13) into X and Y registers 632 and 636. Once the initial values have been loaded into the X and Y registers, the coordinate transformation is carried out by adding the proper incremental values to the previously accumulated values in the X and Y registers as each of the locations in image memory is sequentially addressed. Referring to FIG. 13 again, to provide the coordinates for the locations in the first line of image memory, shown by dotted line 638 in FIG. 13, control circuit 622 causes X-multiplexer 626 to apply the $\delta\cos\theta$ value of X-adder 630 and Y-multiplexer 628 to apply the $\delta\sin\theta$ value to Y-adder 634. The X and Y-adder outputs are clocked into the X and Y registers by the clock signal from I.R. clock 633 to provide the next x' and y' values, incremented by the proper amounts in accordance with equations (28a) and (28b). This process is continued until the last location in the first line of image memory (point 646 in FIG. 13) has been addressed. Coordinate transformation control 622 then causes X-multiplexer 626 to apply the $\delta\sin\theta$ value to X-adder 630 and Y-multiplexer 628 to apply the $\delta\cos\theta$ value to Y-adder 634, and applies a subtract signal to the add/subtract input of Y-adder 634. The next clock pulse causes the proper values to be added to the x' and y' coordinates stored in the X and Y registers corresponding to the increment between the last location in the first row of image memory and the last location in the second row of image memory, respectively points 646 and 647 in FIG. 13. Following this, control circuit 622 causes the X and Y-multiplexers to reapply the $\delta\cos\theta$ and $\delta\sin\theta$ respectively to the X and Y-adders, and provides subtract signals to the add/subtract inputs of both adders. The following clock signals from I.R. clock 633 produce the projection system coordinates of the locations in the second line of the image memory, line 644 in FIG. 13. This process is repeated until every location in the image memory has been addressed.

Cosine register 624 is a two-bank, two-port memory, such as a 74LS670 integrated circuit. This memory is essentially the same as the two-bank C/C and C/I memory, with the exception that each blank has only two locations. The $\delta\sin\theta$ data and $\delta\cos\theta$ data are loaded into the two registers in one bank of memory 624, while previously loaded $\delta\sin\theta$ data and $\delta\cos\theta$ data are available in the other bank at the output of memory 624. Control circuit 622 provides a select input to memory 624 which selects whether the sine or cosine data from the output bank is produced at the output thereof. The output from cosine register 624 is applied to a third input to both the X and Y-multiplexers, but shifted by seven bits to provide a value equal to 128 times the values stored in cosine register 624. The output from sine register 621 is applied to fourth inputs of both the X and Y-multiplexers, shifted by one bit to provide values equal to ½ the value in sine register 622.

To begin a coordinate transformation cycle for a particular projection, the coordinate transformation circuitry loads the projection system coordinates of the first location in image memory into X and Y registers 632 and 636. Control circuit 622 does this by properly providing signals to the sine and cosine registers, the X and Y-multiplexers, and the X and Y-adders and registers to cause the values given by:

$$x' = -127\tfrac{1}{2} \cdot \delta\cos\theta - 127\tfrac{1}{2} \cdot \delta\cos\theta$$
$$y' = 127\tfrac{1}{2} \cdot \delta\cos\theta - 127\tfrac{1}{2} \cdot \delta\sin\theta \qquad (29)$$

to be accumulated in each of the X and Y registers. This value corresponds to the projection system coordinates of the center of the pixel corresponding with the initial location in image memory, the center of the pixel being the result of adding or subtracting $\tfrac{1}{2}\,\delta\cos\theta$ or $\tfrac{1}{2}\,\delta\sin\theta$ factors.

Referring to FIG. 15, the control circuitry 622 is shown in detail. The control circuitry is sequenced by a 4-bit sequence counter 800, such as a 74161 integrated circuit. The 6.25 MHz clock signal from I.R. clock 633 is applied to the clock input of counter 800. The carry output from counter 800 is applied through inverter 804 to an enable input of the counter. The carry output goes high when the counter reaches 15 (the 1111 state), disabling the counter and preventing it from being further incremented by the clock signal until it is reset. An I.R. BUSY signal from interface 132 is applied to a flip-flop 806 which is clocked by clock 633 to synchronize the I.R. BUSY signal with the image reconstructor clock. The synchronized I.R. BUSY signal from flip-flop 806 is applied to a preset enable input to counter 800. The preset inputs to counter 800 are connected so that the value 7 (0111) is loaded into the counter by the preset enable input.

Prior to beginning an image reconstruction cycle, the I.R. BUSY signal from interface 132 is high, maintaining counter 800 in the 7 state and preventing it from being incremented by the signal from clock 633. To begin an image reconstruction cycle, interface 132 caues the I.R. BUSY signal to go low. Counter 800 then starts counting, sequencing through states 7 through 15. Once the counter reaches the 15 state, the carry output inverted by inverter 804 disables the counter, and counter 800 remains in the 15 state until the I.R. BUSY signal returns high at the end of the image reconstruction cycle for a particular projection. Thus, counter 800 defines several states at the beginning of the image reconstruction for each projection, and it is during these initial states that the initial values are loaded into X register and Y register 632 and 636.

The Q3 and Q4 outputs from counter 800 are applied to an AND gate 808. The output of AND gate 808 is applied to an enable input of a 7-bit counter 810. Counter 810 is clocked by the signal from I.R. clock 633. When counter 800 reaches state 12, the output from AND gate 808 goes high, and counter 810 is enabled. Counter 810 is then incremented by each of the following clock pulses from I.R. clock 633. Counter 810 counts the locations in each row of image memory and provides a signal at its carry output when it reaches state 255. This signal denotes the end of a line (EOL) in image memory. The EOL signal is applied to a flip-flop 812 which is clocked by the I.R. clock 633 and changes state at the end of each line. The output from flip-flop 812 provides an indication of whether an odd or even line is being reconstructed.

Figure 16:
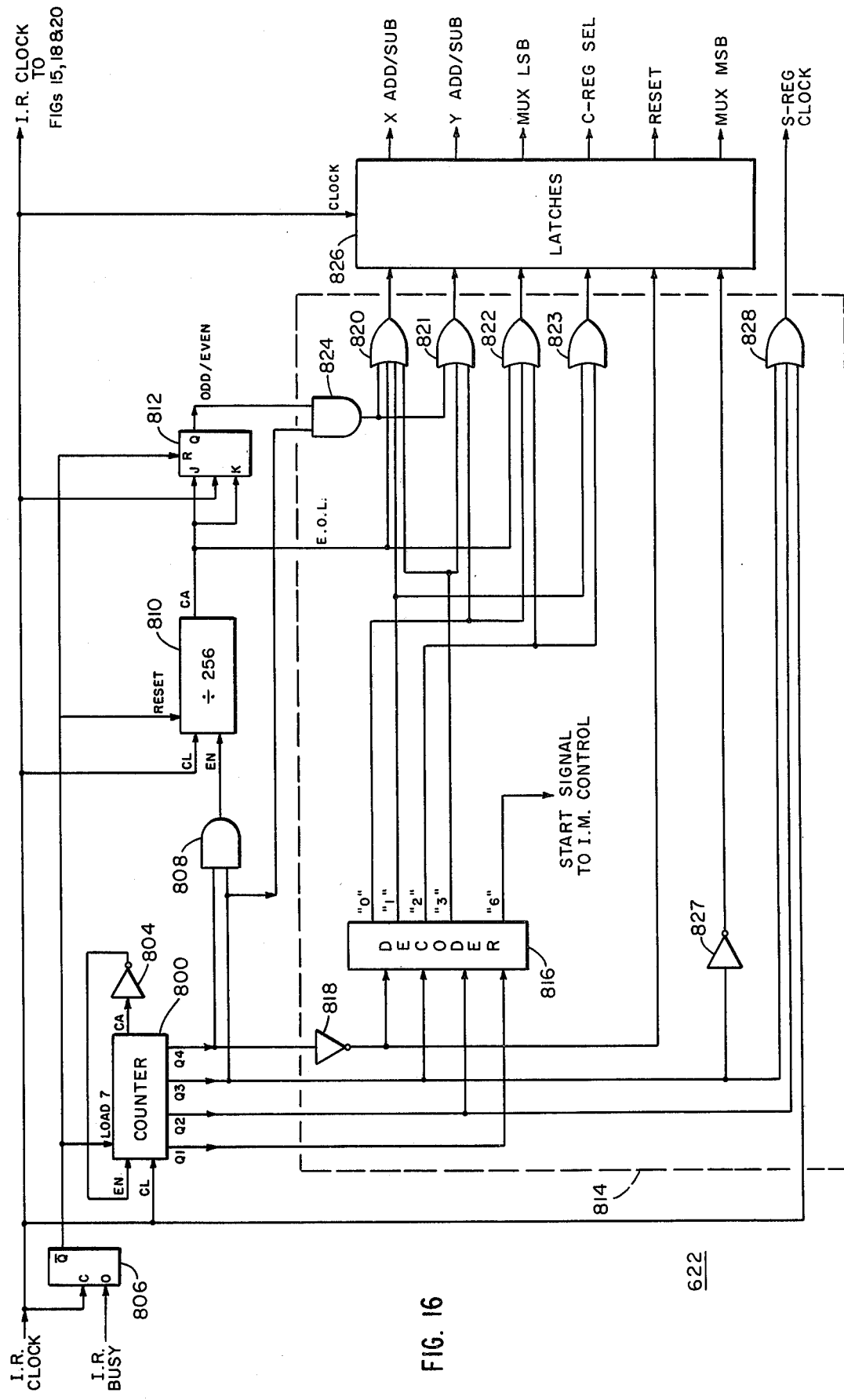
FIG. 16 shows the coordinate transformation control circuit shown in FIG. 15.

The outputs from counter 800, the EOL signal, and the odd/even line signal are applied to the combinational logic enclosed within dotted box 814 which decodes these signals to provide the output signals from control circuit 622. The three least significant bits from counter 800 are applied to decoder 816 and the fourth bit is inverted by inverter 818 and applied to decoder 816. Decoder 816 is a 10-state decoder, such as a 74LS42 integrated circuit. Due to the inversion of the fourth bit from counter 800 by inverter 818, the four inputs to decoder 816 go from states 15 through 7 as the counter cycles through states 7 through 15. Decoder 816 has 10 outputs, one of which is high in response to a BCD encoded input ranging from 0 to 9. For values greater than 9, all 10 outputs from decoder 816 are low. The "0" through "3" outputs from decoder 816 are applied to OR gates 820–823, as shown in FIG. 16, to provide the outputs described below. Additionally, the EOL signal and the odd/even line signal from flip-flop 812 are applied to combinational logic 814. The odd-/even signal is gated by the third bit from counter 800 via AND gate 824.

Combinational logic 814 produces the following signals. OR gate 820 produces the add/subtract signal applied to X-adder 630. OR gate 621 produces the add-/subtract signal applied to Y-adder 634. OR gate 622 provides the least significant bit of the two-bit select signal applied to X and Y-multiplexers 626 and 628. OR gate 623 provides the select signal applied to cosine register 624. The inverted Q4 output of counter 800 from inverter 818 provides the reset signal used to reset X and Y registers 632 and 636. The Q3 output from counter 800 is inverted by inverter 827 to provide the most significant bit of the two-bit select signal applied to X and Y-multiplexers 626 and 628. The above-described signals are applied to latches 826 into which they are clocked by the clock signal from I.R. clock 633 for application to the remainder of the coordinate transformation circuitry, as shown in FIG. 15. The clock signal for sine register 622 is provided by gating the clock signal from clock 802 with the Q2 and Q3 outputs from counter 800 in OR gate 828.

The "6" output from decoder 816 is applied to the image memory control circuitry 748, described below, and causes the image memory control to start cycling through image memory. The use of the "6" output from decoder 816 compensates for the delay as the data is clocked through the various pipeline stages of the image reconstruction circuitry and image memory.

Figure 17:
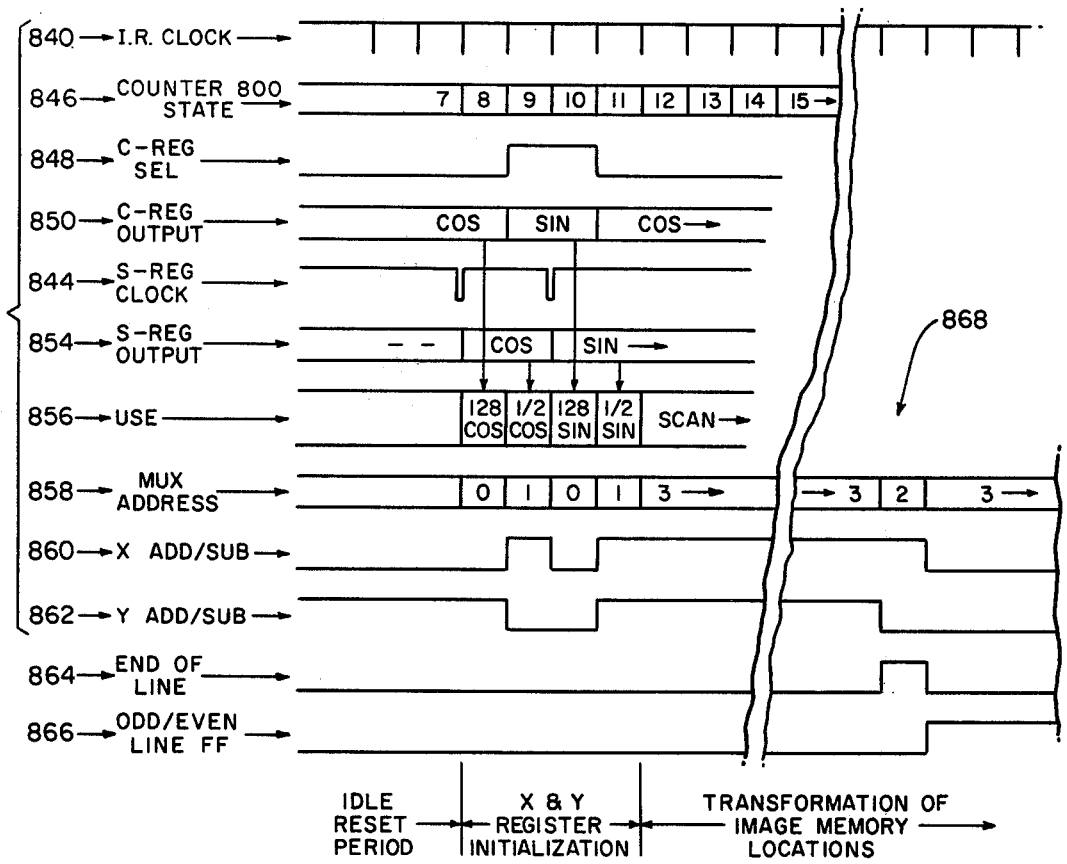
FIG. 17 are waveforms helpful in explaining the operation of the coordinate transformation circuitry.

Referring to the waveforms shown in FIG. 17, the operation of the coordinate transformation circuitry of FIG. 15 is described in detail. Waveform 840 is representative of the signal from I.R. clock 633. While the clock signal is shown here as a narrow pulse, it will be appreciated that other clock signals, such as square-waves, can equally well be used. To begin the image reconstruction process, interface 132 causes the I.R. BUSY signal to go high. In response, the output from flip-flop 806 goes low. Counter 800, which has previously been held in the seven state by the output from flip-flop 806 is now incremented by the following clock pulses. Counter 800 sequences through each state until it reaches 15, where it is held by the inverted carry output applied to the enable input of counter 800, as described above. The counter states are shown in line 846. (Note that because of the one-bit delay in signals 848 through 862 due to latch 826, the counter states are offset by one bit from their actual occurrence to simplify the present explanation).

The cosine register select input from gate 823 is shown in line 848 and the resultant data present at the output of cosine register 624, $\delta\cos\theta$ or $\delta\sin\theta$, is indicated in line 850. The clock signal applied to sine register 621 by OR gate 828 is shown by waveform 844. The output from cosine register 624 is applied to the input of sine register 621 and thus, the sine register clock signal 852 clocks the data present at the output of the cosine register, shown by waveform 850, into the sine register. The resulting output from sine register 621 is shown by waveform 854.

The select inputs to X and Y-multiplexers 626 and 628 select the multiplexer inputs as indicated in line 858. The multiplexer inputs are denoted as "0" through "3," as shown in FIG. 15. During the X and Y register initialization period, the X and Y-multiplexers alternately select the inputs corresponding to 128 times the cosine register output and ½ times the sine register output, as shown in FIG. 17. The X and Y add/subtract signals are produced by control circuit 622 in accordance with waveforms 860 and 862. The result of this operation is that the proper projection system coordinates of the initial location in image memory, as given by equation (29) above, are accumulated in X and Y registers 632 and 636 during the first four I.R. clock periods following the I.R. BUSY signal going high.

Following the X and Y register initialization, the coordinate transformation circuit increments the values in X and Y registers by the proper amounts, as described above. At the end of a line, the EOL signal from counter 810 goes high, providing an indication thereof; and at the beginning of the following line, the odd/even output from flip-flop 812 changes state, indicating whether the line is odd or even. The EOL and odd-/even signals are shown by waveforms 864 and 866. The operation of control circuitry 622 at the end of the first line is shown by the waveforms in the area designated 868, and the multiplexer address values and X and Y add/subtract signals shown result in the proper addition of values, as described above.

Image Reconstructor-Back Projector

Figure 18:
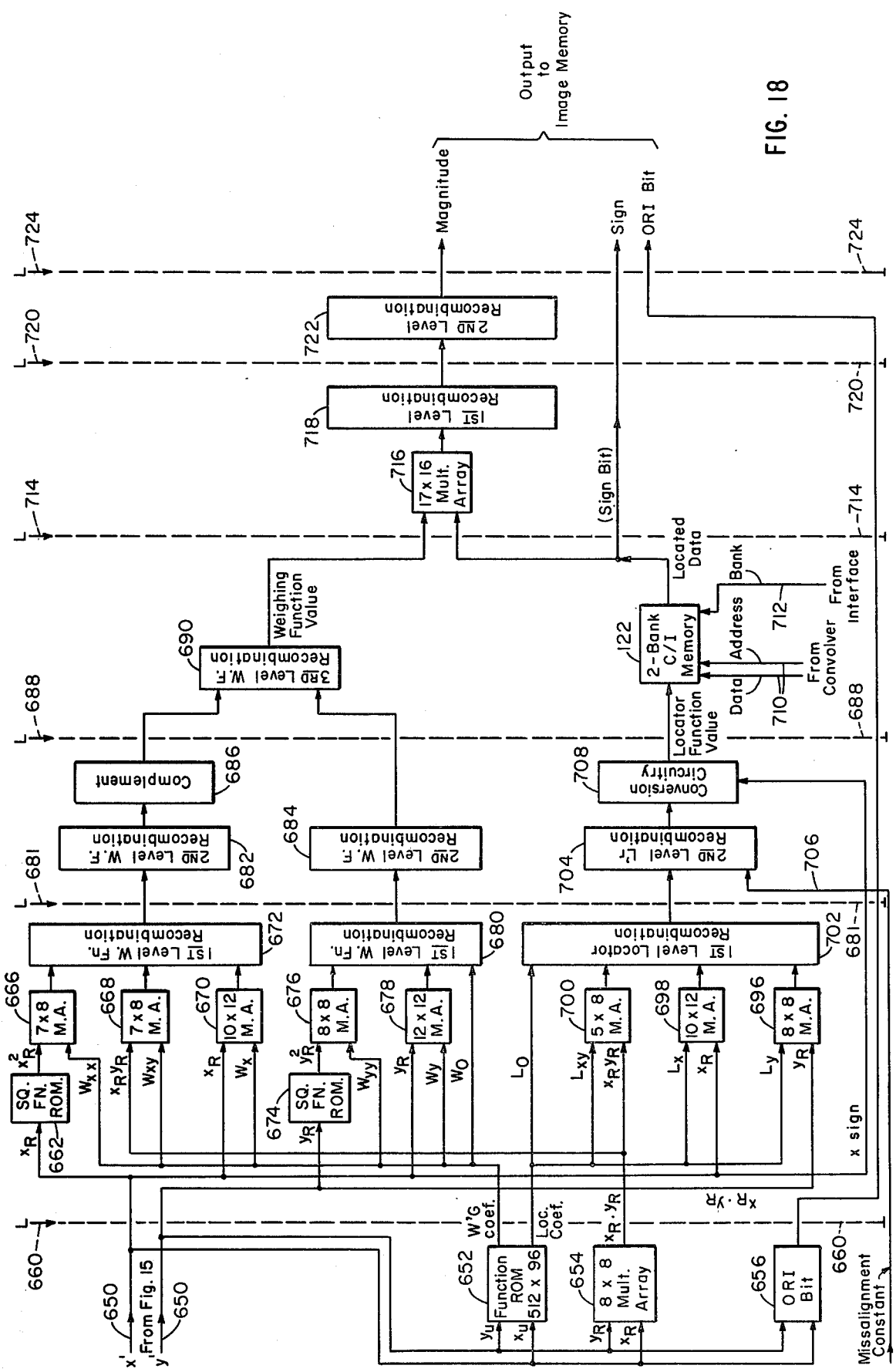
FIG. 18 shows the back projection circuitry of the image reconstructor.
Figure 20:
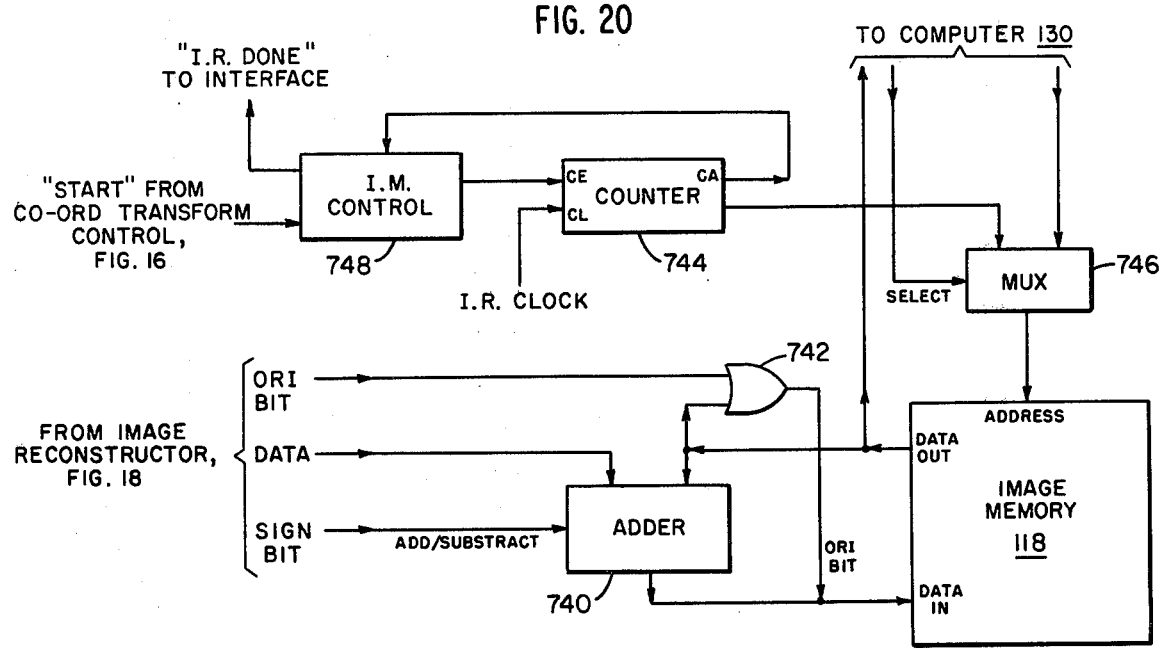
FIG. 20 shows the image memory.

FIG. 18 and the accompanying description below disclose in detail one preferred embodiment of the back projection circuitry of the image reconstructor. In order to economically and rapidly compute the values of the locator and weighting functions, two-dimensional expansions are used to generate these functions over the image space. These expansions are performed within 512 sub-areas, called cells, arranged in a rectangular array; 32 cells in the direction parallel to the central x-ray beam and 16 cells perpendicular to this direction.

This is shown in FIG. 19. Here, the circular area 602, corresponding with the final image, is shown circumscribed by a square area 604. While data in the corners of the square 604 will eventually be eliminated as being outside the final image, the back projection circuitry is much more easily implemented in a manner which scans the entire square area 604 during each projection. Area 604 is sub-divided into 1,024 square sub-areas called cells, 32 cells on a side. Due to the fact that both the weighting function and locator function are symmetrical for positive and negative x' about the center ray 606 from x-ray source 10, the values of these functions will be identical for positive and negative x'. Therefore, the locator and weighting values need only be stored for the 512 cells composed of the 16 × 32 cell array lying to the right of center line 606.

In computing the weighting function for a location having projection system coordinates x' and y', each of these coordinates is divided into a most significant part of five bits and a least significant part containing the remaining bits. The five-most significant bits of the y' coordinate and the four-most significant bits of the x' coordinate (ignoring the sign bit, as discussed above) uniquely identify which one of the 512 cells the point lies in. The most-significant parts of the x' and y' coordinates are respectively denoted as m and n. The remaining least-significant bits of the x' and y' coordinates locate where within a particular cell (m,n) the point is located; and these lesser significant bits, called the residue, are denoted by $x_R$ and $y_R$. The weighting function is calculated using the following formula:

$$W = W_O(m,n) + W_x(m,n) \cdot x_R + W_y(m,n) \cdot y_R + W_{xy}(m,n) \cdot x_R \cdot y_R + W_{xx}(m,n) \cdot x_R^2 + W_{yy}(m,n) \cdot x_R^2 \quad (30)$$

where m and n are the coordinates of the cell, m ranging from 1 to 16 and n ranging from 1 to 32, and the subscripted W values are the expansion coefficients for cell (m,n). Equation (30) requires that six constants be stored for each cell, namely $W_O(m,n)$, $W_x(m,n)$, $W_y(m,n)$, $W_{xy}(m,n)$, $W_{xx}(m,n)$, and $W_{yy}(m,n)$. These constants are stored in a large read-only memory with 512 locations and 60 bits at each location.

The locator function is calculated using the equation:

$$L = L_O(m,n) + L_x(m,n) \cdot x_R + L_y(m,n) \cdot y_R + L_{xy}(m,n) \cdot x_R y_R \quad (31)$$

where L is the value of the locator function, m and n are the coordinates of the cell, and the subscripted L values are the expansion coefficients for cell (m,n). The locator function is a smoother and less rapidly changing function than the weighting function, and consequently, only first order terms plus one cross term is required in the expansion to provide the desired accuracy. The four expansion coefficients for each cell, $L_O(m,n)$, $L_x(m,n)$, $L_y(m,n)$, and $L_{xy}(m,n)$ are stored in a read-only memory having 512 locations and 36 bits at each location.

The projection system coordinates, x' and y', from the coordinate transformation circuitry of FIG. 14 each consist of 18-bit values. These x' and y' values are applied to the back projection circuitry shown in FIG. 18. The data is further divided into "upper" and "lower" groups. The upper groups include the five most significant bits of sign and magnitude information and correspond with the m and n cell coordinates described above. These values are denoted by $x_U$ and $y_U$. The lower groups correspond with the residues described above and include the 12 least significant digits. The residues are denoted by $x_R$ and $y_R$.

Five bits of the $y_U$ value and four bits of the $x_U$ value (not including the sign bit) are applied to a read-only memory (ROM) 652. ROM 652 is a 512 × 96 memory. Due to the symmetry of the weighting and locating functions for positive and negative values, the sign of the x' coordinate is not required in performing the weighting and locating functions. ROM 652 contains the values of the weighting and locating function coefficients for each of the cells. In response to the $x_U$ and $y_U$ values applied to its address inputs, ROM 652 produces at its outputs 60 bits of weighting function coefficients and 36 bits of locator function coefficients.

The eight most significant bits of each of the $x_R$ and $y_R$ values are applied to a multiplier 654. Multiplier 654 is an 8 × 8 multiplier which provides an 8-bit value at its output equal to $x_R \cdot y_R$, which is used in calculating the cross terms in the weighting and locator functions. The over-range bits of each of the x' and y' values are applied to out-of-reconstructed-image (ORI) logic 656. In response to either over-range bit being positive, the ORI bit output from logic 656 goes high, indicating that the value being processed lies outside the final image produced by the tomography processor. The ORI bit is passed through the image reconstructor and applied to image memory, as described below, so that these values outside the final reconstructed image are not displayed. The outputs from ROM 652, multiplier array 654, ORI bit logic 656, and the $x_R$ and $y_R$ values are clocked into pipeline latches, denoted by dotted line 660, where these values are held for processing by the next stage of the pipeline processor.

The multiplying arrays and Wallace tree recombination circuitry called for below are similar to those used and described above with reference to the convolver circuitry. Both the multiplying arrays and the recombination circuitry are well-known to those in the art, and reference should be made to the Texas Instruments, Inc. reference cited above for further details concerning the type of multiplier circuitry.

The next three stages of the pipeline processor perform the multiplication of the x' and y' values by the coefficients stored in ROM 652 to calculate the locator and weighting functions in accordance with equations (30) and (31).

The $x_R$ value is applied to a square function ROM 662 which produces an 8-bit output equal to the square of the input. The $x_R^2$ output from ROM 662 is applied to one input of a multiplier array 666. The other input to multiplier array 664 is a 7-bit value from ROM 652 which is the $W_{xx}$ coefficient of the second-order $x_R^2$ term in the weighting function expansion. Multiplier array 666 is a 7 × 8 multiplier array, and in response to the inputs thereto, produces the $W_{xx} \cdot x_R^2$ term of equation (30).

The 8-bit $x_R \cdot y_R$ output from multiplier 654 is applied to one input of a 7 × 8 multiplier array 668. The $W_{xy}$ coefficient from ROM 652 is applied to the second input of multiplier 668 which produces the appropriate term at its output. The 12-bit $x_R$ value is applied to one input of a 10 × 12 multiplying array 670. A 10-bit $W_x$ value from ROM 652 is applied to the other input of multiplying array 670 which produces the corresponding term at its output. The three outputs from multiplying arrays 666, 668, and 670 are applied to first-level weighting function recombination circuitry 672 which provides the first stages of recombination of the inputs applied thereto.

The $y_R$ value is applied to a second square function ROM 674 which produces a $y_R^2$ value at its output. The $y_R^2$ value is applied to one input of an 8 × 8 multiplying array 676 which multiplies it by an 8-bit $W_{yy}$ value from ROM 652. A 12 × 12 multiplying array 678 multiplies the 12-bit $y_R$ and $W_y$ values applied to its input to produce an output representative of the corresponding term of the weighting function in equation (30).

The outputs from multiplying arrays 676 and 678 are applied to a second, first-level weighting function recombination circuitry 680. Also, a 16-bit $W_O$ value equal to the zeroth-order coefficient of the weighting function expansion for the image array cell in question is applied to first-level weighting function recombination circuitry 680.

The output from first-level weighting function recombination circuits 672 and 680 are clocked into pipeline latches 681 where they are held for processing by second-level recombination circuits 682 and 684. Due to the characteristics of the weighting function, the three terms of equation (30) applied to first-level recombination circuitry 672 will always be negative, and the two terms applied to first-level recombination circuit 680 will always be positive. These terms are most conveniently handled by performing the first and second levels of recombination separately for the positive and negative terms and applying the output of second-level recombination circuit 682 to complementing circuit 686 to negate the output of second-level recombination circuit 682. The outputs of complementing circuit 686 and recombination circuit 684 are held in pipeline latches represented by dashed line 688, and these values are applied to a third-level weighting function recombination circuit 690. The output from recombination circuit 690 is the value of the weighting function.

The locator function is calculated in the same manner as is the weighting function. Due to the lesser complexity of the locator function, only two levels of recombination and two pipelines stages are required. The convolved data stored in C/I memory 122 is recalled by the locator function during the pipeline stage required by the third-level recombination circuitry of the weighting function calculation.

To calculate the locator function, eight bits of the $y_L$ value and an 8-bit $L_y$ value are applied to an $8 \times 8$ multiplying array 696, and all 12 bits of the $x_R$ value and a 10-bit $L_x$ value are applied to a $10 \times 12$ multiplying array 698 to produce the first order terms of the locator function. The different number of bits in the first order $x'$ and $y'$ values and coefficients results from the fact that the first derivative of the locator function is larger in one direction than in the other; and the described number of bits are required in order that the final locator function have the required precision.

The $x_R \cdot y_R$ value from multiplier array 654 is applied to one input of a $5 \times 8$ multiplying array 700. A 5-bit $L_{xy}$ value from ROM 652 is applied to the other input of multiplying array 700. The outputs from multiplying arrays 696, 698, and 700 and a 13-bit $L_O$ value equal to the zeroth order term of equation (31) are applied to first-level locator recombination circuitry 702.

The outputs from first-level locator recombination circuitry 702 are clocked into pipeline latches 681 and applied to second-level recombination circuitry 704. Additionally, a misalignment constant is applied, from computer 130 via interface circuit 132, on line 706 to second-level locator recombination circuitry 704. This constant may be used to add a value to the locator function to compensate for mechanical misalignment of the detector array. The zeroth-order locator coefficient, $L_O$, from ROM 652 has a constant factor equal to two detector spacings subtracted therefrom. Thus, the misalignment constant may compensate for positive and negative misalignments without the necessity of having a signed addition for the misalignment constant.

The output from second-level locator recombination circuitry 704 is applied to conversion circuitry 708. The $x'$ sign bit is also applied to conversion circuitry 708. As described above, the locator function is symmetrical for positive and negative values of $x'$. The sign bit of the $x'$ value from the coordinate conversion circuitry is not used in the above-described calculations, but rather is applied to conversion circuitry 708 to provide an output of the proper sign. As described above in the explanation of the coordinate transformation circuitry, the $x'$ value is calculated in sign/magnitude representation. Conversion circuitry 708 converts this sign/magnitude representation to a 2's complement representation. This value may then be negated or not by inverting or not the bits of the output from second-level recombination circuit 704, according to the value of the sign bit. The output from conversion circuitry 708 is the locator function value and is clocked into pipeline latches 688.

It should be noted that the $x'$ sign value, though not processed in the first two stages of the pipeline processor shown in FIG. 16, is still clocked into the latches 660 and 681 between these stages so that these values will advance through the pipeline processor synchronously with the associated data being processed in each of the stages. The misalignment constant, being a constant, does not change and thus does not need to be clocked through the pipeline latches.

The locator function value in latches 688 is applied to the C/I memory 122. C/I memory 122 operates in exactly the same manner as C/C memory 120, described in detail and shown in FIG. 7, with the exception that the C/I memory banks each include 2,048 18-bit words. In response to the locator function value applied to its read-address inputs, C/I memory 122 produces at its output the proper data point from among the 2,048 convolved and interpolated data points stored therein. The data accessed by the image reconstructor in performing each back projection is loaded into C/I memory 122 during the previous projection by convolver 114 via data and address lines 710, as shown. The bank currently accessed by the image reconstructor is determined by the signal applied to C/I memory 122 on line 712 from interface 132.

The weighting function value from third-level weighting function recombination circuitry 690 and the located data from C/I memory 122 are clocked into pipeline latches 714 where the data is applied to the inputs of a $17 \times 16$ multiplier array 716. This multiplier array and the subsequent Wallace tree recombination stages are similar to those described above. The weighting function value is equal to $1/r^2$ and is always positive. Thus, the sign of the product of the weighting function and located data is determined solely by the sign of the located data. Therefore, the sign bit of the located data need not be applied to multiplier array 716. The outputs from multiplier array 716 are applied to a first-level recombination circuit 718 which includes the first stages of the Wallace tree recombination logic. The outputs from recombination circuitry 718 are clocked into pipeline latches denoted by dashed lines 720 where they are held for processing by the stage in second-level recombination circuitry 722 in the next pipeline stage.

The output from the second-level recombination circuitry 722 is clocked into latches represented by line 724. This data represents the magnitude of the value to be stored in the image memory. The sign bit is provided directly from C/I memory through latches 714, 720, and 722. The ORI bit from ORI logic 656 is also applied to image memory; and this bit is clocked through the latches between each stage of the pipeline processor so that it will proceed through the pipeline stages in synchronism with the data to which it applies.

Image Memory

The image memory and associated circuitry are shown in FIG. 17. The data from multiplying array 716 is applied to one input of an adder circuit 740. The sign bit of the located data from C/I memory 122 is applied to the add/subtract input of adder 740. The second input to adder 740 receives data from image memory 118. As the image reconstructor steps through the locations in image memory 118, the data previously accumulated in each location of image memory is applied to the second input of adder 740. To this data is added or subtracted the data from the present projection, and the resulting sum from adder 740 replaces the previous data accumulated in the presently accessed locations in image memory 118. The ORI bit from the present projection is applied to one input of an OR gate 742. The ORI bit stored in image memory 118 is applied to a second input of OR gate 742, and the output of OR gate 742 is stored in image memory 118 as the ORI bit associated with the new data from adder 740. Thus, once the image reconstructor determines that a location in image memory is out of the reconstructor image, a positive ORI bit denoting this condition is stored in memory 118, and this positive ORI bit is maintained with each subsequent updating of the image memory data accumulated in that location due to the operation of OR gate 742.

The address information for image memory 118 is produced by a 16-bit memory address counter 744. During a scan, the values of counter 744 are applied to one input of a 16-channel 2-to-1 multiplexer 746 which selects the inputs to the address inputs of image memory 118. After a scan has been completed, the data in image memory 118, representative of the final reconstructed image, is read by computer 130 or other display device which provides a signal to the select input of multiplexer 746 and applies address data to the second inputs to multiplexer 746. To read the stored data, the select input is changed so that address information is applied to the address inputs of image memory 118 and the data is produced at the data outputs in response thereto.

Address counter 744 is controlled by an image memory control circuit 748. To begin the image reconstruction for a projection, the computer interface 132 applies a signal to the control circuit 622 of the previously-described coordinate transformation circuitry. Control circuit 622 calculates the projection system coordinates of the initial location in image memory, as described above with reference to FIG. 14. When this has been done, control circuit 622 applies a start signal to image memory control 748 and proceeds to step through image memory in the manner described above. In response to the start signal from the coordinate transformation circuit, image memory control 748 enables counter 744 which is then incremented by the 6.25 MHz clock signal from I.R. clock 633; and thus, counter 744 supplies the proper address data to image memory 118.

As explained above, the coordinate transformation circuitry contains only a 2-line counter 640. The end of the image reconstruction process is determined by counter 744. When counter 744 has reached the last location in image memory 118, it applies a signal representative thereof to image memory control 748. In response to this signal, the image memory control disables counter 744 and sends an I.R. DONE signal to interface 132. In response to this I.R. DONE signal, interface circuit returns the I.R. BUSY signal to a low state, indicating that the image reconstruction process for the present projection is complete.

Interface

Figure 21:
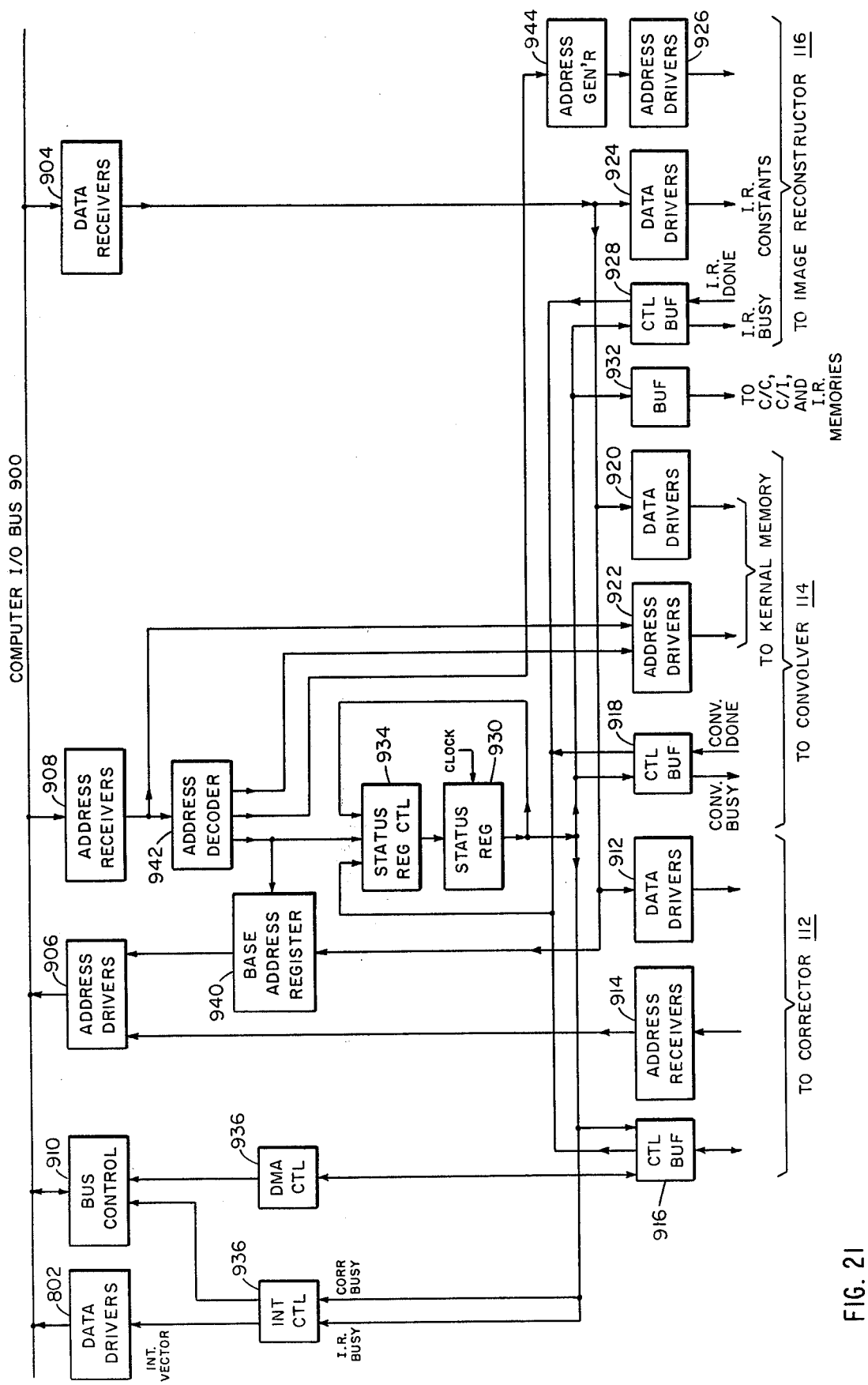
FIG. 21 shows the interface circuit of FIG. 2.

FIG. 21 is a block diagram of the circuitry within interface 132. As stated above, in the preferred embodiment, computer 130 is implemented by means of a Digital Equipment Corporation PDP-11 Computer. This computer has a bi-directional bus type of I/O interfacing configuration. The exemplary interface circuitry shown in FIG. 21 is adapted for use with the PDP-11; however, it should be appreciated that this interface could be easily adapted by one of ordinary skill in the art for use with other computers. The detailed implementation of the various control signals necessary to properly interface with the computer is discussed in detail in the PDP-11 Peripherals Handbook, published by the Digital Equipment Corporation, 1975, chapters 5 and 6.

Referring to FIG. 21, communication to and from computer 130 takes place over a computer I/O bus 900. This bus includes bi-directional data lines, bi-directional address lines, and various control lines needed for the proper operation of the computer I/O circuitry. Connected to bus 900 are data drivers 902 and data receivers 904 for sending data to and receiving data from the computer, address drivers 906 and receivers 908 for sending and receiving address data from the computer, and bus control circuitry 910 which receives from and applies to bus 900 the various signals necessary for proper interfacing with the computer. For further details of these signals and exemplary structure of bus control 910, see the above-referenced Digital Equipment Corporation interfacing handbook.

The interface contains separate drivers and receivers for the data and other necessary information transmitted to and received from the corrector, convolver, and image reconstructor sections of the processor.

Data is transferred to corrector 112 via data drivers 912. The address data from the corrector, designating the address of the required data in the memory of computer 130 is applied to interface 132 by the corrector via address receivers 914. Control signals to and from the corrector go through control buffers 916. These signals are described in more detail in the description of the corrector operation with reference to FIG. 6.

The data to and from convolver 114 goes through buffer and driver circuits 918–922. The CONV. BUSY signal to the convolver and the CONV. DONE signal from the convolver go through control buffers 918. The kernal data representating the deblurring function is loaded from computer 130 into the kernal memory of the convolver prior to the beginning of a tomographic scan, and this data is applied to the kernal memory through data drivers 920. The address inputs to the kernal memory are applied to address drivers 922. The select input to the kernal memory address multiplexer is supplied through address drivers 922 in response to a signal from decoder 942.

For each new projection, the computer must provide new reconstruction constants to the image reconstructor. These image reconstruction constants are applied through data drivers 924. Data indicating which constant is being presently provided is applied to the image reconstructor through address drivers 926. The I.R. BUSY signal to and I.R. DONE signal from the image reconstructor go through control buffers 928.

An address decoder 942 receives address data from computer bus 900 via address receivers 908. In response to the appropriate address data, address decoder 942 provides a clock signal to base address register 940 which loads, from computer 130 via data receivers 802, the base address of the corrector data stored in the computer. Address decoder 942 also provides signals to an image reconstructor address generator 944. In response to the proper address information, address generator 944 indicates which of the several image reconstruction constants are being currently provided by the computer and provides the proper signals to drive address drivers 926.

Information indicating the status, busy or idle, of the various sections of the processor is contained in a status register 930. These status bits include the following. A CORR. BUSY bit indicates the status of the corrector. This bit is applied to the corrector through buffers 916, and the transition of this bit from low to high causes the corrector to begin processing data from a completed projection. A CONV. BUSY bit indicates the status of the convolver. This bit is applied to the convolver via buffers 918, and the transition of this bit from low to high causes the convolver to begin processing previously corrected data stored in the C/C memory. An I.R. BUSY signal indicates the status of the image reconstructor. This bit is applied to the image reconstructor through buffers 932, and the transition from low to high of this bit causes the image reconstructor to begin processing the convolved data stored in C/I memory 122. A C/C memory status bit controls the state of the two-bank C/I memory, and a C/I status bit controls the state of the two-bank C/I memory. An image reconstructor memory status bit controls the state of the two-bank memory 624 in the image reconstructor containing the sine and cosine data. These memory status bits are applied to the appropriate memories via buffers 932.

The state of each of the status bits in status register 930 is controlled by status register control circuit 934. The inputs to status register control circuit 934 are the CORR. DONE signal from the corrector, the CONV. DONE signal from the convolver, the I.R. DONE signal from the image reconstructor, the outputs of the status registers, and the signal from decoder 942 which causes the base address to be loaded from computer 130 into base address register 940. In response to this, combinational logic in status register control 934 signals which are clocked into status register 930 to change the state of the bits in status register 930 in the following manner. In response to a CORR. DONE or CONV. DONE signal from the corrector or convolver stage, the status register control waits (if necessary) until the following stage is not busy, as shown by the appropriate CONV. BUSY or I.R. BUSY bit from the status register, and provides signals to the status register which, on the next clock pulse, (1) set the done stage status bit to not busy, (2) switch the following stage status bit to busy to start the stage, and (3) change the status bit of the C/C or C/I memory between the units to switch its state. In response to an I.R. DONE signal from the image reconstructor, the status register control changes the I.R. BUSY bit to not busy and changes the image reconstructor memory status bit. The CORR. BUSY bit is set to start the corrector in response to the loading of a base address into register 940, as indicated by a signal from address decoder 942.

The CORR. BUSY and I.R. BUSY signals from status register 930 are applied to an interrupt control circuit 936. In response to changes in these signals from high to low, interrupt control 936 provides a signal to bus control circuitry 910 to to send an interrupt to computer 130. Interrupt control 936 also generates an interrupt vector, indicating whether the corrector or image reconstructor has finished processing data. This interrupt vector is applied to the computer bus via data drivers 902. Following each image reconstruction cycle for the data from a projection, computer 130 must provide new image reconstruction constants to the image reconstructor circuitry, as described above. Similarly, for each new set of projection data processed by corrector 112, the computer 130 must provide the base address of the next block of data. Once the kernal data has been loaded into convolver 114, the convolver operates without needing any further data from computer 130; and thus, no interrupt need be provided to computer 130 from convolver 114.

As described in detail above in the description of the corrector circuitry, the data which is processed by the corrector is read from the computer via DMA. Handshaking control signals to and from the convolver requesting a DMA cycle and indicating that the computer memory is available go through DMA control circuitry 938 which causes the proper signals to be applied to computer bus 900 by bus control 910. For further information on these DMA control signals, the above-referenced Digital Equipment Corporation interfacing handbook should be consulted.

The address data from corrector 112, designating the data to be read during a DMA cycle, is applied to computer bus 900 via address drivers 906. A base address register 940 is loaded by the computer and contains a base address indicating the starting point in computer memory of the block of data to be accessed by the corrector. The lower order bits of the address provided to the computer are calculated by the corrector and applied to address drivers 906 through corrector address receivers 914.

There has been described a novel processor for use with a tomography system. It will be appreciated that modifications to the preferred embodiment of the present invention described herein may be made by those of ordinary skill in the art without departing from the intended scope of the invention. Therefore, the invention is to be construed only in accordance with the appended claims and is not to be limited by the above description of a preferred embodiment.

What is claimed is:

1. In a tomography system for exposing a body to radiation to provide image data representative of the density of the body in a cross-sectional plane, of the type having: source means for providing radiation passing through the body; detector means for receiving the radiation passing through the body along a plurality of paths and for providing output signals representative of radiation intensity received; and scanning means for providing for rotation of the source and detector means with respect to said body and for periodically causing emission of radiation from the source means during said rotation to provide a scan having a plurality of projections at a corresponding plurality of projection angles; the tomography processor comprising:

corrector means for correcting the output signals from the detector means to provide corrected data points, each representative of a line integral of the density of the body along the path traversed by the radiation producing the corresponding detector means output signal;

first memory means for storing the corrected data points from a projection and for retrieving the stored, corrected data points from a projection at a later time;

convolver means for convolving with a deblurring function the corrected data points from a projection, retrieved by the first memory means, to produce a plurality of convolved data points from a projection;

second memory means, coupled to the convolver means, for storing the convolved data points from a projection and for retrieving the stored, convolved data points from a projection at a later time;

image memory means for storing data representative of the density of the body in said cross-sectional plane and having a plurality of memory locations each for storing a value representative of the density of a corresponding area of the body in said cross-sectional plane;

reconstructor means, coupled to said second memory means, and operative in response to data retrieved by said second memory means, for back-projecting the convolved data points from a projection by determining the corresponding convolved data point for each location in image memory and adding data derived from the corresponding convolved data point to the value stored in that location in image memory.

2. The tomography processor of claim 1 further comprising:

control means for sequentially activating the corrector and convolver, so as to process the data from each projection in a scan to produce a plurality of convolved data points from each projection and for activating the reconstructor means to back-project the convolved data from each projection in a scan to produce data in each location in the image memory means representative of the density of the corresponding area of the body.

3. The tomography processor of claim 2 wherein each of the first and second memory means includes a two-bank memory, comprising:

a first memory bank;

a second memory bank; and means for storing data in a first one of said first and second memory banks and for retrieving data from the second one of said first and second memory banks in response to a selection signal designating in which bank data is to be stored and from which bank data is to be retrieved;

the tomography processor further including:

means for providing selection signals to the first memory means so that corrected data points from a projection may be stored therein while corrected data points from a prior projection may be concurrently retrieved therefrom; and means for providing selection signals to the second memory means so that convolved data points from a projection may be stored therein while convolved data points from a prior projection may be concurrently retrieved therefrom.

4. The tomography processor of claim 3 wherein the reconstructor means further includes means for multiplying each convolved data point by a weighting factor to provide the data to be added to the value stored in the corresponding location in image memory.

5. The tomography processor of claim 4 wherein the corrector means includes means for performing calculations to compensate for previously measured errors between the output signals produced by the detector means and the actual intensity of radiation received thereby, and to compensate for beam-hardening of the radiation passing through the body.

6. The tomography processor of claim 5 wherein the source means provides a fan-beam of radiation.

7. The tomography processor of claim 3 further including third memory means for storing the detector means output signals from a projection and for retrieving the stored output signals during a subsequent projection.

8. The tomography processor of claim 3 wherein the corrector, convolver, and reconstructor means each compose stages of a pipeline processor, and wherein the first and second memory means, and the image memory means compose intermediate storage sections of a pipeline processor; and wherein the tomography processor includes means for controlling each of the intermediate memory sections and for causing each of the pipeline processor stages to sequentially process the data points from each projection stored in and retrieved by the previous intermediate memory section to produce data points stored by the following intermediate memory section to produce the final image data.

9. The tomography processor of claim 4 wherein the source means provides a fan-beam of radiation passing through the body; and wherein the detector means includes a plurality of detectors, each for detecting radiation intensity and for producing an output signal representative thereof, located along a semi-circle having a center located at the source, each of the detector means being located at a respective detector angle with respect to a line passing through the source means and the axis of rotation.

10. The tomography processor of claim 9 wherein the corrector means further includes means for multiplying the output signal from each of the detectors by the cosine of the detector angle of the detector producing the respective output signal to produce the corrected data points.

11. The tomography processor of claim 10 wherein the weighting factor by which the reconstructor means multiplies the convolved data points is equal to the reciprocal of the square of the distance from the source means to the area of the body corresponding with the location in image memory in which the weighted and convolved data point is to be stored.

12. The tomography processor of claim 2 wherein the control means includes a programmable, digital processor.

13. The tomography processor of claim 12 further comprising:

corrector activation means, operative in response to a corrector activation signal, for causing the corrector to begin correcting the output signals from a projection from the detector means and to cease correcting output signals from the detector means when all of the output signals from a projection have been corrected;

convolver activation means, operative in response to a convolver activation signal for causing the convolver to begin convolving corrected data points from a projection and for causing the convolver to cease convolving corrected data points when all the corrected data points from a projection have been convolved; and reconstructor activation means, operative in response to a reconstructor activation signal for causing the reconstructor to begin back-projecting the convolved data points from a projection and for causing the reconstructor to cease back-projecting the convolved data from a projection when all of the convolved data points from a projection have been back-projected; and wherein the corrector, convolver, and reconstructor activation signals are provided by the control means.

14. The tomography processor of claim 13 wherein the corrector means is directly coupled to the first memory means and wherein the first memory means is directly coupled to the convolver means.

15. A fan-beam tomography system for providing data representative of the density of a body in a cross-sectional plane, comprising:

source means for emitting a fan-beam of radiation passing through the body;

detector means for receiving radiation passing through the body along a plurality of paths and for providing corresponding output signals representative of radiation intensity received along each of said paths;

scanning means for providing for relative rotation about an axis of the source and detector means with respect to the body and for causing the source means to emit radiation during said rotation to provide a scan made up of a plurality of projections at a corresponding plurality of projection angles;

the detector means including a plurality of detectors, each for detecting radiation intensity and for producing an output signal representative thereof, located along a semi-circle having a center located at the source, each of the detectors being located at a respective detector angle with respect to a line passing through the source means and the axis of rotation;

corrector means for receiving each of the output signals from the detector means and for providing in response thereto, a corresponding corrected data point representative of a line integral of the density of the body along the corresponding path of the radiation received by the detector means, including:

means for performing calculations to compensate for previously measured errors between the output signals produced by the detector means and the actual intensity of radiation received thereby and to compensate for beam-hardening of the radiation passing through the body; and means for multiplying the output signal from each of the detectors by the cosine of the respective detector angle to provide the corrected data points;

first memory means for storing the corrected data points from a projection and for retrieving the stored, corrected data points from a projection at a later time;

convolver means for convolving with a deblurring function the corrected data points from a projection, retrieved by the first memory means, to produce a plurality of convolved data points from a projection;

second memory means, coupled to the convolver means, for storing the convolved data points from a projection and for retrieving the stored, convolved data points from a projection at a later time;

an image memory having a plurality of memory locations each for storing a value representative of the density of a corresponding area of the body in the cross-sectional plane; and reconstructor means, coupled to said second memory means, and operative in response to data retrieved by said second memory means, for back-projecting the convolved data points from a projection, including:

address means for sequentially providing address data for accessing each of the locations in image memory during each projection;

locator means, responsive to data derived from said address data, for determining which of the convolved data points from a projection corresponds with the presently accessed image memory location;

means for multiplying the corresponding data point determined by said locator means by a weighting factor to produce a weighted data point; and means for adding the weighted data point to the value, resulting from prior projections, stored in the presently accessed image memory location and for storing the sum thereof in the presently accessed memory location to replace the value resulting from prior projections.

16. The tomography system of claim 15 further comprising control means including:

means for sequentially causing the corrector and convolver means to process the data from each projection in a scan to produce a plurality of convolved data points from each projection; and means for causing the reconstructor means to reconstruct the convolved data points from each projection in a scan to produce data in each location in the image memory representative of the density of the corresponding area of the body.

17. The tomography system of claim 15 wherein the weighting factor by which the reconstructor means multiplies the convolved data point is equal to the reciprocal of the square of the distance from the source means to the area of the body corresponding with the accessed location in image memory.

18. The tomography system of claim 17 wherein the fan-beam of radiation includes x-rays.

19. The tomography system of claim 18 further comprising control means including:

means for sequentially causing the corrector and convolver means to process the data from each projection in a scan to produce a plurality of convolved data points from each projection; and means for causing the reconstructor means to reconstruct the convolved data points from each projection in a scan to produce data in each location in the image memory representative of the density of the corresponding area of the body.

20. The tomography system of claim 19 wherein the control means includes a programmable, digital processor.

21. The tomography system of claim 17 wherein each of the plurality of image memory locations is associated with an area of the body, the address of each location 29. The tomography system of claim 28 further including means for causing each integrator to enter autozero mode substantially immediately after the output signal therefrom is converted to digital form by the analog-to-digital converter.

30. The tomography system of claim 29 wherein the plurality of detectors is arranged in a linear array and wherein said multiplexing means provides the integrated detector output signals to said converter in a sequence in which the integrated detector output signals are provided in the order in which their respective associated detectors are located in the linear array, beginning with detectors located in the center of the array and proceeding to the ends of the array.

31. The tomography system of claim 25 wherein said corrector means is directly coupled to said first memory means and wherein said first memory means is directly coupled to said convolver means.

32. The tomography system of claim 24 wherein each of the plurality of image memory locations is associated with an area of the body, the address of each location also being representative of coordinates of the associated body area in an image memory coordinate system fixed with respect to the body; and wherein the reconstructor means further includes transformation means, operative in response to address data from the address means, for providing data representative of projection system coordinates, in a coordinate system fixed with respect to the radiation source and detector means, of the body area associated with the presently accessed image memory location.

33. The tomography system of claim 32 wherein the transformation means includes means for adding incremental values to the data representative of projection system coordinates of the image memory location previously accessed to produce data representative of the projection system coordinates of the body area associated with the presently accessed image memory location;

wherein the body areas associated with the image memory location are arranged along orthogonal rows and columns;
and further comprising:
means for providing projection-angle data representative of the angle between the projection coordinate system and the image memory coordinate system; and
means responsive to the projection-angle data for providing to the transformation means data representative of δ·sin θ and δ·cos θ values, where δ is the distance along the rows and columns between adjacent body areas and θ is the projection angle, for determining said incremental values.

34. A fan-beam tomography system for providing data representative of the density of a body in a cross-sectional plane, comprising:
source means for emitting a fan-beam of radiation passing through the body;
detector means for receiving radiation passing through the body along a plurality of paths and for providing corresponding output signals representative of radiation intensity received along each of said paths;
scanning means for providing for relative rotation about an axis of the source and detector means with respect to the body and for causing the source means to emit radiation during said rotation to provide a scan made up of a plurality of projections at a corresponding plurality of projection angles;
corrector means for receiving each of the output signals from the detector means and for providing in response thereto, a corresponding corrected data point representative of a line integral of the density of the body along the corresponding path of the radiation received by the detector means, including:
means for performing calculations to compensate for previously measured errors between the output signals produced by the detector means and the actual intensity of radiation received thereby;
first memory means for storing the corrected data points from a projection and for retrieving the stored, corrected data points from a projection at a later time;
convolver means for convolving with a deblurring function the corrected data points from a projection, retrieved by the first memory means, to produce a plurality of convolved data points from a projection;
second memory means, coupled to the convolver means, for storing the convolved data points from a projection and for retrieving the stored, convolved data points from a projection at a later time;
an image memory having a plurality of memory locations, each for storing a value representative of the density of an associated area of the body in the cross-sectional plane, each of the plurality of image memory locations being associated with an area of the body, the address of each location also being representative of coordinates of the associated body area in an image memory coordinate system fixed with respect to the body;
reconstructor means, coupled to said second memory means, and operative in response to data retrieved by said second memory means, for back-projecting the convolved data points from a projection, including:
address means for sequentially providing address data for accessing each of the locations in image memory during each projection;
transformation means, operative in response to address data from the address means, for performing a two-dimensional coordinate transformation to provide data representative of projection system coordinates in a coordinate system fixed with respect to the radiation source and detector means, of the body area associated with the presently accessed image memory location;
locator means, responsive to projection system coordinate data from said transformation means, for determining which of the convolved data points from a projection corresponds with the presently accessed image memory location;
means for multiplying the corresponding data point determined by said locator means by a weighting factor to produce a weighted data point; and
means for adding the weighted data point to the value, resulting from prior projections, stored in the presently accessed image memory location and for storing the sum thereof in the presently accessed memory location to replace the value resulting from prior projections.

35. The tomography system of claim 34 further comprising control means, including:

also being representative of coordinates of the associated body area in an image memory coordinate system fixed with respect to the body; and wherein the reconstructor means further includes transformation means, operative in response to address data from the address means, for providing data representative of projection system coordinates, in a coordinate system fixed with respect to the radiation source and detector means, of the body area associated with the presently accessed image memory location.

22. The tomography system of claim 21 wherein the control means further includes means for providing projection angle data representative of the angle between the projection coordinate system and the image memory coordinate system; and wherein the transformation means includes means responsive to the projection angle data for adding incremental values to the data representative of projection system coordinates of the image memory location previously accessed to produce data representative of the projection system coordinates of the body area associated with the presently accessed image memory location.

23. The tomography system of claim 21 wherein the convolver means further includes interpolation means, responsive to the plurality of convolved data points for providing interpolated data points corresponding with paths lying between the paths for which the detector means provides corresponding output signals, so that the data points from said convolver means include convolved data points each corresponding with a path for which the detector means provides an output signal, and interpolated data points corresponding with paths lying between the paths for which the detector means produces an output signal.

24. A fan-beam tomography system for providing data representative of the density of a body in a cross-sectional plane, comprising:

source means for emitting a fan-beam of radiation passing through the body;

detector means for receiving radiation passing through the body along a plurality of paths and for providing corresponding output signals representative of radiation intensity received along each of said paths;

scanning means for providing for relative rotation about an axis of the source and detector means with respect to the body and for causing the source means to emit pulses of radiation during said rotation to provide a scan made up of a plurality of projections at a corresponding plurality of projection angles;

the detector means including:

a plurality of detectors each for detecting radiation intensity and for producing an output signal representative thereof;

a plurality of integrators, each associated with a respective one of said detectors, for integrating the output signal of the associated detector during each projection to produce an integrated detector output signal representative of the integral of the output signal during each projection from the associated detector; and conversion means, responsive to each of the integrated detector output signals for providing detector means output signals representative of the inverse of the logarithm of each of the integrated detector output signals;

corrector means for receiving each of the output signals from the detector means and for providing in response thereto, a corresponding corrected data point representative of a line integral of the density of the body along the corresponding path of the radiation received by the detector means, including:

means for performing calculations to compensate for previously measured errors between the output signals produced by the detector means and the actual intensity of radiation received thereby;

first memory means for storing the corrected data points from a projection and for retrieving the stored, corrected data points from a projection at a later time;

convolver means for convolving with a deblurring function the corrected data points from a projection, retrieved by the first memory means, to produce a plurality of convolved data points from a projection;

second memory means, coupled to the convolver means, for storing the convolved data points from a projection and for retrieving the stored, convolved data points from a projection at a later time;

an image memory having a plurality of memory locations each for storing a value representative of the denstiy of a corresponding area of the body in the cross-sectional plane; and reconstructor means, coupled to said second memory means and operative in response to data retrieved by the second memory means, for back-projecting the convolved data points from a projection, including:

address means for sequentially providing address data accessing each of the locations in image memory during each projection;

locator means, responsive to data derived from said address data, for determining which of the convolved data points from a projection corresponds with the presently accessed image memory location;

means for multiplying the corresponding data point determined by said locator means by a weighting factor to produce a weighted data point; and means for adding the weighted data point to the value, resulting from prior projections, stored in the presently accessed image memory location and for storing the sum thereof in the presently accessed image memory location to replace the value resulting from prior projections.

25. The tomography system of claim 24 wherein the conversion means includes at least one logarithmic analog-to-digital converter for providing digital representations of the integrated detector output signals.

26. The tomography system of claim 25 wherein the integrators each include integrators having an auto-zero mode for reducing drift errors therein.

27. The tomography system of claim 26 including means for selecting auto-zero mode for each of the integrators prior to the emission of each pulse of radiation from the source means.

28. The tomography system of claim 26 further comprising means for multiplexing the integrated detector output signals so that the integrated detector output signals are serially provided to the at least one logarithmic converter for conversion to digital form.

means for sequentially causing the corrector and convolver means to process the data from each projection in a scan to produce a plurality of convolved data points from each projection;

means for causing the reconstructor means to reconstruct the convolved data points from each projection in a scan to produce data in each location in the image memory representative of the density of the corresponding area of the body; and means for providing projection angle data representative of the angle between the projection coordinate system and the image memory coordinate system; and wherein the transformation means includes means responsive to the projection angle data for adding incremental values to the data representative of projection system coordinates of the image memory location previously accessed to produce data representative of the projection system coordinates of the body area associated with the presently accessed image memory location.

36. The tomography system of claim 35 wherein the body areas associated with the image memory locations are arranged along orthogonal rows and columns so that the image memory coordinate system is a two-dimensional Cartesian coordinate system.

37. The tomography system of claim 34 wherein the transformation means includes means for adding incremental values to the data representative of projection system coordinates of the image memory location previously accessed to produce data representative of the projection system coordinates of the body area associated with the presently accessed image memory location.

38. The tomography system of claim 37 wherein the body areas associated with the image memory location are arranged along orthogonal rows and columns, and further comprising:

means for providing projection-angle data representative of the angle between the projection coordinate system and the image memory coordinate system; and means responsive to the projection-angle data for providing to the transformation means data representative of $\delta \cdot \sin \theta$ and $\delta \cdot \cos \theta$ values, where $\delta$ is the distance along the rows and columns between adjacent body areas and $\theta$ is the projection angle, for determining said incremental values.

39. The tomography system of claim 38 wherein the means for providing data representative of $\delta \cdot \sin \theta$ and $\delta \cdot \cos \theta$ values includes a programmable, digital processor.

40. The tomography system of claim 39 wherein the digital processor provides $\delta \cdot \sin \theta$ and $\delta \cdot \cos \theta$ values for a projection during a previous projection.

41. The tomography system of claim 38 wherein the locator means includes a read-only memory for storing data representative of a locator function associating each location in image memory with one of the paths corresponding with the convolved data points.

42. The tomography system of claim 41 wherein the locator means read-only memory provides data representative of coefficients of a two-dimensional piece-wise linear expansion of the locator function as a function of the projection system coordinates of the presently accessed image memory location; and wherein the locator means further includes means for multiplying the projection system coordinate data from the transformation means by the expansion coefficients provided by the locator factor read-only memory and for adding the products thereof to provide the locator function value.

43. The tomography system of claim 38 wherein the corrector means is directly coupled to the first memory means and wherein the first memory means is directly coupled to the convolver means.

44. The tomography system of claim 37 wherein the means for multiplying includes a weighting factor means, responsive to data from the transformation means, for producing the weighting factor.

45. The tomography system of claim 44 wherein the weighting factor means includes a read-only memory responsive to the projection system coordinate data from said transformation means for providing at its output, data representative of the weighting factor.

46. The tomography system of claim 45 wherein the weighting factor by which the reconstructor means multiplies the convolved data point is equal to the reciprocal of the square of the distance from the source means to the area of the body corresponding with the presently accessed location in image memory.

47. The tomography system of claim 45 wherein weighting factor means read-only memory provides data representative of coefficients of a two-dimensional piece-wise quadratic expansion of the weighting factor as a function of the projection system coordinates of the presently accessed image memory location; and wherein the weighting factor means further includes means for multiplying the projection system coordinate data from the transformation means by the expansion coefficients provided by the weighting factor read-only memory and for adding the products thereof to provide the weighting factor.

48. The tomography system of claim 45 further comprising:

locator read-only memory means responsive to projection sysem coordinates from the transformation means for providing output signals representative of which input data point contains data representative of the body area associated with the image memory location presently addressed by the address means.

49. The tomography system of claim 48 wherein the locator means read-only memory and the weighting means read-only memory produce output data representative of the coefficients of mathematic expansions, in terms of the projection system coordinates, providing data respectively representative of the data point selected by the locator means and the weighting factor provided by the weighting means.

50. The tomography system of claim 34:

wherein the convolver means further includes interpolation means, responsive to the plurality of convolved data points for providing interpolated data points corresponding with paths lying between the paths for which the detector means provides corresponding output signals, so that the data points from said convolver means include convolved data points each corresponding with a path for which the detector means provides an output signal, and interpolated data points corresponding with paths lying between the paths for which the detector means produces an output signal; and wherein the locator means includes means, operative in response to data from said transformation means, for selecting from among said convolved data points and said interpolated data points the data point having a corresponding path passing most closely to center of the area of the body corresponding with the presently accessed image memory location.

51. For use in a fan-beam tomography system having a source of radiation and means for detecting radiation for providing data representative of the density of a body in a cross-sectional plane, of the type having a corrector, a convolver, and an image reconstructor respectively interconnected by two intermediate, two-bank memories and operative as a multistage pipeline processor to provide a plurality of convolved data points from each of a plurality of tomographic projections in response to data from said detecting means, an image reconstructor for performing back projection of the plurality of convolved data points taken during each of the plurality of projections, comprising:

an image memory having a plurality of memory locations each associated with an area of the body in the cross-sectional plane, for storing data representative of the density of the associated body area, each location having an address, the address of each location also being representative of coordinates of the associated body area in an image memory coordinate system fixed with respect to the body;

address means for providing address data to the image memory for accessing each of the memory locations during each projection;

transformation means, operative in response to address data from the address means, for providing data representative of projection system coordinates, in a coordinate system fixed with respect to the radiation source and detecting means, of the body area associated with the presently accessed image memory location;

locator means, operative in response to the projection system coordinate data from the transformation means, for selecting from among the convolved data points, the convolved data point having data representative of the density of the body area associated with the image memory location presently accessed by the address means; and means for adding the value stored in the presently accessed image memory location to data derived from the convolved data point selected by the locator means, and for storing the sum thereof in the presently accessed image memory location to replace the previously stored value.

52. The image reconstructor of claim 51 wherein the address means includes means for sequentially providing address data representative of adjacent body areas; and wherein the transformation means includes means for adding incremental values to the data representative of the projection system coordinates of the image memory location previously accessed to produce data representative of the projection system coordinates of the body area associated with the presently accessed image memory location.

53. The image reconstructor of claim 52 wherein the body areas associated with the image memory location are arranged along orthogonal rows and columns, and further comprising:

means for providing projection-angle data representative of the angle between the projection coordinate system and the image memory coordinate system;

means responsive to the projection-angle data for providing data representative of $\delta \cdot \sin \theta$ and $\delta \cdot \cos \theta$ values, where $\delta$ is the distance along the rows and columns between adjacent body areas and $\theta$ is the projection angle; and wherein the means for adding includes means for selectively adding the $\delta \cdot \sin \theta$ and the $\delta \cdot \cos \theta$ to the data representative of the projection system coordinates of the image memory location previously accessed.

54. The image reconstructor of claim 53 wherein the means for providing data representative of $\delta \cdot \sin \theta$ and $\delta \cdot \cos \theta$ values includes a programmable, digital processor.

55. The image reconstructor of claim 54 wherein the digital processor provides $\delta \cdot \sin \theta$ and $\delta \cdot \cos \theta$ values for a projection during a previous projection.

56. The image reconstructor of claim 51 further including:

weighting means, operative in response to the projection system coordinate data, for providing a weighting factor;

means for multiplying the weighting factor and the data point selected by the locator means to provide a weighted data point;

the weighted data point being added by the means for adding to the value stored in the presently addressed image memory location.

57. The image reconstructor of claim 56 wherein the weighting factor is equal to the reciprocal of the square of the distance between the source of radiation and the body area associated with the presently addressed image memory location.

58. The image reconstructor of claim 56 wherein the weighting means includes a read-only memory responsive to the projection system coordinate data from said transformation means for providing at its output, data representative of the weighting factor.

59. The image reconstructor of claim 58 wherein the weighting factor by which the reconstructor means multiplies the convolved data point is equal to the reciprocal of the square of the distance from the source means to the area of the body corresponding with the presently accessed location in image memory.

60. The image reconstructor of claim 58 wherein the weighting factor means read-only memory provides data representative of coefficients of a two-dimensional piece-wise quadratic expansion of the weighting factor as a function of the projection system coordinates of the presently accessed image memory location; and wherein the weighting factor means further includes means for multiplying the projection system coordinate data from the transformation means by the expansion coefficients provided by the weighting means read-only memory and for adding the products thereof to provide the weighting factor.

61. The image reconstructor of claim 58 further comprising:

locator read-only memory means responsive to projection system coordinates from the transformation means for providing output signals representative of which convolved data point contains data representative of the body area associated with the image memory location presently accessed by the address means.

62. The image reconstructor of claim 61 wherein the locator means read-only memory and the weighting means read-only memory produce output data representative of coefficients of mathematical expansions, in terms of the projection system coordinates, providing data respectively representative of the data point selected by the locator means and the weighting factor provided by the weighting factor.

63. The image reconstructor of claim 51 wherein the locator means includes a read-only memory for storing data representative of a locator function associating each location in image memory with one of the paths corresponding with the convolved data points.

64. The image reconstructor of claim 63 wherein the locator means read-only memory provides data representative of coefficients of a two-dimensional piecewise linear expansion of the locator function as a function of the projection system coordinates of the presently accessed image memory location; and wherein the locator means further includes means for multiplying the projection system coordinate data from the transformation means by the expansion coefficients provided by the locator means read-only memory and for adding the products thereof to provide the locator function value.

65. In a fan-beam tomography system for exposing a body to radiation to provide data representative of the density of the body in a cross-sectional plane, of the type having: source means for providing radiation for passage through the body; detector means for receiving the radiation passing through the body along a plurality of paths and for providing output signals representative of radiation intensity received, and scanning means for providing rotation of the source and detector means with respect to said body and for causing emission of radiation from the source means during said rotation to provide a scan having a plurality of projections at a corresponding plurality of projection angles;

the method of processing the detector means output signals, comprising the steps of:

correcting the output signals from the detector means to provide corrected data points, each representative of a line integral of the density of the body along the path traversed by the radiation producing the corresponding detector means output signal;

storing in a first memory the corrected data points from a projection;

retrieving from the first memory the stored, corrected data points from a projection after all the corrected data points from that projection have been stored;

convolving with a deblurring function the corrected data points from a projection, retrieved from the first memory, to produce a plurality of convolved data points from a projection;

storing the convolved data points from a projection in a second memory;

retrieving from the second memory the stored, convolved data points from a projection after all the convolved data points from the projection have been stored;

providing an image memory having a plurality of memory locations corresponding with a similar plurality of areas of the body in said plane, for storing data representative of the density of the corresponding area of the body; and back-projecting the convolved data points from a projection retrieved by said second memory by:

sequentially accessing each location in the image memory;

determining the corresponding convolved data point for the presently accessed location in image memory;

multiplying the previously-determined corresponding convolved data point by a weighting factor to provide a weighted data point;

adding the weighted data point to the value stored in the presently accessed location in the image memory; and storing the results of the adding step in the presently accessed location in the image memory to replace the value previously stored therein;

repeating the preceeding steps to correct, convolve, and back-project the data from each projection in a scan to produce data in each location in the image memory representative of the density of the corresponding area of the body;

wherein each of the first and second memories includes a two-bank memory, having a first memory bank and a second memory bank;

wherein the steps of storing and retrieving in said first and second memories include the steps of storing data in a first one of said first and second memory banks in the respective memories and concurrently retrieving data from the second one of said first and second memory banks in the respective memories in response to a selection signal designating in which bank data is to be stored and from which bank data is to be retrieved; and wherein the step of repeating includes the step of providing selection signals for the first memory so that corrected data points from a projection may be stored in one bank thereof while corrected points from a prior projection may be retrieved from the other bank thereof.

66. The method of claim 65 further including the step of:

prior to exposing the body to radiation to provide data representative of the densities thereof and without said body between the source means and the detector means, causing emission of radiation from the source means and measuring the output signals from the detector means to determine errors between the output signals produced by the detector means and the actual intensity of radiation received thereby;

and wherein the step of correcting includes the step of performing calculations to compensate for the previously determined errors, and to compensate for beam-hardening of the radiation passing through the body.

67. The method of claim 66 wherein the step of correcting further includes the step of multiplying each convolved data point by a weighting factor prior to storing the convolved data point in the corresponding location in image memory.

68. The method of claim 67 further including the step of storing output signals from the detector means from a projection and retrieving the stored output signals during a subsequent projection.

* * * * *